United States Patent
Lee et al.

(10) Patent No.: US 9,988,687 B2
(45) Date of Patent: Jun. 5, 2018

(54) COMPANION DIAGNOSTICS FOR CANCER AND SCREENING METHODS TO IDENTIFY COMPANION DIAGNOSTICS FOR CANCER BASED ON SPLICING VARIANTS

(71) Applicants: Norman Lee, Dayton, MD (US); Bi-Dar Wang, Potomac, MD (US)

(72) Inventors: Norman Lee, Dayton, MD (US); Bi-Dar Wang, Potomac, MD (US)

(73) Assignee: THE GEORGE WASHINGTON UNIVERISTY DC (US)

( * ) Notice: Subject to any disclaimer, the term of this patent is extended or adjusted under 35 U.S.C. 154(b) by 173 days.

(21) Appl. No.: 14/639,219

(22) Filed: Mar. 5, 2015

(65) Prior Publication Data

US 2015/0252432 A1    Sep. 10, 2015

Related U.S. Application Data

(60) Provisional application No. 61/948,218, filed on Mar. 5, 2014.

(51) Int. Cl.
  *C12Q 1/68* (2018.01)
  *C12P 19/34* (2006.01)
  *G01N 33/50* (2006.01)

(52) U.S. Cl.
  CPC ....... *C12Q 1/6886* (2013.01); *G01N 33/5011* (2013.01); *C12Q 2600/158* (2013.01)

(58) Field of Classification Search
  None
  See application file for complete search history.

(56) References Cited

U.S. PATENT DOCUMENTS

| | | | |
|---|---|---|---|
| 4,683,195 A | 7/1987 | Mullis et al. | |
| 4,683,203 A | 7/1987 | Anton et al. | |
| 6,116,013 A | 9/2000 | Moller et al. | |
| 6,333,155 B1 | 12/2001 | Lockhart et al. | |
| 6,608,053 B2 | 8/2003 | Hayakawa et al. | |
| 7,960,517 B2 | 6/2011 | Do Couto et al. | |
| 7,985,560 B2 | 7/2011 | Valkirs et al. | |
| 2010/0286178 A1 * | 11/2010 | Ibrahim ............... | A61K 31/437 514/274 |

FOREIGN PATENT DOCUMENTS

WO    WO 2013043878 A2 *   3/2013   ............. C07K 14/47

OTHER PUBLICATIONS

Mizoguchi et al., "Genetic Alterations of Phosphoinositide 3-kinase Subunit Genes in Human Glioblastomas," Brain Pathology, Oct. 2004, vol. 14, issue 4, pp. 372-377.*

(Continued)

*Primary Examiner* — Young J Kim
(74) *Attorney, Agent, or Firm* — Cooley LLP

(57) ABSTRACT

A method of classifying a patient for eligibility for cancer therapy based on the presence or absence of splicing variants in a sample of the patient's cancer tissue. Also, a method of screening cancer therapies for efficacy against splicing variants. More specifically, the methods relate to novel splicing variants of genes associated with cancer risk and survival, particularly splicing variants of PIK3CD, FGFR3, TSC2, RASGRP2, ITGA4, MET, NF1 and BAK1. Also more specifically, the methods relate to classifying a patient for eligibility for cancer therapy involving the use of GS-1101.

16 Claims, 10 Drawing Sheets

(56) References Cited

OTHER PUBLICATIONS

Wu et al., "Somatic mutation and gain of copy number of PIK3CA in human breast cancer," Breast Cancer Research, vol. 7, pp. R609-R616. (Year: 2005).*
Cornillet-Lefebvre et al., "Constitutive phosphoinositide 3-kinase activation in acute myeloid leukemia is not due to p110delta mutations," Leukemia, vol. 20, pp. 374-376 (Year: 2006).*
Cizkova et al., "PIK3R1 underexpression is an independent prognostic marker in breast cancer," BMC Cancer, vol. 13, pp. 1-15 (Year: 2013).*
Black, DL, "Mechanisms of alternative pre-messenger RNA splicing." Annu Rev Biochem, 2003, vol. 72, pp. 291-336.
Boise, LH et al., "bcl-x, a bcl-2-related gene that functions as a dominant regulator of apoptotic cell death". Cell, 1993, vol. 74, pp. 597-608.
David, CJ et al. "Alternative pre-mRNA splicing regulation in cancer: pathways and programs unhinged", Genes Dev., 2010, vol. 24, No. 21, pp. 2343-2364.
Venables, JP et al., "Cancer-associated regulation of alternative splicing", Nat Struct Mol Biol., 2009, vol. 16, No. 6, pp. 670-676.
Venables, JP., "Unbalanced alternative splicing and its significance in cancer," Bioessays, 2006, vol. 28, No. 4, pp. 378-386.
Skotheim, RI et al., "Alternative splicing in cancer: noise, functional, or systematic?", Int J Biochem Cell Biol., 2007, vol. 39, No. 7-8, pp. 1432-1449.
Omenn, GS et al., "Alternative splice variants, a new class of protein cancer biomarker candidates: findings in pancreatic cancer and breast cancer with systems biology implications," Dis Markers., 2010, vol. 28, No. 4, pp. 241-251.
Rajan, P et al., "Alternative splicing and biological heterogeneity in prostate cancer", Nat Rev Urol., 2009, vol. 6, No. 3, pp. 454-460.
Ghigna, C et al.,"Alternative Splicing and Tumor Progression", Curr Genomics., 2008, vol. 9, No. 8, pp. 556-570.
Minn, AJ et al., "Bcl-xS Antagonizes the Protective Effects of Bcl-xL", J Biol Chem. ,1996, vol. 271, No. 11, pp. 6306-6312.
Olopade, OI et al., "Overexpression of BCL-x protein in primary breast cancer is associated with high tumor grade and nodal metastases", Cancer J Sci Am., 1997, vol. 3, No. 4, pp. 230-237.
Takehara, T et al., "Expression and role of Bcl-xL in human hepatocellular carcinomas", Hepatology. 2001, vol. 34, No. 1, pp. 55-61.
Bouillet, P et al, "CD95, BIM and T cell homeostasis", Nat Rev Immunol. 2009, vol. 9, No. 7, pp. 514-519.
Cheng, J et al., "Protection from Fas-mediated apoptosis by a soluble form of the Fas molecule," Science. 1994, vol. 263, No. 5154, pp. 1759-1762.
Cascino, I et al., "Three functional soluble forms of the human apoptosis-inducing Fas molecule are produced by alternative splicing," Journal of immunology. 1995, vol. 154, No. 6, pp. 2706-2713.
Cohen, JB et al., "Expression of the H-ras proto-oncogene is controlled by alternative splicing," Cell. 1989, vol. 58, No. 3, pp. 461-472.
Barbier, J et al., "Regulation of H-ras Splice Variant Expression by Cross Talk between the p53 and Nonsense-Mediated mRNA Decay Pathways," Mol Cell Biol. 2007, vol. 27, No. 20, pp. 7315-7333.
Gunthert, U et al., "A New Variant of Glycoprotein CD44 Confers Metastatic Potential to Rat Carcinoma Cells," Cell. 1991, vol. 65, No. 1, pp. 13-24.
Wang, J et al., "Expression of Variant TMPRSS2/ERG Fusion Messenger RNAs is Associated with Aggressive Prostate Cancer," Cancer Res. 2006, vol. 66, No. 17, pp. 8347-8351.
Tomlins, SA et al., "Urine PCA3 and TMPRSS2:ERG Using Cancer-specific Markers to Detect Cancer," Eur Urol. 2014, vol. 65, No. 2, pp. 543-545.
Sahadevan, K et al., , "Selective over-expression of fibroblast growth factor receptors 1 and 4 in clinical prostate cancer," J Pathol. 2007, vol. 213, No. 1, pp. 82-90.
Gnanapragasam, VJ et al., "FGF8 isoform b expression in human prostate cancer," Br J Cancer. 2003, vol. 88, No. 9, pp. 1432-1438.
Beaucage, S.L., "Deoxynucleoside phosphoramidites—A new class of key intermediates for deoxypolynucleotide synthesis," Tet. Lett. 22: 1859-1862, 1981.
Thigpen, et al., "Four-amino acid segment in steroid 5 alpha-reductase 1 confers sensitivity to finasteride, a competitive inhibitor," J. Bio. Chem, 1992, vol. 267, pp. 8577-8583.
Saiki, et al., "Primer-directed enzymatic amplification of DNA with a thermostable DNA polymerase," Science, 1988, vol. 239, pp. 487-491.
Ding, Li et al., "Somatic mutations affect key pathways in lung adenocarcinoma", Nature, 2008, vol. 455, pp. 1069-1068.
Malek, RL et al., "Nrg-1 Belongs to the Endothelial Differentiation Gene Family of G Protein-coupled Sphingosine-1-phosphate Receptors", J Biol Chem. 2001, vol. 276, No. 8, pp. 5692-5699.
Joe, B et al., "Positional identification of variants of Adamts16 linked to inherited hypertension", Human molecular genetics. 2009, vol. 18, No. 15, pp. 2825-2838.
Glickman, M et al., "Molecular Cloning, Tissue-Specific Expression, and Chromosomal Localization of a Novel Nerve Growth Factor-Regulated G-Protein-Coupled Receptor, nrg-1", Molecular and cellular neuroscience. 1999, vol. 14, No. 2, pp. 141-152.
Riz, I. et al., "TLX1 and NOTCH coregulate transcription in T cell acute lymphoblastic leukemia cells," Molecular Cancer, 2010, vol. 9, p. 181.
Borrebaeck, et al., "Human antibody reactivity against the lower matrix protein (pp65) produced by cytomegalovirus," Clin Diagn Lab Immunol, 1995, vol. 2, No. 3, pp. 325-329.
Kohler and Milstein, "Continuous cultures of fused cells secreting antibody of predefined specificity," Nature, 1975, vol. 256, pp. 495-497.
Teramoto, H. et al., "Identification of H-Ras, RhoA, Rac1 and Cdc42 responsive genes.", Oncogene, 2003, vol. 22, No. 17, pp. 2689-2697.
Wang, B-D et al., "Prostate apoptosis response protein 4 sensitizes human colon cancer cells to chemotherapeutic 5-FU through mediation of an NFκB and microRNA network," Molecular Cancer. 2010. vol. 9, p. 98.
House, CD et al., "Voltage-Gated Na+ Channel SCN5A is a Key Regulator of a Gene Transcriptional Network That controls Colon Cancer Invasion," Cancer Res. 2010.
Irby, RB et al., "Iterative microarray and RNA interference-based interrogation of the SRC-induced invasive phenotype," Cancer Res. 2005, vol. 65, No. 5, pp. 1814-1821.
Healy, ZR et al, "Divergent responses of chondrocytes and endothelial cells to shear stress: Cross-talk among COX-2, the phase 2 response, and apoptosis," Proc Natl Acad Sci, 2005, vol. 102, No. 39, pp. 14010-14015.
Teramoto, H et al., "Autocrine activation of an osteopontin-CD44-Rac pathway enhances invasion and transformation by H-RasV12", Oncogene. 2005, vol. 24, No. 3, pp. 489-501.
Lannutti, BJ et al., "CAL-101, a p110σ selective phosphatidylinositol-3-kinase inhibitor for the treatment of B-cell malignancies, inhibits PI3K signaling and cellular viability," Blood 2011, vol. 117, No. 2, pp. 591-594.
Latt, S., "Microfluorometric Detection of Deoxyribonucleic Acid Replication in Human Metaphase Chromosomes", Proc. Nat. Acad. Sci. USA, 1973, vol. 70, No. 12, pp. 3395-3399.
Kwan,T. et al., "Genome-wide analysis of transcript isoform variation in humans". Nat Genet, 2008, vol. 40, pp. 225-231.
"Network TCGAR: Comprehensive genomic characterization defines human glioblastoma genes and core pathways", Nature, 2008, vol. 455, pp. 1061-1068.
Zhang, Y. et al., "Functional differences between integrin alpha4 and integrins alpha5/alphaV in modulating the motility of human oral squamous carcinoma cells in response to the V region and heparin-binding domain of fibronectin.", Exp Cell Res., 2004, vol. 295, pp. 48-58.
Herman, SE et al., "Phosphatidylinositol 3-kinase-delta inhibitor CAL-101 demonstrates promising preclinical activity in chronic lymphocytic leukemia by antagonizing intrinsic and extrinsic cellular survival signals," Blood, 2010, vol. 116, No. 12, pp. 2078-2088.

(56) References Cited

OTHER PUBLICATIONS

Witte, JS., "Genome-Wide Association Studies and Beyond," Annual Review of Public Health, 2010, vol. 31, pp. 9-20.

* cited by examiner

A

B

COMPANION DIAGNOSTICS FOR CANCER AND SCREENING METHODS TO IDENTIFY COMPANION DIAGNOSTICS FOR CANCER BASED ON SPLICING VARIANTS

CROSS-REFERENCE TO RELATED APPLICATIONS

This application claims priority to U.S. Provisional Patent Application No. 61/948,218, filed on Mar. 5, 2014, which is hereby incorporated by reference in its entirety for all purposes. U.S. Provisional Patent Application No. 61/536,957, filed on Sep. 20, 2011, is incorporated herein by reference. International patent application No. PCT/US2012/056346, filed Sep. 20, 2012 is incorporated herein by reference.

GOVERNMENT LICENSE RIGHTS

This invention was made with government support under R01-CA120316 and R01-DK056108 awarded by the NIH and W81XWH-13-1-0449 awarded by the USAMRMC. The government has certain rights in this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GWUV-001_01US_Sequence_Listing.txt, date recorded: Mar. 2, 2015, file size 101 kilobytes).

TECHNICAL FIELD

The present invention relates to novel splicing variants of a number of genes associated with prostate cancer risk and survival, and also the risk assessment, detection, diagnosis, or prognosis of prostate cancer (PCa). More specifically, this invention relates to the detection of certain splicing variants in genes PIK3CD and FGFR3, to determine the patient's eligibility for cancer treatments, particularly in the African American population.

BACKGROUND OF THE INVENTION

Prostate cancer (PCa) is the most common form of cancer among males. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

There are striking population (race) disparities in prostate cancer risk and survival outcome borne out of current health statistics data. This is particularly evident between African Americans (AA) and their Caucasian American (CA) counterparts.

Epidemiologic studies have shown that higher mortality and recurrence rates of prostate cancer are still seen in AA men even after adjustment for socioeconomic status, environmental factors and health care access. Thus, it is likely that biological differences account for some of the cancer disparities.

There remains a great need to study the pathological differences between AA and CA men and develop new detection and treatment options tailored to each population.

SUMMARY OF THE INVENTION

Prostate cancer (PCa) is a disease conferred by multiple gene mutations, numerous alternations in gene expression and aberrant changes in genome composition/architecture. The African American (AA) population exhibits higher incidence and mortality rates compared to Caucasian Americans (CA). The present invention, through systematic mRNA expression profiling, characterizes the global mRNA expression profiles in AA and CA prostate tissue samples. A large number of genes are shown to have differential expression between AA and CA patients. Notably, several genes residing within the 5 oncogenic signaling pathways have been identified as exhibiting differential splicing, which includes but not limited to PIK3CD, FGFR3, TSC2, FGFR2, PDGFRA, ITGA4, MET, EPHA3, NF1, RASGRP2, CTNNB1, TSC2, ATM, CDK4, and RBI between AA and CA PCa specimens. Quantitative analysis of the expression profiles of PIK3CD, FGFR3, TSC2, RASGRP2, ITGA4, MET, NF1 and BAK1 in prostate samples confirm differential splicing between the AA and CA patients. With certain splicing variants predominantly exist in AA patients. As a non-limiting example, PIK3CD is expressed predominantly as a long variant in CA patients, whereas the AA patient would have higher portion of a short variant. The alternatively spliced short variant of PIK3CD is found to be a more aggressive form. Increasing the short to long variants ratio in a PCa cell line (MDA PCa 2b) that is representative to the AA PCa PIK3CD expression profile, by knocking down PIK3CD long variant expression increases cell proliferation and cell migration. Selectively knocking down the expression of PIK3CD short variant in the same cell line, decreases the short to long variants ratio, and results in marked decrease of cell proliferation and cell migration. Similarly AA predominant variants of FGFR3, TSC2 and RASGRP2 are also shown to be the more aggressive variant.

It is thus discovered by the inventors that alternative splicing variants for genes in the oncogenic signaling pathways, such as PIK3CD, FGFR3, TSC2, FGFR2, PDGFRA, ITGA4, MET, EPHA3, NF1, RASGRP2, CTNNB1, TSC2, ATM, CDK4, and RBI are strong predictors of prostate cancer risk and survival, particularly in the AA patient population. It is thus an aim of the present invention to predict the risk and survival of a patient, by detecting the presence or absence of AA predominant variants of the genes in the oncogenic signaling pathways, particularly for PIK3CD, FGFR3, TSC2, FGFR2, PDGFRA, ITGA4, MET, EPHA3, NF1, RASGRP2, CTNNB1, TSC2, ATM, CDK4, and RBI, and more particularly for PIK3CD, FGFR3, TSC2, RASGRP2, rfGA4, MET, NF1 and BAK1. It is also an aspect of the present invention to utilize relative proportions of splicing variants of a certain gene as a predictor for PCa risk and survival in a patient.

Another aspect of the present invention is directed to isolated polynucleotide sequences of novel splicing variants of PIK3CD, FGFR3, TSC2, RASGRP2, rfGA4, MET, NF1 and BAK1. These novel splicing variants are particularly useful for the detection of the presence or absence of splicing variants in these genes that are in oncogenic signaling pathways. Detection of the presence or absence of splicing variants may be by polymerase chain reaction, by oligonucleotide probes hybridization, particularly high throughput DNA micro array analysis, or high throughput DNA sequencing, or any other means known to one skilled in the art. The isolated novel splicing variants sequences are also useful for targeted silencing of certain splicing variants of these genes. Targeted gene silencing may be by siRNA, miRNA, or other complementary RNA constructs.

Additionally, polypeptide products of the novel splicing variants of the present invention may be analyzed for determining the presence or absence of certain splicing variants. Mass spectrometry may be used to identify peptide fragments specific to certain splicing variants. Antibodies specifically recognize specific amino acid sequences of the novel splicing variants may be developed for the detection of the protein products of these splicing variants. The antibodies may be monoclonal antibodies, polyclonal antibodies, Fab, single chain antibody, or other engineered antibody constructs known to one skilled in the art.

In some embodiments, the present invention teaches a method of classifying a patient for eligibility for cancer therapy, said method comprising a) providing a tissue sample from a patient; b) determining presence or absence of PIK3CD transcript without exon 20 in the sample's total mRNA; and c) classifying the patient as eligible to receive said cancer therapy based on the presence or absence of PIK3CD transcript without exon 20 in the total mRNA of said tissue sample; wherein absence or low levels of PIK3CD transcripts without exon 20 is indicative of said patient's eligibility for cancer therapy.

In some embodiments, the present invention teaches a method of classifying a patient for eligibility for cancer therapy, said method comprising determining the presence or absence of PIK3CD transcript without exon 20 in a cancer sample from said patient and classifying the patient as eligible to receive said cancer therapy based on the presence of absence of the PIK3CD transcripts without exon 20.

In some embodiments, the methods of the present invention further comprise extracting the total mRNA prior to determining the presence of absence of the PIK3CD transcript without exon 20.

In some embodiments, the methods of the present invention further comprise reverse transcribing the total mRNA to cDNA.

In some embodiments, the present invention teaches the detection of the PIK3CD transcript without exon 20 by polymerase chain reaction. In some embodiments, the template for the PCR is cDNA obtained from the patient's tissue sample.

In some embodiments, the present invention teaches the detection of the PIK3CD transcript without exon 20 by hybridization to probes specific to PIK3CD junctions exon 20.

In other embodiments the presence of PIK3CD transcript without exon 20 is determined by detection of PIK3CD and determination of the mRNA/cDNA size. Thus in some embodiments, the present invention teaches the use of generic PIK3CD probes and the separation of the PIK3CD mRNA or cDNA by size (e.g. by acrylamide, or agarose gel).

In some embodiments, the present invention teaches the detection of the PIK3CD transcripts without exon 20 by DNA sequencing. In some embodiments the DNA sequenced is the cDNA from the patient's tissue sample.

In some embodiments, the present invention teaches that the presence of PIK3CD transcript without exon 20 by detecting the presence of any part of the PIK3CD mRNA and determining the size of the mRNA such that exon 20 can be said to be present based on the increased length of the PIK3CD mRNA. In some embodiments, the detection steps may be conducted on cDNA made from said mRNA.

In some embodiments, the present invention teaches cancer therapy with a PI3K inhibitor.

In some embodiments, the PI3K inhibitor of the present invention is CAL101.

In some embodiments, the present invention teaches methods of determining cancer therapy eligibility for prostate cancer or lung cancer.

In some embodiments, the present invention also teaches methods of treating cancer with CAL101.

In some embodiments, the present invention teaches methods of treating a patient with CAL101, wherein said patient's eligibility to receive said CAL101 treatment is determined based on the presence of PIK3CD exon 20 mRNA in said patient's cancerous tissue.

In some embodiments, the present invention teaches a kit for determining the eligibility of patients for P13K inhibitor cancer therapy, said kit comprising an oligonucleotide capable of binding to a region of the PIK3CD mRNA or cDNA, and PIK3CD standards; wherein said kit is capable of detecting the presence of PIK3CD transcript without exon 20.

In some embodiments, the present invention teaches that the kit comprises a first oligonucleotide to detect PIK3CD transcript without exon 20, and a second oligonucleotide to detect all splice variants of the PIK3CD mRNA; wherein said kit is capable of detecting the ratio of long and short variants of PIK3CD.

In some embodiments the present invention teaches that the PIK3CD standards comprise known concentrations of PIK3CD mRNA or cDNA. In other embodiments the PIK3CD standards comprise PIK3CD single stranded or double stranded oligos of known concentrations.

In some embodiments, the present invention teaches a method of screening cancer therapies for efficacy against splicing variants said method comprising: a) measuring proliferation and invasiveness of said cell line after application of a cancer therapy, said measuring conducted by an experimentation means selected from the group consisting of in vitro and mouse xenograft; b) measuring proliferation and invasiveness of said cell line without said application by an experimentation means selected from the group consisting of in vitro and mouse xenograft; c) comparing results of said measuring to results of measuring proliferation and invasiveness for said cell line without application of cancer therapies; and d) classifying said cancer therapies as either efficacious or not efficacious against cells with a particular splice variant based on differences between results of measuring proliferation and invasiveness of the cell line with and without cancer therapy application.

In some embodiments, the present invention teaches the use of a cell line is selected from the group consisting of VCaP, E006AA, and MDA PCa 2b.

In other embodiments, the present invention teaches the use of a cell line is selected from the group consisting of daughter cell lines of VCaP, E006AA, MDA PCa 2b, PZ-HPV-7, CHO, and HEK293 that stably or transiently express said splice variant via genetic modification.

In some embodiments, the present invention teaches methods of screening cancer therapies wherein said splice variant is a variant of PIK3CD that does not comprise exon 8, or does not comprise exon 20, or does not comprise either of exon 8 and exon 20.

In some embodiments, the present invention teaches screening PIK3 inhibitor cancer treatments.

In some embodiments, the present invention teaches screening splicing variants of genes selected from the group consisting of ITGA4, PIK3CD, FGFR3, TSC2, FGFR2, PDGFRA, MET, EPHA3, NFJ, RASGRP3, CTNNBJ, TSC2, ATM, CDK4, and RBI.

DETAILED DESCRIPTION

Figure 1:
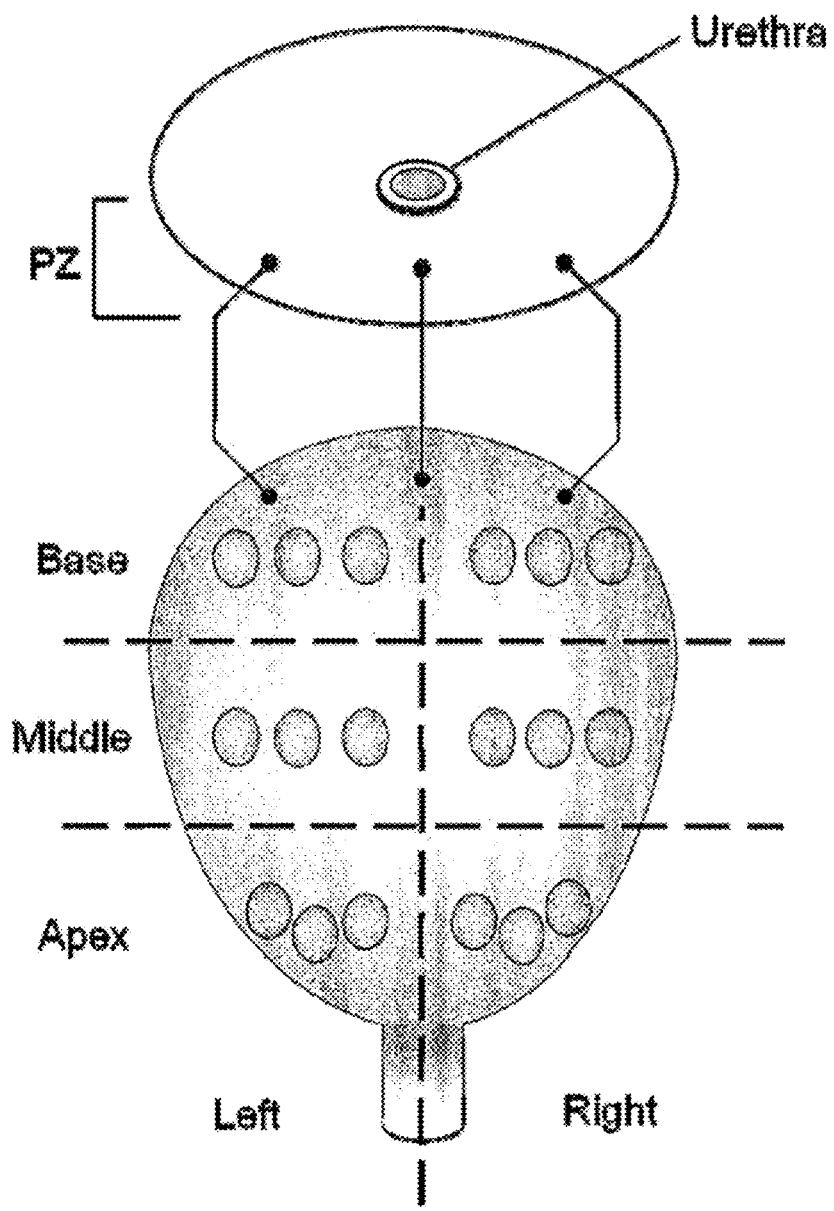
FIG. 1 is a schematic drawing for prostate biopsy core sampling.

Alternative splicing dramatically expands the protein coding repertoire of higher eukaryotes. Current estimates suggest that greater than 60% of all human genes have more than one isoform/splice variant. The expression of specific splice variants is regulated in a developmentally and tissue-specific manner (Black D L: Mechanisms of alternative pre-messenger RNA splicing. Annu Rev Biochem 2003, 72:291-336).

Alternatively spliced isoforms from the same gene can produce proteins with drastically different properties. For example, the bcl-x gene utilizes different 5' splice sites, resulting in proteins that have antagonistic functions. The short form of bcl-x promotes apoptosis, while the long form inhibits cell death (Boise L H, Gonzalez-Garcia M, Postema C E, Ding L, Lindsten T, Turka L A, Mao X, Nunez G, Thompson C B: bcl-x, a bcl-2-related gene that functions as a dominant regulator of apoptotic cell death. Cell 1993, 74:597-608).

Alternative Splicing in Cancers

Cancer cells are able to adapt and evolve by developing mechanisms to escape control by their microenvironment. The diversity and plasticity offered by alternative splicing, therefore, provide an opportunity for cancer cells to produce protein isoforms suitable for tumor growth and/or spreading (David C J and Manley J L. *Genes Dev.* 2010; 24(21):2343-2364). Genome-wide approaches has revealed that large-scale alternative splicing occurs during tumorigenesis (Venables J P et al. *Nat Struct Mol Biol.* 2009; 16(6):670-676.), and the genomic portraits of alternative splicing patterns have proven useful in the classification of tumors (Venables J P. *Bioessays.* 2006; 28(4):378-386; Skotheim R I et al., *Int J Biochem Cell Biol.* 2007; 39(7-8):1432-1449; Omenn G S et al., *Dis Markers.* 2010; 28(4):241-251).

Reports of aberrant splicing events and alterations in ratios of alternatively spliced transcripts in different cancers have been noted, including PCa (Rajan P et al., *Nat Rev Urol.* 2009; 6(8):454-460). These events result in novel transcripts not observed in normal cell counterparts. It has been reported that nearly all areas of tumor biology are affected by alternative splicing, including metabolism, apoptosis, cell cycle control, invasion, metastasis and angiogenesis (Venables J P., *Bioessays.* 2006; 28(4):378-386; Ghigna C et al., *Curr Genomics.* 2008; 9(8):556-570).

One of the earliest examples of alternative splice variants with opposing apoptotic effects is Bcl-x. The Bcl-x pre-mRNA can be alternatively spliced to produce two splice variants, anti-apoptotic Bcl-xL (long form) and pro-apoptotic Bcl-xS (short form) (Boise L H et al. *Cell.* 1993; 74(4):597-608). High Bcl-xL/Bcl-xS ratios, promoting tumor cell survival, can be found in a number of cancer types, including human lymphoma, breast cancer, and human hepatocellular carcinoma (Minn A J et al., *J Biol Chem.* 1996; 271(11):6306-6312.44-46; Olopade O I et al., *Cancer J Sci Am.* 1997; 3(4):230-237; Takehara T et al., *Hepatology.* 2001; 34(1):55-61). Another example of an apoptosis-related gene that undergoes alternative splicing in cancer cells is the Fas receptor gene.

Expressed on the cell surface of many cell types, the Fas receptor is activated by the Fas ligand produced by cytotoxic T cells, which initiates a death-signaling cascade leading to apoptosis of cells expressing the Fas receptor (Bouillet P et al, *Nat Rev Immunol.* 2009; 9(7):514-519). There are at least 3 short mRNA variants of Fas missing the encoded transmembrane domain and the resulting translated protein variants are presumably secreted by cancer cells and act as decoy receptors for the Fas ligand, thus allowing cancer cells to escape from apoptosis (Cheng J et al., *Science.* 1994; 263(5154):1759-1762; Cascino I et al., *Journal of immunology.* 1995; 154(6):2706-2713).

Alternative splicing of the H-Ras oncogene occurs on a previously unknown spliced exon (named as IDX) caused by an intronic mutation in the H-Ras gene (Cohen J B et al., *Cell.* 1989; 58(3):461-472). This mutation of the IDX splice site results in an H-Ras mRNA variant, which is more resistant to the nonsense-mediated mRNA decay (NMD) process, and consequently overexpressed in cancers (Barbier J et al., *Mol Cell Biol.* 2007; 27(20):7315-7333). Alternative splicing also plays a role in promoting invasive and metastatic behavior in cancers. CD44 was among the first genes with splice variants specifically associated with metastasis, where variants containing exons 4-7 (v4-7) and 6-7 (v6-7) were shown to be expressed in a metastasizing pancreatic carcinoma cell line, but not in the corresponding parental tumor (Gunthert U et al., *Cell.* 1991; 65(1):13-24).

Alternative Splicing in PCa

Recent advances in genomic technologies allows for the molecular profiling of PCas, and confirms that differences in the genetic composition of the tumor contribute a great deal to the complexity of this disease (Witte J S. *Nat Rev Genet.* 2009; 10(2):77-82). Notwithstanding an incomplete understanding of the mechanisms underlying aberrant alternative splicing during tumorigenesis, abnormal alternative splicing of several oncogenes and tumor suppressor genes have been identified in PCa. Fusion of the ERG and TMPRSS2 (androgen-regulated transmembrane protease, serine 2) genes is the most common gene fusion in PCa, and extensive alternative splicing of fusion transcripts has been reported (Wang J et al., *Cancer Res.* 2008; 68(20): 8516-8524). Examination of prostate tumors identified TMPRSS2-ERG fusion transcripts with variable inclusion of a 72 base pair exon and other coding sequence variants. In a comparative study of variants ectopically overexpressed in primary prostatic epithelial cells, the variants containing the 72 by exon resulted in greater cell proliferation, invasion, and motility (Wang J et al., *Cancer Res.* 2008; 68(20):8516-8524). Although the clinical significance of the TMPRSS2-ERG translocation on PCa progression is poorly understood, several studies suggest the presence of this gene fusion is a biomarker of risk and correlates with poor clinical outcome (Tomlins S A et al., *Eur Urol.* 2009; 56(2):275-286).

The fibroblast growth factor (FGF) family and their transmembrane receptors (FGFRs) are thought to be of importance in prostate carcinogenesis. Alternative splicing of FGFRs and their ligands is believed to regulate multiple autocrine and paracrine loops that underlie disease progression. Specifically, alternative splicing of FGFR2, resulting in the switching of FGFR2-IIIb for the FGFR2-IIIc variant, is associated with malignant transformation and androgen insensitivity, and is in keeping with the switch from paracrine to autocrine signaling seen with epithelial to mesenchymal transition (EMT) and tumor progression (Sahadevan K et al., *J Pathol.* 2007; 213(1):82-90). Moreover, the high affinity binding between the FGFR2-IIIc isoform and its ligand FGF8b is significantly associated with higher Gleason grade and clinical stage of PCa (Gnanapragasam V J et al., *Br. J Cancer.* 2003; 88(9):1432-1438).

Differentially Spliced Variants

Figure 6:
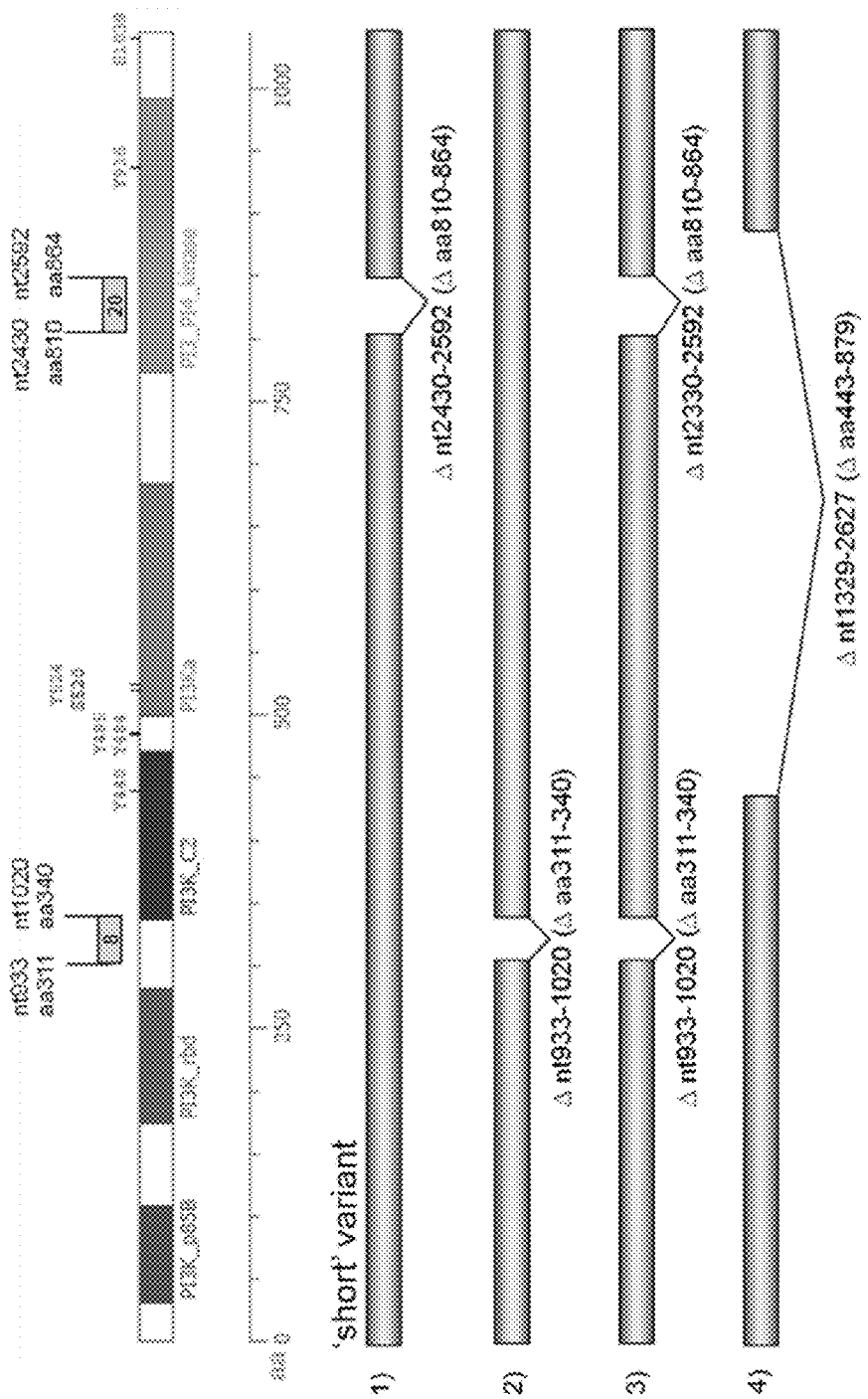
FIG. 6 represents the full length cloning of the L variant, along with three AA S variants and one AA mutant variant of the PIK3CD gene. Of interest is exon 8 (missing in AA variants 2 and 3), which encodes 29 amino acids lying between the Ras-binding domain and C2 domain PIK3CD. Moreover, exon 20 (missing in AA variants 1, 3, 4) encodes a 54 amino acid segment found in the catalytic domain of the enzyme, suggesting that kinase activity of the AA variant protein may differ from the longer 'CA variant'. PIK3CD variant 2 (lacking exon 8) Nucleotide Sequence (3045 nt, SEQ ID No. 7). PIK3CD variant 1 (lacking exon 20) Nucleotide Sequence (2967 nt, SEQ ID No. 11). PIK3CD variant 3 (lacking exon 8 and exon 20) Nucleotide Sequence (2877 nt, SEQ ID No. 14). PIK3CD variant 4 (with large deletion) Nucleotide Sequence (1836 nt, SEQ ID No. 16). PIK3CD variant 4 (with large deletion) Nucleotide Sequence (1836 nt, SEQ ID No. 16).

The present invention is based in part on the inventor's discovery of several cancer-associated genes which are differentially spliced between the AA and CA populations. For example, the inventor discovered four novel PIK3CD variants (FIG. 6), where variant 1 lacks exon 20 (SEQ ID No. 11), which can be shown as the deletion of nt2430-2592 compared to full length PIK3CD cDNA sequence (SEQ ID. No. 1), variant 2 lacks exon 8 (SEQ ID No. 7, deletion of nt931-1020), variant 3 lacks both exon 8 and 20 (SEQ ID No. 14, deletion of nt931-1020 and nt2430-2592), and variant 4 contains a deletion from nt1329-2627 (SEQ ID No. 16). The nucleotide sequence of PIK3CD full length cDNA sequence is shown in SEQ ID No. 1. Exon 8 and exon 20 are marked with double underline and wave underline, respectively. cDNA sequence of variants 1-4 (SEQ ID Nos. 11, 7, 14, and 16) are listed in the FIG. 6 description. Exemplary primers across the junctions of the splicing variants that are useful for detecting the presence of these variants are shown in (SEQ ID Nos. 6, 10, and 15). Exemplary siRNAs for selective knockdown of PIK3CD full length (targeting exon 20, SEQ ID Nos. 4 and 5)) and variants (targeting exon junctions (SEQ ID Nos. 8, 9, 12, and 13) and deletion junction (SEQ ID Nos. 17 and 18)) are listed in sequence listing file.

Primer across the junction between PIK3CD exon 7 and 9 (SEQ ID No. 6). Primer sequences across the junction between PIK3CD exon 19 and 21 (SEQ ID No. 10). Primer sequences across the deleted region (nt1329-2627) of PIK3CD (SEQ ID No. 15).

The inventor also discovered a novel splicing variant of FGFR3 (fibroblast growth factor receptor 3), which lacks exon 14 (SEQ ID No. 19). The nucleotide sequence of FGFR3 full length cDNA sequence is shown in (SEQ ID No. 19). Exon 14 is marked with double underline. Exemplary primer across the junction of splicing variant that is useful for detecting the presence of this variant is shown in (SEQ ID No. 26). Exemplary siRNAs for selective knockdown of FGFR3 full length (targeting exon 14, SEQ ID NOs. 22 and 23)) and variant (targeting exon junction (SEQ ID Nos. 26 and 27) are listed in the sequence listing. In some embodiments the present invention refers to splicing variants of FGFR3. In other embodiments other FGFR splice variants are also relevant to the present disclosure. For example, in some embodiments, the methods, kits, and treatments of the present invention also apply to FGFR2, or another FGFR.

Primer across the junction between FGFR3 exon 13 and 15 (SEQ ID No. 24). FGFR3 variant 1 (lacking exon 14} Nucleotide Sequence (2298 nt, SEQ ID No. 25).

The inventor also discovered a novel splicing variant of TSC2 (tuberous sclerosis 2), which lacks exon 19 (SEQ ID No. 34). The nucleotide sequence of TSC2 full length cDNA sequence is shown in (SEQ ID No. 28). Exon 19 is marked with double underline. Exemplary primer across the junction of splicing variant that is useful for detecting the presence of this variant is shown in (SEQ ID No. 33).

Exemplary siRNAs for selective knockdown of TSC2 full length (targeting exon 19, SEQ ID NOs. 31 and 32)) and variant (targeting exon junction (SEQ ID Nos. 35 and 36) are listed in the sequence listing file.

The inventor also discovered two novel splicing variants of RASGRP2 (RAS guanyl-releasing protein 2), which lacks exon 10 (SEQ ID No. 45) or exon 11 (SEQ ID No. 49). The nucleotide sequence of RASGRP2 full length cDNA sequence is shown in (SEQ ID No. 37). Exon 10 is marked with double underline, and exon 11 is marked with wave underline. Exemplary primers across the junctions of the splicing variants that are useful for detecting the presence of these variants are shown in (SEQ ID Nos. 44 and 48). Exemplary siRNAs for selective knockdown RASGRP2 full length (targeting exon 10, SEQ ID NOs. 40 and 41, targeting exon 11, SEQ ID NOs. 42 and 43)) and variants (targeting exon junctions (SEQ ID Nos. 46, 47, 50, and 51)) are listed in the sequence listing file.

The inventor also discovered a novel splicing variant of ITGA4 (integrin a4), which lacks exon 23 (SEQ ID No. 58). The nucleotide sequence of ITGA4 full length cDNA sequence is shown in (SEQ ID No. 52). Exon 23 is marked with double underline. Exemplary primer across the junction of splicing variant that is useful for detecting the presence of this variant is shown in (SEQ ID No. 57).

Exemplary siRNAs for selective knockdown of ITGA4 full length (targeting exon 23, SEQ ID NOs. 55 and 56)) and variant (targeting exon junction (SEQ ID Nos. 59 and 60)) are listed in the sequence listing.

The inventor also discovered a novel splicing variant of MET (MNNG HOS Transforming gene), which include the insertion of non-coding exon 27 (SEQ ID No. 65). The nucleotide sequence of MET full length cDNA sequence is shown in (SEQ ID No. 62). Exon 27 is marked with double underline. Exemplary primer across junctions of full length variant is shown in (SEQ ID No. 61). Exemplary siRNAs for selective knockdown of MET full length (targeting exon junction 26 and 28 (SEQ ID Nos. 63 and 64) and variant (targeting exon 27 (SEQ ID Nos. 68 and 69)) are listed in the sequence listing.

The inventor also discovered a novel splicing variant of NF1 (Neurofibromin 1), which lacks exon 8 (SEQ ID No. 76). The nucleotide sequence of NF1 full length cDNA sequence is shown in (SEQ ID No. 70). Exon 8 is marked with double underline. Exemplary primer across the junction of splicing variant that is useful for detecting the presence of this variant is shown in (SEQ ID No. 75).

Exemplary siRNAs for selective knockdown of NF1 full length (targeting exon 8, SEQ ID NOs. 73 and 74) and variant (targeting exon junction (SEQ ID Nos. 77 and 78)) are listed in the sequence listing.

The inventor also discovered a novel splicing variant of BAK1 (Bcl-2homologous antagonist/killer), which lacks exon 2 (SEQ ID No. 85). The nucleotide sequence of BAK1 full length cDNA sequence is shown in (SEQ ID No. 79). Exon 2 is marked with double underline. Exemplary primer across the junction of splicing variant that is useful for detecting the presence of this variant is shown in (SEQ ID No. 84). Exemplary siRNAs for selective knockdown of BAK1 full length (targeting exon 2, SEQ ID NOs. 82 and 83) and variant (targeting exon junction (SEQ ID Nos. 86 and 87) are listed in the sequence listing.

For example, in some embodiments, the methods, kits, and treatments of the present invention apply to any of the splice variants described herein.

Patient Selection

In some embodiments, the present invention teaches methods of determining the eligibility of patients for cancer therapy. In some embodiments, the present invention teaches methods of patient pre-screening or population selection. For example, in some embodiments the methods of the present invention are conducted on African American patients, or other patients from African descent which are likely to have the splice variants taught herein. In some embodiments, the populations of the present invention can be further narrowed to patients who have already been diagnosed with cancer. In some embodiments the present invention focuses on patients who have been diagnosed with prostate or lung cancer. For example in some embodiments the population of the present invention comprises patients that fulfill the following criteria: serum PSA level>7 ng/ml, or PSA level>4 ng/ml in in conjunction with an abnormal digital rectal exam. In other embodiments, the present invention is also applicable to patients already undergoing a cancer treatment.

Tissue Sampling

In some embodiments, the present invention teaches methods of detecting PIK3CD or FGFR3 splicing variants in patient tissue. In some embodiments patient tissue can be blood, urine, serum, body fluid, or cells. In some embodiments the tissue cells are cancerous cells. In other embodiments the cells can be obtained through biopsies of the cancerous area. For example, in some embodiments, the present invention teaches methods of taking a biopsy from a prostate.

In some embodiments the present invention teaches taking biopsies from a prostate area selected from the right-base, left-base, right-mid, left-mid, right-apex, left-apex, right-transition, and left-transition zones. A schematic for 18 core biopsy is shown in FIG. 1.

Kits of the Present Invention

In some embodiments, the present invention also includes kits for determining a patient's eligibility for a cancer treatment. In some embodiments, the kits of the present invention include a reagent for measuring at least one splice variant identified in this application. As used herein, the term "reagent" refers to the materials necessary to conduct any of the detection assays described in this application. That is, in some embodiments, kits for determining a patient's eligibility for a cancer treatment can include reagents for performing PCR, RT-PCR, qPCR, qRT-PCR, Northern blots, Southern Blots, Western blots, ELISAs, DNA sequencing, gene chip analysis, RNA seq, microarrays, immunoblots, immunoassays, electrophoresis, or other known methods for detecting RNA, DNA, or protein.

In some embodiments the kit for determining patient eligibility comprises an oligonucleotide capable of binding to a portion of the PIK3CD or FGFR mRNA or DNA. In some embodiments, the kit further comprises PIK3CD or FGFR3 splice variant standards. For example, in some embodiments, the kit may comprise PCR primers capable of distinguishing between PIK3CD or FGFR3 mRNA or cDNA with or without exon 20. In some embodiments, the PCR primers are further designed so that they can distinguish between cDNA and genomic DNA, such that in some embodiments, mRNA purification is not necessary. In other embodiments, the kit can comprise generic primers which can copy PIK3CD or FGFR3 mRNA/cDNA with or without exon 20. Thus in some embodiments, the kit can include reagents necessary to distinguish between different size PCR products such materials to conduct electrophoresis, capillary, or other form of size exclusion separation. In some embodiments the kit of the present invention can include reagents necessary for qPCR such as probes designed to detect PIK3CD or FGFR3 splice variants, or generic dsDNA detection reagents such as EtBr or Sybr Green.

In some embodiments the kit for determining patient eligibility comprises an oligonucleotide capable of hybridizing to a selected portion of the PIK3CD or FGFR3 mRNA or DNA. For example, in some embodiments, the kit can comprise a probe capable of detecting exon 20 or the junction of PIK3CD without exon 20. In other embodiments the probe will be able to target another part of the PIK3CD or FGFR3 mRNA or DNA. In some embodiments the probes of the present invention are labeled for detection. For example, in some embodiments the probes of the present invention are labeled with metals or other antigens (e.g., gold, silver, copper, platinum, cadmium, composite nanoparticle, or peptide antigens), fluorescent markers (e.g., fluorescein, Texas-Red, green fluorescent protein, yellow fluorescent protein, cyan fluorescent protein, Alexa dye molecules, etc.), radio isotopes (e.g., P32 or other ligated radiolabels) or enzyme labels (e.g., alkaline phosphatase, horseradish peroxidase, beta-galactosidase, beta-lactamase, galactose oxidase, lactoperoxidase, luciferase, myeloperoxidase, and amylase). In some embodiments the kit of the present invention includes two or more probes with different labels such that the ratio of splice variants can be determined by comparing the signal of two labels.

In some embodiments the kit includes labels for the mRNA or cDNA from the sample. In some embodiments the probes of the kit are immobilized on a chip or other surface. Thus in some embodiments the kit hybridizes the different splice variants onto a surface which can be read to quantify the absolute and relative values of the PIK3CD variant with or without exon 20. In some embodiments, the kit of the present invention also includes probes for a control gene which can be used to normalize PIK3CD or FGFR3 signal. In other embodiments the kit comprises PIK3CD standards. In some embodiments the PIK3CD or FGFR3 standards are mRNA or cDNA portions or whole sections of PIK3CD or FGFR3 splice variants at known concentrations. In some embodiments the PIK3CD standards are labeled with the same or different detectable labels as the sample mRNA or cDNA.

In other embodiments the kit includes antibodies against PIK3CD or FGFR3 proteins. In some embodiments the antibodies will distinguish between PIK3CD or FGFR3 proteins encoded in the splice variants which are indicative of a patient's eligibility for a cancer treatment.

In some embodiments, the kit will require the additional use of standard laboratory tools or machinery. In some embodiments, necessary tools include pipettes, cell sorting machines, plate readers, centrifuges etc. are known to those having skilled in the art. In some embodiments, use of the kit may require additional standard laboratory reagents such as pipette tips, membranes, buffers, or chemicals as are well known by those having skilled in the art.

Prostate Cancer Cell Lines for Validation

In some embodiments the present invention teaches the use of prostate cancer (PCa) cell lines to study and validate the effects of differential splicing of the identified cancer genes. In some embodiments the present invention teaches cell lines including, but not limited to: i) AA PCa lines MDA-PCa2b (bone metastasis), E006AA (localized PCa), RC77T/E and RC43T/E, ii) AA prostate benign lines RC165N/h, RC77N/E and RC43N/E, iii) CA PCa lines RC92a/h (primary PCa Gleason score 3+3), RC58T/h/SA#4 (primary PCa Gleason 3+4), PC-3 (bone metastasis), VCaP (bone metastasis), LNCaP (lymph node metastasis), and iv) CA prostate benign line RC170N/h 103-108.

PCR Detection

The present invention provides a method of identifying splicing variants of genes associated with prostate cancer risk and survival. In some embodiments, the method generally comprises detecting the splicing variants in a nucleic acid sample from an individual, such as a prostate biopsy specimen. In some embodiments, total RNA is extracted from the specimen, cDNA is synthesized from the extracted RNA and subject to further analysis. Nucleic acid samples used in the methods and assays of the present invention may be prepared by any available method or process. In other embodiments, tissue can be directly lysed and used in RT PCR detection of differential splicing.

Detection of splicing variants may be accomplished by amplifying specific fragments directly from a cDNA preparation from the tumor tissue using PCR. Presence of certain PCR product can be indicative of the presence of certain splicing variants, when the primers for the PCR are designed in such way that PCR products are only available when certain variants are present in the sample. Alternatively, primers may be designed to produce easily differentiable products for different variants. The sequence composition of the variants may also be determined from the amplified product.

The PCR reaction is well known in the art (See, e.g., U.S. Pat. Nos. 4,683,203; and 4,683,195). In some embodiments, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. The primers are prepared using any suitable method, such as conventional phosphotriester or phosphodiester methods or automated embodiments thereof (Beaucage, Tet. Lett. 22: 1859-1862, 1981).

For the detection of splicing variants, primers may be designed to flank a certain exon that may be alternatively spliced, i.e., one primer is complementary to the 5' side of the exon, and the other primer is complementary to the 3' side of the exon. The PCR amplification products thus would show different sizes. When the exon is present, a larger amplification product is obtained. When the exon is absent, a smaller amplification product is obtained. Alternatively, a primer may be designed to be complementary to a nucleotide sequence within the exon. This way, PCR amplification product is only available when the exon is present in the specimen. Additionally, a primer may be designed to be partially complementary to the 3' end of an exon 5' to the alternatively spliced exon, and partially complementary to the 5' end of an exon 3' to the alternatively spliced exon. PCR amplification product can only be obtained when the alternatively spliced exon is present in the sample.

The polymerization agent can be any compound or system (including enzymes) which will facilitate combination of the nucleotides in the proper manner to form the primer extension products which are complementary to each nucleic acid strand. Other fundamental conditions to allow amplification include the presence of nucleoside triphosphates and suitable temperature and pH (Thigpen et al., J. Clin. Invest. 90: 799-809, 1992; Saiki et al., Science 239: 487-491, 1988).

DNA sequences of the specified gene which have been amplified by use of polymerase chain reaction may also be screened using exon oligonucleotide probes.

These probes are nucleic acid oligomers, each of which are complementary to a corresponding segment of the investigated gene and may or may not contain a known variant. The assay is performed by detecting the presence or absence of a hybridization signal for the specific sequence.

Hybridization Probes

Another aspect of the subject invention is to provide for variant specific nucleic acid hybridization probes capable of detecting splicing variants of genes which predispose an individual to prostate cancer, or alternative can determine which cancer treatment would be most effective. The hybridization probes of the subject invention may be derived from the disclosed nucleotide sequences of the identified variants and form stable hybrids with the target sequences, under stringent to moderately stringent hybridization and wash conditions. Stringent conditions will be used in the case of perfect complementation with the target sequence, less stringent hybridization conditions will be used if mismatches are expected among the variants. Conditions will always be chosen such that nonspecific/adventitious bindings are eliminated or minimized. The probes may be of any suitable length, which span all or a portion of the specified gene region, and which allow specific hybridization.

Nucleic acid hybridization simply involves contacting a probe and target nucleic acid (from a nucleic acid sample) under conditions where the probe and its complementary target can form stable hybrid duplexes through complementary base pairing (see U.S. Pat. No. 6,333,155). Methods of nucleic acid hybridization are well known in the art. In a preferred embodiment, the probes are immobilized on solid supports such as beads, microarrays, or gene chips.

The probes include an isolated polynucleotide, preferably attached to a label or reporter molecule, may be used to isolate other polynucleotide sequences, having sequence similarity by standard methods. Techniques for preparing and labeling probes are known in the art and disclosed in Sambrook et al. (Molecular Cloning: A Laboratory Manual, Ed. 2; Cold Spring Harbor, N.Y.: Cold Spring Harbor Laboratory, 1989) or Ausubel et al. (Current Protocols in Molecular Biology, Wiley & Sons, New York, N.Y., 1995). The labels may be incorporated by any of a number of means well known to those of skill in the art (see U.S. Pat. No. 6,333,155). Commonly employed labels include, but are not limited to, biotin, fluorescent molecules, radioactive molecules, chromogenic substrates, chemiluminescent labels, enzymes, and the like. The methods for biotinylating nucleic acids are well known in the art, as are methods for introducing fluorescent molecules and radioactive molecules into oligonucleotides and nucleotides.

Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like (Verma et al., Human Chromosomes: A Manual of Basic Techniques, Pergamon Press, New York N.Y., 1988).

To detect the presence of the splicing variants of genes predisposing an individual to prostate cancer, a test sample is prepared and analyzed for the presence or absence of such susceptibility alleles. Thus, the present invention provides methods to identify the expression of one of the nucleic acids of the present invention, or homolog thereof, in a test sample, using a nucleic acid probe or antibodies of the present invention. In particular, such methods comprise incubating a test sample with one or more of oligonucleotide probes of the present invention (as described above) and assaying for binding of the nucleic acid probes or antibodies to components within the test sample.

Conditions for incubating a nucleic acid probe or antibody with a test sample depend on the format employed in the assay, the detection methods used, and the type and nature of the probe used in the assay. One skilled in the art will recognize that any one of the commonly available hybridization or amplification formats can readily be adapted to employ the nucleic acid probes or antibodies of the present invention.

Examples of such assays can be found in Chard, An Introduction to Radioimmunoassay and Related Techniques, Elsevier Science Publishers, Amsterdam, Netherlands, 1986; Bullock et al., Techniques in Immunocytochemistry, Academic Press, Orlando, Fla. Vol. 1, 1982, Vol. 2, 1983, Vol. 3, 1985; Tijssen, Practice and Theory of Immunoassays: Laboratory Techniques in Biochemistry and Molecular Biology, Elsevier Science Publishers, Amsterdam, Netherlands, 1985.

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing DNA extracts from any of the above samples are well known in the art and can be readily be adapted in order to obtain a sample which is compatible with the system utilized.

Protein Detection

In some embodiments, the present invention teaches the detection of the proteins which are produced from differentially spliced genes. In some aspects of the invention, a new antibody can be generated from the protein or a fragment of any of the differentially spliced genes. For example, in some embodiments, antibodies targeting the protein domains encoded by exons which are spliced out of short forms can be used to detect the long versions of the proteins while other antibodies could be used to detect both versions and allow for signal subtraction. In other embodiments antibodies targeting both versions of the differentially spliced genes which would be separated by size, charge, or other distinguishing feature to quantify the levels of the S and L forms. In yet other embodiments, the differential accumulation of S or L forms of a protein could be detected via purification by using antibodies binding one or another version and the eluting the purified protein.

In some embodiments commercially available antibodies may be used. In other embodiments, the present invention teaches methods of producing new antibodies. One skilled in the art will recognize that many procedures are available for the production of antibodies, for example, the methods described in (Harlow et al 1988). In some embodiments, the differentially spliced immunogen used to create the antibodies will include the post translational modifications of the native protein (e.g. folding). In some embodiments, the differentially spliced immunogens are obtained from human or other mammalian cells such as transformed murine NS0, wild type DU-145, or other differentially spliced protein expressing cell line (natural or artificial). In some embodiments the differentially spliced antigen can be cells expressing the differentially spliced protein. One skilled in the art will also appreciate that binding fragments or Fab fragments can be prepared from genetic information by various well-known procedures such as those described in (Borrebaeck et al., 1995; and U.S. Pat. No. 7,960,517).

In another embodiment of the present invention, polyclonal antibodies targeting differentially spliced proteins may be created for the detection of differential splicing. Various procedures known in the art may be used for the production of polyclonal antibodies to the differentially spliced protein or a fragment of the differentially spliced protein. In one embodiment of the invention, the differentially spliced protein or fragment thereof may be injected into a host animal. In some embodiments the host animals can include but are not limited to rabbits, mice, rats, etc. In some embodiments the resulting sera is purified and tested for its ability to react with the differentially spliced protein via techniques well known in the art such as westerns, ELISAs, immunofluorescence screens, flow cytometry, Fluorescence Activated Cell Sorting (FACS) or others.

In another embodiment, monoclonal antibodies (mAbs) directed against the differentially spliced protein may be created for the detection of said splicing variant and determination of treatment. In one embodiment, differentially spliced protein antibodies are created via the hybridoma technique (Kohler and Milstein 1975), or other techniques (Cole et al., 1985; or U.S. Pat. No. 6,116,013). For more details and examples on antibody production see U.S. Pat. No. 7,985,560. In other embodiments aptamers are designed to detect the differentially spliced protein of interest.

In some embodiments the PIK3CD S splice variant does not contain exon 20, whereas the PIK3CD L variant does contain exon 20. In some embodiments the present invention teaches that a patient is eligible for cancer treatment if the ratio of PIK3CD (S:L) is less than 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:25, 1:30, 1:35, 1:40, 1:45, 1:50, 1:55, 1:60, 1:65, 1:70, 1:75, 1:80, 1:85, 1:90, 1:95, 1:100, 1:110, 1:120, 1:130, 1:140, 1:150, 1:160, 1:170, 1:180, 1:190, 1:200, 1:210, 1:220, 1:230, 1:240, 1:250, 1:260, 1:270, 1:280, 1:290, 1:300, 1:310, 1:320, 1:330, 1:340, 1:350, 1:360, 1:370, 1:380, 1:390, 1:400, 1:500, 1:600, 1:700, 1:800, 1:900, 1:1000, 1:1100, 1:1200, 1:1300, 1:1400, 1:1500, 1:1600, 1:1700, 1:1800, 1:1900, 1:2000, 1:2100, 1:2200, 1:2300, 1:2400, 1:2500, 1:2600, 1:2700, 1:2800, 1:2900, 1:3000, 1:3100, 1:3200, 1:3300, 1:3400, 1:3500, 1:3600, 1:3700, 1:3800, 1:3900, 1:4000, 1:4100, 1:4200, 1:4300, 1:4400, 1:4500, 1:4600, 1:4700, 1:4800, 1:4900, or 1:5000.

Thus, in some embodiments the present invention teaches that a patient is eligible for cancer treatment if the ratio of PIK3CD (S/L) is less than 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10.

Gene Silencing

In some embodiments, the present invention teaches the silencing of aggressive splice variant genes. In some embodiments the silencing of the aggressive or less desirable variant can reduce the tumor growth rate, mobility rate, or other pathology associated with the tumor or cancerous cells. In other embodiments, the silencing of a less-desirable variant can improve the effectiveness of a cancer treatment (such as the response to a small molecule, chemotherapy, or radiation treatment).

In some embodiments, the present invention teaches the knockdown of oncogene splice variant pairs (e.g. AA-specific variant versus CA-counterpart variant knockdown) in AA and CA PCa patients. In some embodiments, the present invention teaches that knocking down the AA-specific variant lead to a greater abrogation in oncogenic behavior compared to knocking down the CA-counterpart. In other embodiments, the present invention teaches modulating the AA-variant/CA-variant ratio either up or down lead to increase the effectiveness of cancer treatment, or reduce the aggressiveness of a specific cancer. The present invention teaches proper siRNA design parameters (seed sequence, siRNA duplex strand bias of Gibbs free energy, BLAST search against Ensembl for target specificity 111) and standard computational protocols for its implementation (Irby R B et al., *Cancer Res.* 2005; 65(5):1814-1821; Healy Z R et al, *Proc Natl Acad Sci USA.* 2005; 102(39):14010-14015; Teramoto H et al., *Oncogene.* 2005; 24(3):489-501).

In some embodiments, the present invention teaches achieving variant specificity by carefully designing siRNAs that target the exon retained in 'variant 1' but missing in 'variant 2', and 'splice junction siRNAs' that specifically target the splice junction resulting from the missing exon in 'variant 2'.

The phrase "gene silencing" refers to a process by which the expression of a specific gene product is lessened or attenuated. It is also used interchangeably with the term "gene knockdown." Gene silencing can take place by a variety of pathways. Unless specified otherwise, as used herein, gene silencing refers to decreases in gene product expression that results from RNA interference (RNAi), a defined, though partially characterized pathway whereby small inhibitory RNA (siRNA) act in concert with host proteins (e.g. the RNA induced silencing complex, RISC) to degrade messenger RNA (mRNA) in a sequence-dependent fashion. The level of gene silencing can be measured by a variety of means, including, but not limited to, measurement of transcript levels by Northern Blot Analysis, B-DNA techniques, transcription-sensitive reporter constructs, expression profiling (e.g. DNA chips), and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g. GFP) or enzymatic activity (e.g. alkaline phosphatases), or several other procedures.

The term "siRNA" refers to small inhibitory RNA duplexes that induce the RNA interference (RNAi) pathway. These molecules can vary in length (generally between 18-30 basepairs) and contain varying degrees of complementation to their target mRNA in the antisense strand. Some, but not all, siRNAs have unpaired overhanging bases on the 5 or 3' end of the sense strand and/or the antisense strand. The term "siRNA" includes duplexes of two separate strands, as well as single strands that can form hairpin structures comprising a duplex region. Designing a siRNA molecule that can specifically silence a certain gene is well known in the art, and can be routinely carried out using methods similar to what is disclosed in U.S. Pat. No. 8,008,474, which is incorporated herein by reference. siRNA can be routinely introduced to cells through conventional means such as transfection.

For targeted silencing of certain splicing variant, siRNA can be designed to target a specific exon that is only present in one variant. The mRNA of the variant that include this exon will be selectively silenced. Alternatively, siRNA can be designed to target a specific exon junction, which will only exist when certain splicing event occurs. In other words, siRNA can be designed to target the junction sequence of an exon immediately 5' to the alternatively spliced exon and an exon that is immediately 3' to the alternatively spliced exon. This particular junction sequence would only exist in a continuous polynucleotide sequence within an mRNA when the alternatively spliced exon is lacking.

Vectors and Transformation

In some embodiments, the present invention teaches methods and compositions of vectors, constructs, and nucleic acid sequences encoding for the gene splicing variants, or RNAi complexes of the present invention. In some embodiments, the present invention teaches plasmids for transgenic or transient expression of the PIK3CD S and L variants. In some embodiments, the present invention teaches plasmids for transgenic or transient expression of the FGFR3 S and L variants. In some embodiments the present invention teaches a plasmid encoding RNAi triggers against specific PIK3CD or FGFR3 variants.

In other embodiments, the plasmids of the present invention are tailored to the organism being transformed. In some embodiments, the sequences of the present invention will be codon-optimized to express in humans. Persons having skill in the art will recognize the importance of using promoters providing adequate expression. In some embodiments, the plasmids and vectors of the present invention are selectively expressed in the cells of interest. In some embodiments, the present invention teaches the use of promoters designed to express in the prostate. In other embodiments the present invention teaches the use of constitutive promoters. Thus in some embodiments, the present application teaches the use of ectopic promoters, tissue-specific promoters, developmentally-regulated promoters, or inducible promoters. In some embodiments, the present invention also teaches the use of terminator sequences.

In some embodiments, the present invention teaches the use of transformation of the plasmids and vectors disclosed herein. Persons having skill in the art will recognize that the plasmids of the present invention can be transformed into cells through any known system. For example, in some embodiments, the present invention teaches transformation by particle bombardment, chemical transformation, nano-spike transformation, or virus particle transformations.

CAL101

CAL101 is a potent and selective PI3Kδ inhibitor that promotes cell death in B-cells and primary cells with cancerous malignancies including chronic lymphocytic leukemia, mantle cell lymphoma, and various myeloma (Lannutti B J et al., Blood 2011; 117(2):591-594). CAL101 inhibits CD40, TNF alpha Fibronected signaling which leads to Aid activation. Other exemplary PI3 kinases are disclosed in U.S. Pat. No. 6,608,053, and include BEZ235, BGT226, BKM120, CAL101, CAL263, demethoxyviridin, GDC-0941, GSK615, IC87114, LY294002, Palomid 529, perifosine, PF-04691502, PX-866, SAR245408, SAR245409, SF1126, Wortmannin, XL147 and XL765. In some embodiments, the present invention teaches methods of determining whether patients would be candidates for PI3 kinase anti-cancer treatments. In some embodiments, the present invention teaches methods of determining whether patients would be candidates for CAL101 treatments. In other embodiments, the present invention teaches methods of improving tissue's ability to respond to PI3K or CAL101 treatments.

In some embodiments the present invention also teaches treatments with PD173074. In some embodiments the present invention teaches the use of PD173074 with FGFR3 splice variants. In some embodiments the present invention teaches endometrial cancer.

Gleason Scoring

In some embodiments, the present invention teaches methods of scoring cancers/tumors. One described plurality of classes corresponds to the Gleason scoring system. As known in the pertinent art, Gleason scoring assesses the histologic pattern of the prostate cancer. Conventional Gleason scoring consists of two assessments—a primary (dominant) and secondary (non-dominant) grade, and both range from 1 (generally good prognosis), to 5 (generally bad prognosis). In conventional Gleason scoring, the two measurements are combined into a Gleason score which ranges from 2-10, with 2 having the best prognosis and 10 having the worst prognosis.

BRDU Labeling

In some embodiments, the present invention teaches the measurement of cell proliferation via the detection of 5-bromo-2'deoxyuridine (BrdU). The presence of BrdU in cell cultures can cause the BrdU molecule to be incorporated into the newly synthesized DNA of replicating cells (during the S phase of the cell cycle). The BrdU molecule substitutes for thymidine during DNA replication, and gets passed on from generation to generation. The greater the cell proliferation, the greater then amount of BrdU that will be incorporated into the DNA of dividing cells.

In some embodiments, antibodies specific for BrdU can then be used to detect the incorporated chemical to indicate the level of cell division/DNA replication occurring in the cell culture. In some embodiments, binding of the antibody requires denaturation of the DNA, usually by exposing the cells to acid or heat.

In other embodiments, a fluorescent counterstain, propidium iodide (PI), is included to measure the total DNA content. Using two-color, flow cytometric analysis, cells containing incorporated BrdU are readily detected and their cell cycle position is easily assessed.

Another method for detecting BrdU-substituted DNA uses the A-T base binding fluorochrome, Hoechst 33258, that is quenched when bound to A-BrdU regions in double-stranded DNA. This effect is described in Samuel A. Latt, Proc. Nat. Acad. Sci. USA 70 No. 12, p. 3395-3399 (December 1973). The BrdU/Hoechst fluorescence quenching technique, however, is not as sensitive as the immunofluorescent assay.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

Tumorigenesis Assays

In some embodiments, the present invention teaches methods of screening cancer treatments against the splice variant genes of the present application. In some embodiments methods for determining tumorigenesis genesis include assays for migration, proliferation, differentiation, and structural rearrangement.

In some embodiments, the present invention teaches proliferation assays which measure cell number or cell-cycle kinetics. In some embodiments, the present invention teaches cell proliferation assays including haemocytometer or electronic cell counts of cultures; MTT, DNA synthesis via thymine incorporation, or DNA binding dyes, and flow cytometric analysis.

In some embodiments the present invention teaches cell migration assays including Modified Boyden chamber assays, computer scanning of haematoxylin and eosin-stained cells, phagokinetic track, or "wound healing" assays.

In some embodiments the present invention teaches cell differentiation assays including 3d gel, co-culture, matrix assays such as Matrigel, growth factor-reduced Matrigel.

In some embodiments the present invention teaches organ culture, sponge implants, matrigel plug, CAM assay, and chamber assays.

EXAMPLES

Example 1—Collection and Characterization of Clinical Specimens

All patients enrolled into this study fulfilled the following criteria: 1) serum PSA level>7 ng/ml, or PSA level>4 ng/ml in in conjunction with an abnormal digital rectal exam, 2) chemo- and radiation-naïve prior to collecting PCa needle biopsy cores (e.g. no cytotoxic chemotherapy, no androgen deprivation therapy/finasteride-free/no androgen receptor inhibitors, etc.), and 3) no prior history of cancer presentation.

Needle biopsy cores were collected by GWU Medical Faculty Associates urologists from right-base, left-base, right-mid, left-mid, right-apex, left-apex, right-transition, and left-transition zones of the prostate gland of individual patients presenting with high serum levels (>7 ng/ml) of prostate specific antigen (PSA). A schematic for 18 core biopsy is shown in FIG. 1. Collected cores were immediately examined by a board certified PCa pathologist. PCa cores were determined to have a pathologic tumor stage of 2, and Gleason scores ranging from 6-9. There was no significant difference between the two racial groups (AA versus CA) with respect to age and tumor grade.

Paired normal biopsy cores were also available from the same patients for genomic analysis (normal cores typically 1-2 cm away from cancer cores and deemed cancer free by pathologists). Each core contains sufficient RNA material for Affymetrix Human Exon 1.0 ST GeneChip profiling (i.e. 1 µg total RNA).

Example 2—Exon Expression Profiling of AA and CA PCa and Normal Specimens

Total RNA was isolated from PCa and paired normal prostate cores. Exon profiling was performed on the Affymetrix Human Exon 1.0 ST GeneChip. The GeneChip represents an optimal platform for both expression profiling and splice variant detection (Kwan T, Benovoy D, Dias C, Gurd S, Provencher C, Beaulieu P, Hudson T J, Sladek R, Majewski J: Genome-wide analysis of transcript isoform variation in humans. Nat Genet 2008, 40:225-231; Network TCGAR: Comprehensive genomic characterization defines human glioblastoma genes and core pathways. Nature 2008, 455: 1061-1068), as exon level annotations are derived from empirically determined, highly curated mRNA sequences and ab-initio computational predictions.

The GeneChip contains approximately 5.4 million 5-µm features (probes) grouped into 1.4 million probe sets interrogating over one million exon clusters. A 4-way statistical design (t-test with 10% false discovery rate (FDR) for multiple test correction) was employed to identify differentially expressed exons (corresponding to differentially expressed splice variants) in the following comparisons: AA normal vs. CA normal, AA cancer vs. CA cancer, AA cancer vs. AA normal, and CA cancer vs. CA normal.

Figure 2:
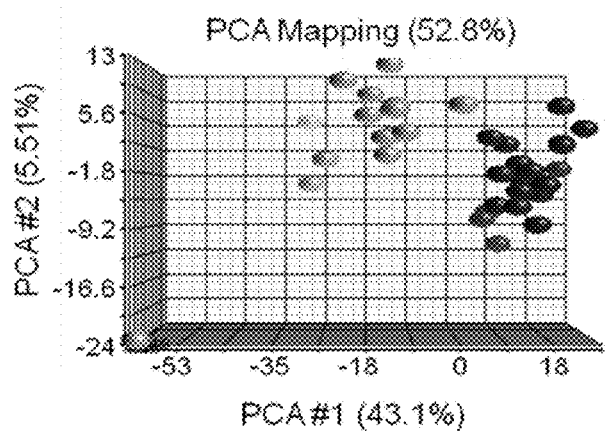
FIG. 2 shows differentially expressed exons between AA and CA populations. (A) Depicts a Principal Component Analysis (PCA), showing good separation of the two racial populations based on their exon suppression profiles. (B) Depicts the unsupervised hierarchical clustering of patient samples into racial populations based on 934 differentially expressed exons.
Figure 2:
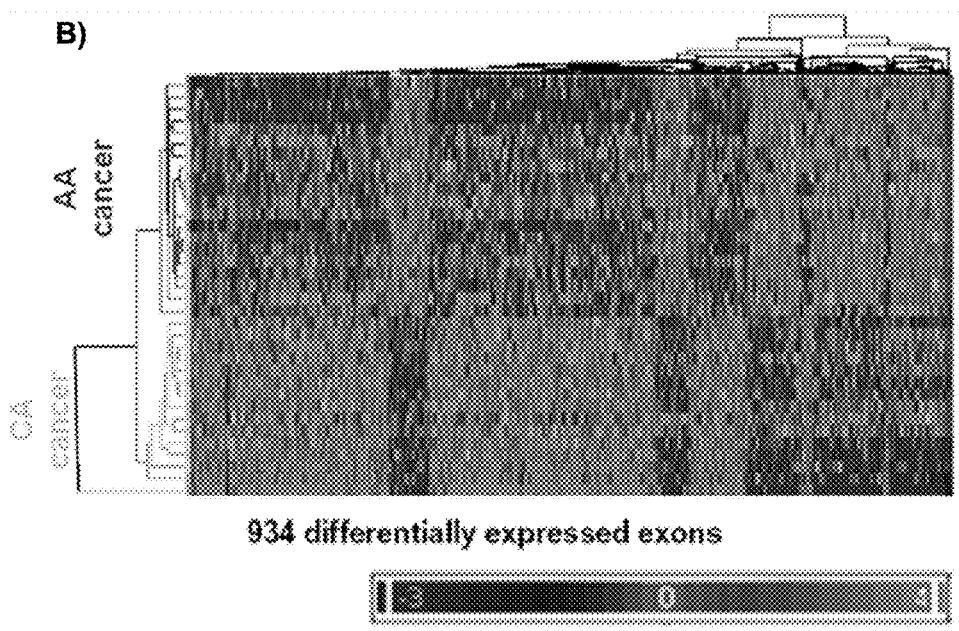

The inventor through exon level analysis has identified 861 genes (e.g. PIK3CD, FGFR3, TSC2, RASGRP2, rfGA4, MET, NF1 and BAK1) exhibiting differential splicing patterns between the AA and CA populations. Differentially expressed exons between AA and CA populations are shown in FIG. 2. FIG. 2(A) shows Principle Component Analysis (PCA) plots and clustering analysis of differentially expressed exons between AA and CA PCa specimens. 20 AA and 15 CA PCa specimens were analyzed for global alternative splicing patterns (i.e. differentially expressed exons) using the Affymetrix human Exon 1.0 ST arrays. These splice variants represent candidate markers mediating PCa disparities.

An example of a gene exhibiting population-specific splicing is integrin a4 (ITGA4) which has been postulated to be a metastasis suppressor, since blocking its activity with antisense RNA enhances oral squamous carcinoma cell motility (Zhang Y, Lu H, Dazin P, Kapila Y: Functional differences between integrin alpha4 and integrins alpha5/alphaV in modulating the motility of human oral squamous carcinoma cells in response to the V region and heparin-binding domain of fibronectin. Exp Cell Res 2004, 295:48-58.).

Example 3—qRTPCR Validation of Splice Variants

In order to confirm the differential splicing of genes identified in the gene chip analysis, RNA samples from AA and CA PCa's were tested by reverse transcription polymerase chain reaction (RT-PCR) with specially designed primers listed in Table 1.

TABLE 1

Primers for qRT-PCR validations of splice variants (-L and -S forms)

| Gene | Primers |
|---|---|
| PIK3CD | Primer-f (SEQ ID NO. 2): CAAACTGAAGGCCCTGAATGA <br> Primer-r (SEQ ID NO. 3): TCTCGGATCATGATGTTGTCG |
| FGFR3 | Primer-f (SEQ ID No. 20): ACAACGTGATGAAGATCGCA <br> Primer-r (SEQ ID No. 21): AGGTCGTGTGTGCAGTTG |
| TSC2 | Primer-f (SEQ ID No. 29): TTTGACTTCCTGTTGCTGCT <br> Primer-r (SEQ ID No. 30): TGAGCACTTTATAGCGCAG |
| RASGRP2 | Primer-f (SEQ ID No. 38): TCACGGTGTCTCTGGATCAGT <br> Primer-r (SEQ ID No. 39): CCACCATCTTCTCGATGTGCT |
| ITGA4 | Primer-f (SEQ ID No. 53): TCTTGCTGTTGGGAGTATGAA <br> Primer-r (SEQ ID No. 54): TGATACTGAGGTCCTCTTCCG |
| MET | Primer-f (SEQ ID No. 66): TGGTGGAAAGAACCTCTCAA <br> Primer-r (SEQ ID No. 67): ATCTTGGCTCACTGCAACCT |
| NF1 | Primer-f (SEQ ID No. 71): GCATTTTGGAACTGGGTAGAA <br> Primer-r (SEQ ID No. 72): AACCACCATGGACTGAACAA |
| BAK1 | Primer-f (SEQ ID No. 80): CCTGTTTGAGAGTGGCATCAA <br> Primer-r (SEQ ID No. 81): TTGATGCCACTCTCAAACAGG |

Preferential expression of a particular exon in either AA or CA PCa specimens for the PIK3CD, FGFR3, TSC2, ITGA4, MET, NF1, BAK1, and RASGRP2 genes is seen. EIFIAX and PPA1 served as internal RT-PCR control genes, which are expressed equally in AA and CA PCa specimens.

Figure 4:
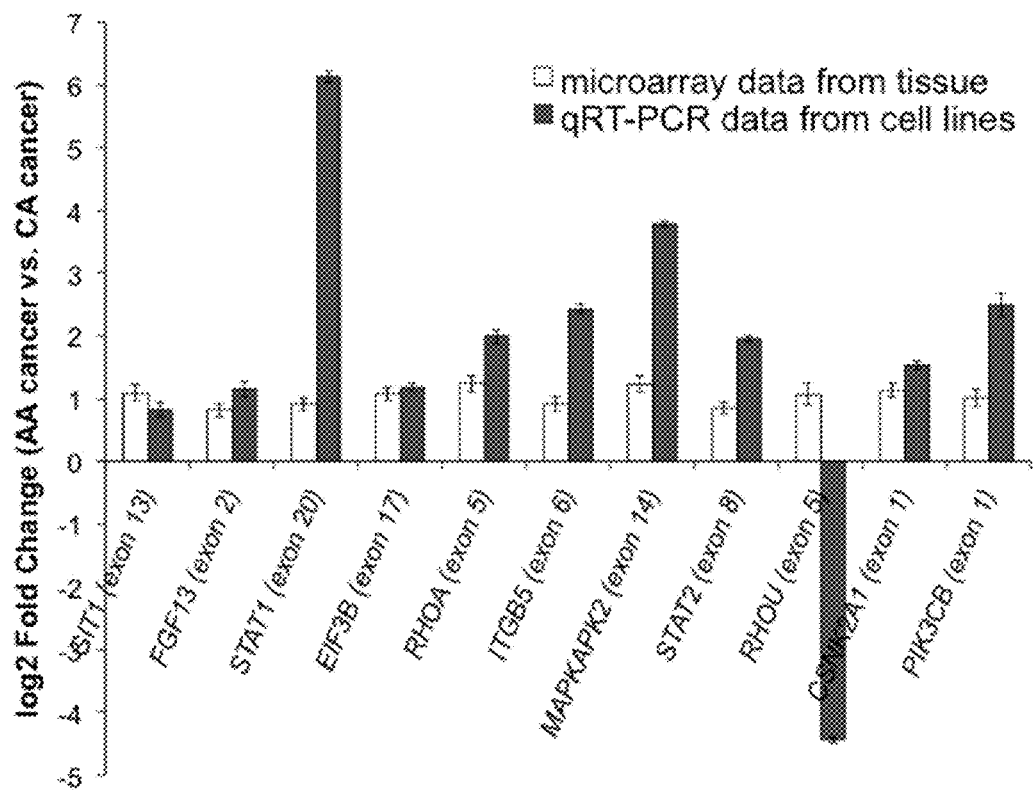
FIG. 4 shows differential expression of cancer genes between AA and CA populations as determined from gene chip analysis (white bars) and qPCR validation (solid bars). The differential expression of exons was found to be in the same direction (for all but 1; RhoU) and same overall magnitude (for all but 1; STAT1) for both PCa specimens and cell lines (AA PCa cell line E006AA vs. CA PCa cell line VCap). Data mean+SE of n=3. Similar findings were seen for AA PCa line MDA PCa 2b vs. VCap.

Validating qRT-PCR data for other differentially expressed genes was also compared against the log 2 fold change results from the microarray experiment described in Example 1. The results showed correlation between the microarray and validating qRT-PCR data (FIG. 4).

Example 4—Differentially Spliced Genes Affect Cancer Pathways

Figure 3:
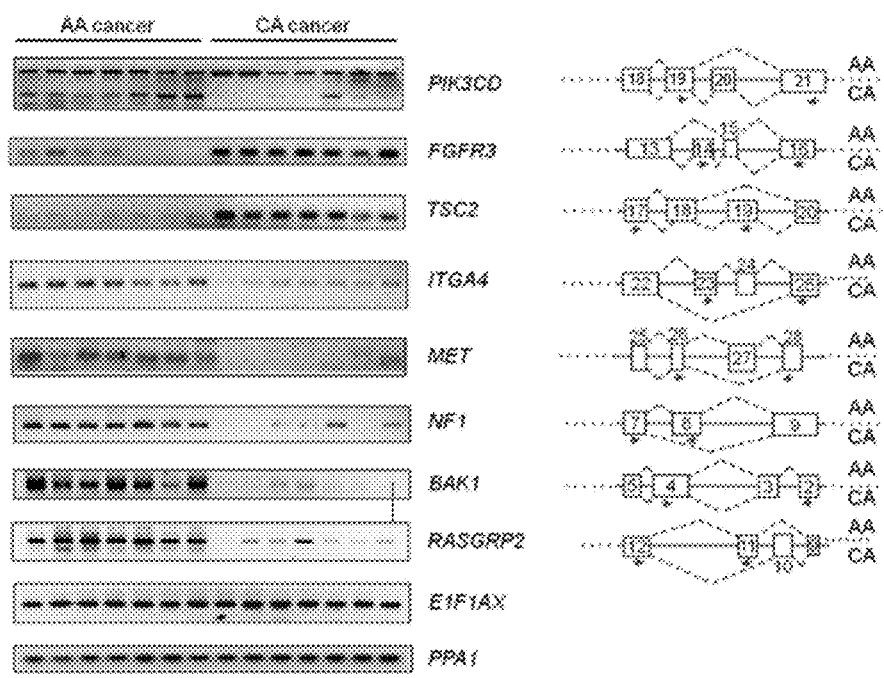
FIG. 3 shows differential splicing events in AA and CA PCa specimens. (A) Shows qRT-PCR validation of selected differentially spliced genes in AA and CA cancer populations (left), and differential splicing models for each gene (right). (B) Depicts the genetic pathways for cancer. More than half of the genes in this pathway exhibit differential splicing between AA and CA prostate cancers.
Figure 3:
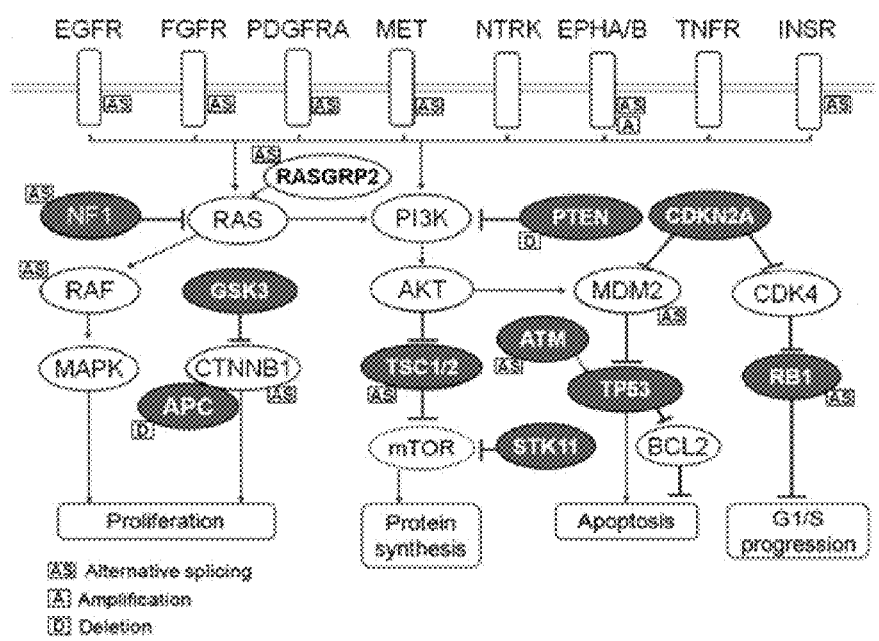

Somatic mutations affect key pathways in lung adenocarcinoma. (Nature 2008, 455: 1069-1075). Of interest from a cancer disparities perspective is that many of these same genes that were discovered to be prone to population-specific splicing patterns as identified in Example 1 of this application. FIG. 3 indicates genes marked with (AS) define differential alternative splicing events occurring in AA versus CA PCa. (Copy number amplifications (A) and deletions (D) are also indicated).

At least 11 out of 26 genes residing in the 5 oncogenic signaling pathways have been identified by the inventors as exhibiting differential splicing between AA and CA PCa specimens. These genes include FGFR2, PDGFRA, MET, EPHA3, NF1, RASGRP2, CTNNB1, TSC2, ATM, CDK4, and RBI. The inventors further show that differential mRNA splicing in racial populations plays an important role in cancer health disparities.

Example 5—Functional Consequences of Splice Variants in PCa Cell Lines Derived from AA and CA Patients In order to determine the effects of the expression of the short or long forms of PIK3CD, cells expressing the S or L variants were tested for their ability to invade Matrigel™ and cell proliferation.

Figure 5:
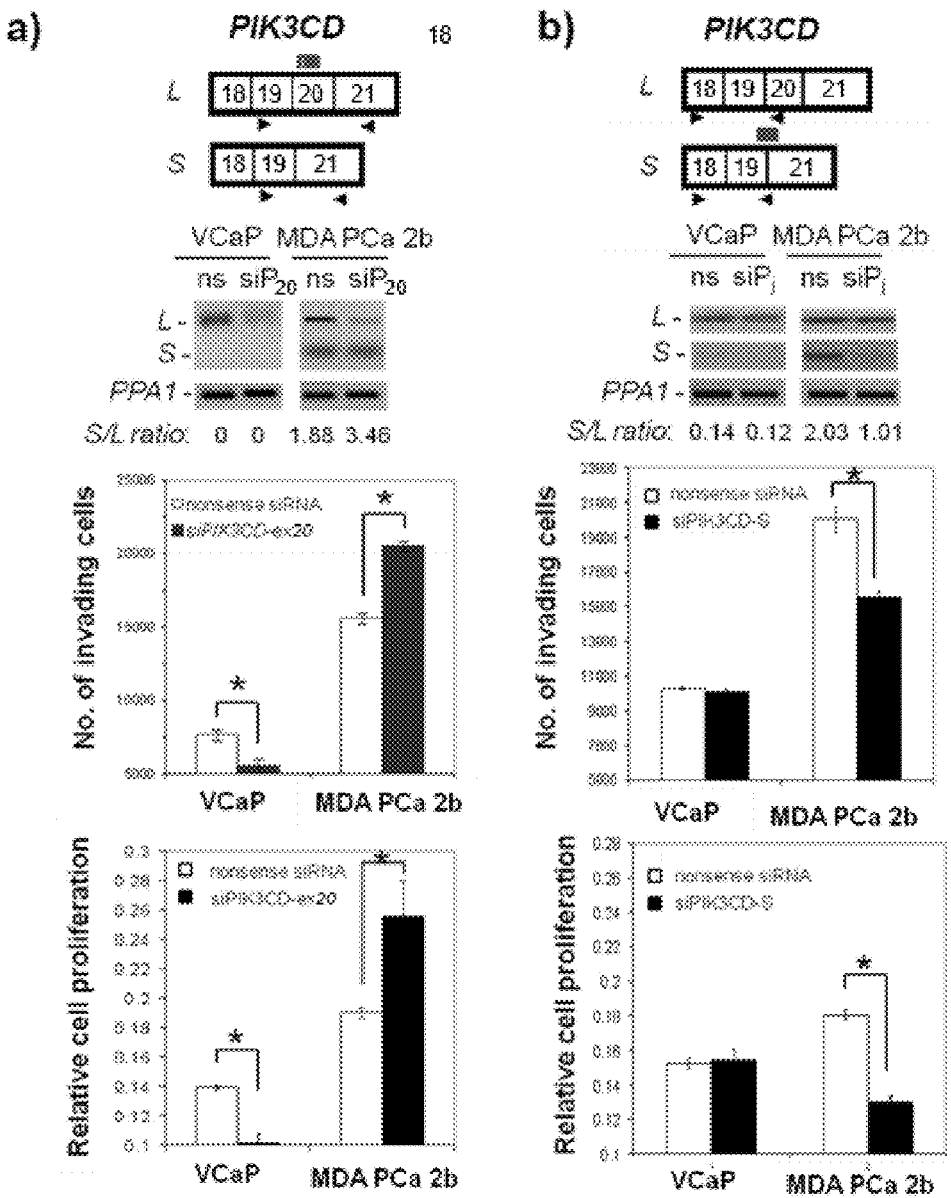
FIG. 5 demonstrates that the short splice variant (S) for PIK3CD encodes a more aggressive version of the gene (i.e. leading to greater proliferation and invasion of cancer cells) compared to the long (L) counterpart. (A) Top panels show PCR bands of S and L PIK3CD variants from MDA PCa 2b cells (from AA patients), and VCAP cells (from CA patient) transformed with nonsense control siRNA constructs (ns) and siRNA constructs targeted against exon 20 of the L form. The accumulation of exon splice variants can be shifted with siRNA. Bottom panels show increased Matrigel invasion and an increase in proliferation as assessed by BrdU incorporation. (B) Top panels show PCR bands of S and L PIK3CD variants as in part A. Transformations with siRNA constructs targeting S variant can shift accumulation to L variant. Bottom panels show decreased Matrigel invasion and decreased cell proliferation.

The results demonstrate that the splice variant (short form or S variant) for phosphoinositide-3 kinase delta (PIK3CD) found in AA PCa specimens encodes a more aggressive version of the gene (i.e. leading to greater proliferation and invasion of cancer cells) compared to the variant counterpart (long form or L variant) found in CA PCa specimens (FIG. 5). In the CA PCa cell line VCaP, the L form is the only variant found, while very little to no expression of the S variant is seen (and hence the reason we refer to the L variant as the 'CA isoform') (FIG. 5A). The predominant expression of the L variant and very little to no expression of the S variant in the CA PCa cell line is consistent with the CA patient samples.

SiRNA-mediated knockdown of the L variant in VCaP cells leads to a decrease in Matrigel™ invasion and a decrease in proliferation (FIG. 5A). By comparison, the AA PCa cell line MDA PCa 2b expresses both an L and S variant, and knockdown of the L variant leads to an increase in Matrigel invasion and an increase in proliferation (FIG. 5A).

Since VCaP cells express very little to no S variant, targeted siRNA-mediated knockdown of this variant leads to no change in Matrigel invasion and proliferation (FIG. 5B). In contrast, targeted knockdown of the S variant in MDA PCa 2b cells leads to decreased Matrigel invasion and decreased proliferation (since the S variant is found almost exclusively in AA patient samples, it is referred to as the 'AA variant') (FIG. 5B).

These data indicate that the balance of S to L isoforms in MDA PCa 2b cells dictates the oncogenic profile of the AA PCa cell line. Namely, knocking down the L variant in MDA PCa 2b cells increases the S/L ratio, leading to a higher proportion of the aggressive S variant and consequently increased invasiveness and proliferation of the cell line. In contrast, knocking down the S variant in MDA PCa 2b cells decreases the S/L ratio, leading to a higher proportion of the less aggressive L variant and consequently decreased invasiveness and proliferation of the cell line. Analogous findings were obtained in MDA PCa 2b cells when the ratio of the AA variant' (S or b isoform) was increased over the 'CA variant' (L or an isoform) for the FGFR3, TSC2.

For RASGRP2, the long variant (with exon 10) is common to both AA and CA patients, whereas the short variant (without exon 10) is unique to AA. Targeted knockdown of the long splicing variant in VCaP cells reduced Matrigel™ invasion and an increase in proliferation (results not shown). In contrast, target knockdown of the RASGRP2 long variant in MDA PCa 2b Cells has the opposite effect.

Activation of AKT is known to promote cell growth and mRNA translation. When the expression of PIK3CD "long" variant is knocked down by siRNA targeting of Exon 20 in the VCaP cell line, which only expresses the long variant, there is a decrease of phosphorylation of AKT, compared to nonsense siRNA control, and also decrease of phosphorylation of downstream signaling proteins mTOR and S6. However, in MDA PCa 2b cells, which express the short variant of PIK3CD, knocking down the long variant of PIK3CD markedly increases AKT phosphorylation, both on Thr308 and Ser473, and increases phosphorylation of mTOR and S6. In other words, increasing S/L variants proportion in MDA PCa 2b cells activates the AKT pathways.

Example 7—In-Vitro Tests for PIKCD Variant Effects

In order to characterize oncogenic differences of splice variant pairs, cells expressing the PIK3CD L and S forms were studied for the ability to proliferate in vitro. The results showed that the AA-specific S variant of PIK3CD is more oncogenic and resistant to small molecule inhibitor treatments. Epitope-tagged L and AA-specific S variants of PIK3CD were individually over-expressed in CA-derived VCap cells and PC-3 cells. The cells were treated with either a vehicle control or a CAL101 cancer treatment drug. Cells were then lysed and RNA was extracted. The RNA was then used in RT-PCR reactions to quantify the AKT response.

Figure 7:
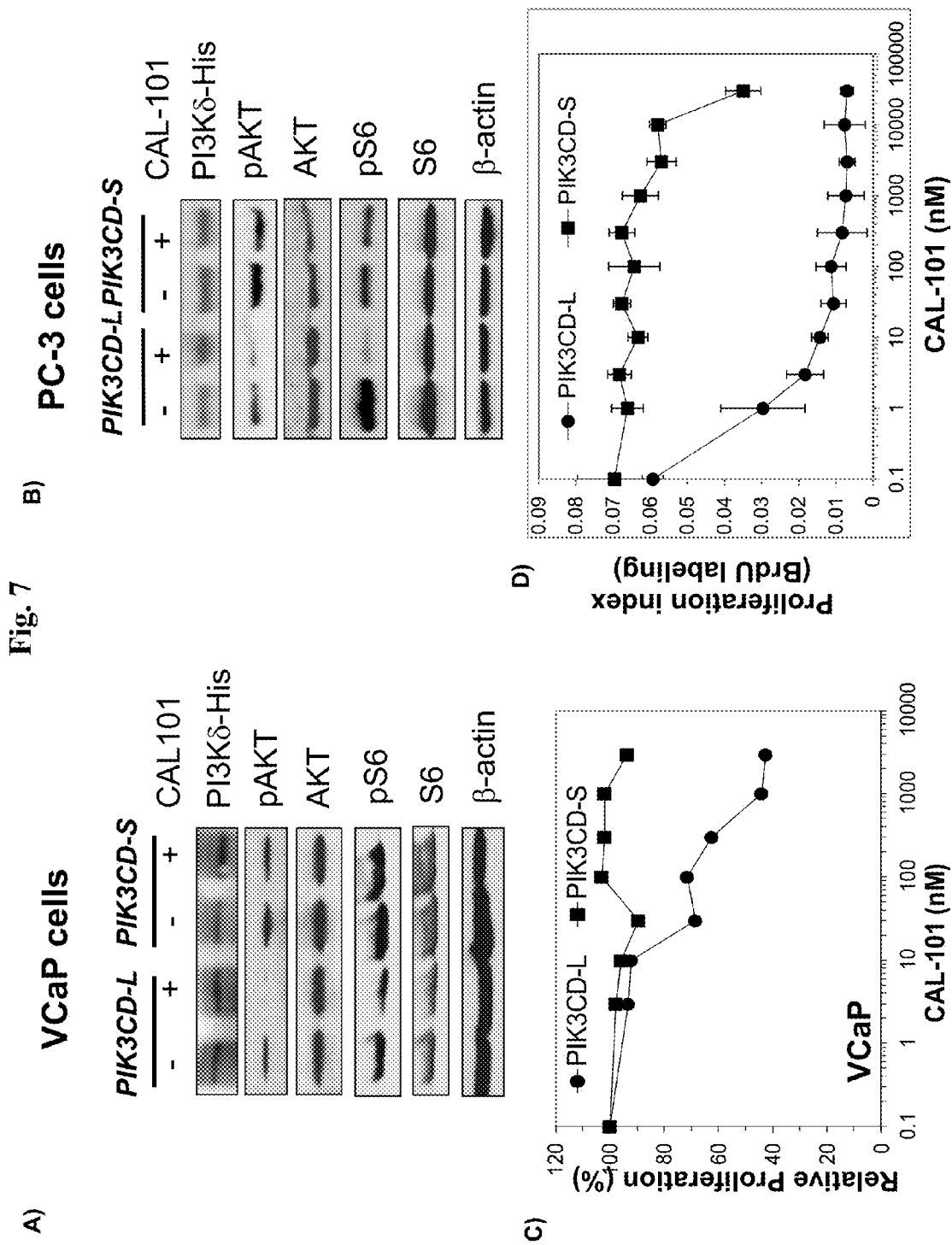
FIG. 7 shows that AA-specific S variant of PIK3CD is more oncogenic and resistant to small molecule inhibitor. Epitope-tagged L and AA-specific S variants of PIK3CD were individually over-expressed in CA-derived VCap cells (A) or PC-3 cells (B) treated with CAL101. S variant has 2-fold greater activity than L variant based on downstream phosphorylation of AKT (pAKT). Note that inhibitor CAL101 completely inhibits L but has no effect on S variant activity. Blots representative of n=4. VCap cells (C) and PC-3 cells (D) expressing L variant shows reduced cancerous proliferation in response to CAL 101 treatment while cells expressing S variant were largely resistant to CAL 101 treatments.

The PIK3CD S variant produced has 2-fold greater activity than L variant of downstream phosphorylation of AKT (pAKT) (FIG. 7A). CAL101 completely inhibits the AKT response of VCAP cells expressing the L variant but has no effect on S variant activity. (FIG. 7a).

The proliferation of cells expressing the S and L variants of PIK3CD was measured via BrdU labeling. Cells treated with CAL101 which expressed the L variant showed a dose dependent reduction in proliferation (FIG. 7D). Cells expressing PIK3CD-S variants were resistant to CAL 101 treatments, only showing reductions in BrdU incorporation at the highest treatment levels (FIG. 7D). Relative proliferation levels of VCaP cells expressing S and L variants showed similar results, with only the L variant exhibiting dose dependent responses to CAL101 treatments (FIG. 7C).

Example 7—In-Vivo Tests for PIKCD Tumor Growth

Figure 8:
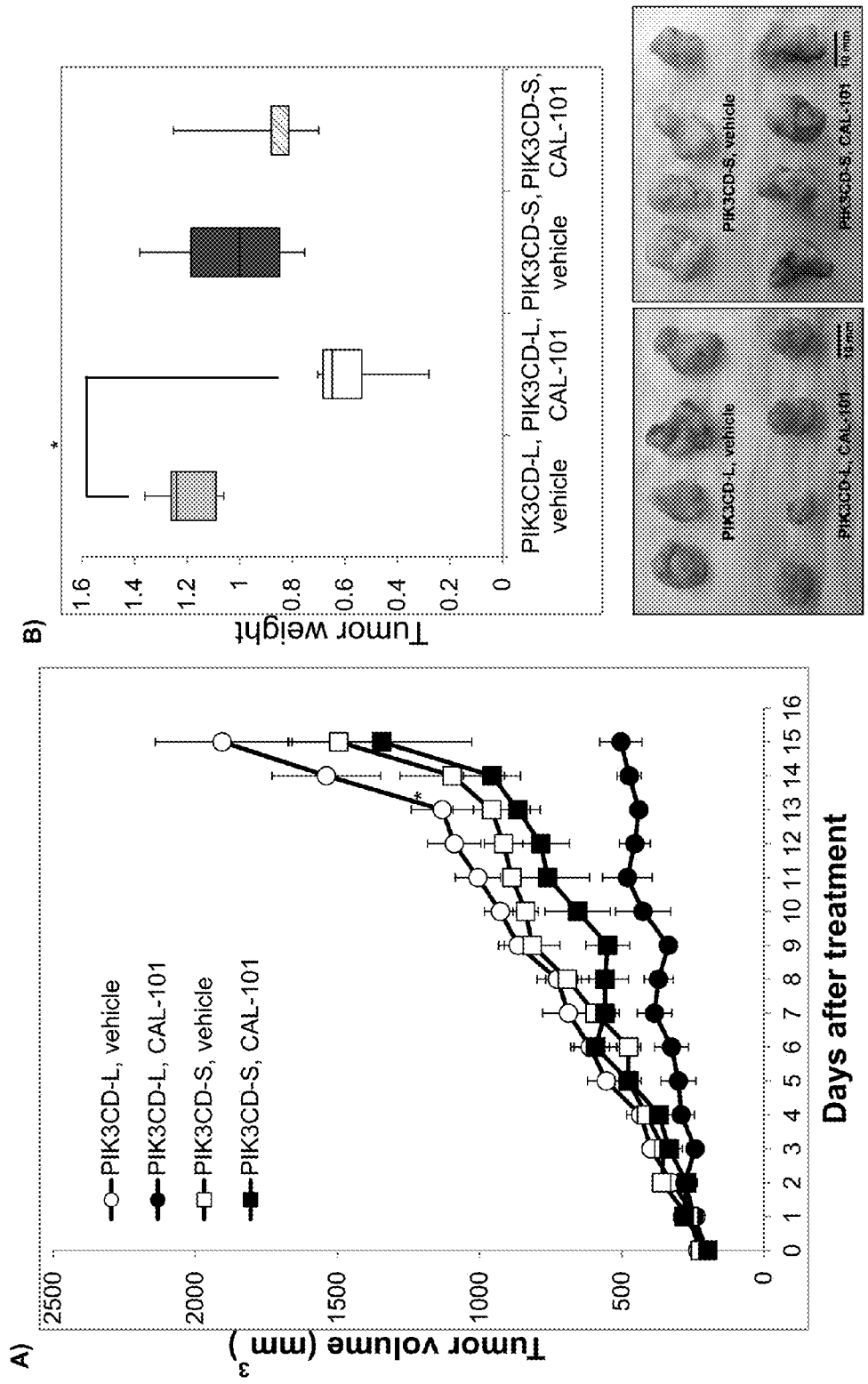
FIG. 8 shows that tumors expressing S variants of PIK3CD in mice were more resistant to CAL101 treatments and increased in weight at faster rates than tumors expressing L variants of the gene. (A) PC-3 cells stably expressing PIK3CD-L exhibited reduced tumorigenesis in NOD-SCID mice upon CAL-101 treatment. In contrast, PC-3 cells stably expressing PIK3CD-S exhibited resistance to CAL-101 inhibition of tumorigenesis in NOD-SCID mice. (B) Tumor weights and gross morphology of the tumor xenografts from (a). The box plots represent mean tumor weights after 15-days vehicle or CAL-101 treatment (ANOVA, n=5 independent mice for each treatment group at each time point).
Figure 9:
FIG. 9 lung metastases by PCa cells expressing PIK3CD isoforms in NOD-SCID mice. NOD-SCID mice were tail-vein injected with 2×106 of PC-3 cells stably expressing PIK3CD-L or PIK3CD-S isoform. The mice were treated with vehicle or CAL-101 (three times per week) for 8 weeks. Representative photographs (from n=10 for each group) for lung metastases were shown. Lungs were stained with India ink and bleached such that normal lung material stained dark, while metastases appear white in coloration. CAL101 treatments proved effective against cancerous cells expressing the PIK3CD L variant, but less so against S variant treated mice.
Figure 10:
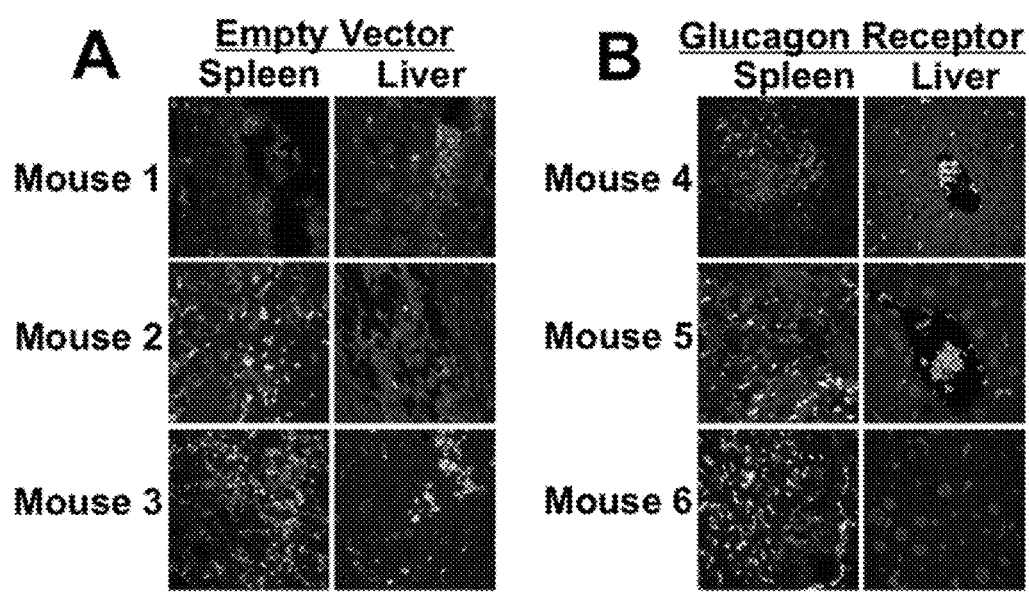
FIG. 10 intrasplenic injection and metastasis of hepatocellular carcinoma cells. (A) SCID-NOD mice injected with fluorescently tagged Hep3B cells expressing empty vector (red) can be seen with marked growth in spleen and metastasis to liver. (B) SCID-NOD mice injected with fluorescently tagged Hep3B cells over-expressing the glucagon receptor (red) have marked growth in spleen but no metastasis to liver. Blue=DAPI nuclear staining.

In order to characterize oncogenic differences of splice variant pairs in vivo, cells expressing the PIK3CD L and S forms were transplanted into SCID-NOD immuno-deficient mice. Two million PC-3 cells expressing PIK3CDL or PIK3CD-S were injected subcutaneously into the left flanks of each NOD-SCID mice and allowed to develop tumors under vehicle or CAL-101 treatments. After establishment, each mouse was treated with either vehicle control treatment, or the CAL101 cancer treatment drug. Weight and volume measurements for the primary tumor were tracked daily. Mice with transplanted tumors expressing the PIK3CD-L variant were responsive to CAL101 treatments, showing reduced tumor growth throughout the experiment which resulted in a significant tumor weight reduction at the end of 16 days (FIG. 8A, left panel for time course, FIG. 8B for final weights and statistical analysis). In contrast, mice with transplanted tumors expressing the PIK3CD-S variant did not show significant differences between control vehicle treatments (FIG. 8B). Thus cells expressing the S variant of PIK3CD were insensitive to CAL-101 treatments for their ability to grow. CAL-101 (undergoing preclinical testing for hematological malignancies; inhibits kinase activity of PIK3CD, which in turn inhibits downstream phosphorylation of AKT (Herman S E et al., *Blood.* 2010; 116(12): 2078-2088; Lannutti B J et al., *Blood.* 2011; 117(2):591-594), while the L variant is sensitive (FIG. 8). Therefore, these data demonstrate the need to genotype variant expression in the PCa prior to treatment Example 8—Tail-Vein Injection of PIK3CD-L or PIK3CD-S Expressing Cells to Study Lung Metastasis We further tested the inhibitory effects of CAL-101 treatment on in vivo tumor metastases in NOD-SCID mice carrying PIK3CD-L or PIK3CD-S expressing PC-3 cells. Mice were injected in the tail vein with either PIK3CD-L or PIK3CD-S expressing cells, and administrated vehicle or 50 mg/kg CAL-101 via i.p. injection (3 times a week). After 8 weeks, lungs were isolated from animals and stained with India ink and bleached with Fekete's solution (70% ethanol, 3.7% formaldehyde, 0.75 M glacial acetic acid. This protocol will stain normal lung tissue black while metastases will appear white in coloration. In vehicle-treated mice that were tail-vein injected with PIK3CD-L expressing cells, there was clear development of metastases in the lungs (white portions of the lungs) (FIG. 9). In contrast, there was significant inhibition of metastases in the CAL-101 treatment group injected with PIK3CD-L expressing cells (i.e. a large percentage of the lung stained black, indicating normal lung tissue). In mice tail-vein injected with PIK3CD-S expressing cells, CAL-101 treatment had limited to no efficacy in inhibiting lung metastases when compared to the vehicle-treated control group.

Example 9—FGFR3 Short and Long Isoforms

All future molecular and animal experiments with the FGFR3 short and long isoforms will parallel the experiments that were performed on the PI3KCD short and long isoforms as described in Examples 5-8.

For example, PCa cell lines will be grown in appropriate culture medium containing 10% serum up to passage (P) 9. A dose response assay will be conducted first to determine the optimal concentration of siRNA needed to obtain the highest knockdown efficiency as measured by mRNA (qRT-PCR) and protein expression (western blotting when commercially antibodies are available). The siRNA duplex will be mixed with Lipofectamine 2000 (Life Technologies) and added to the cells at P6 to P9 for two time courses of 12 and 24 hours. Following siRNA transfection, the cells will be harvested at two different time points of 24 and 48 hours and screened for a loss- or gain-of-function for the following phenotypes: (a) proliferative activity using BrdU incorporation after BrdU pulse labeling, (b) cell cycle distribution using propidium iodide to determine the number of cells in different phases of cell cycle, (c) apoptosis by measuring Annexin V through FACS analysis and/or caspase-3 activity, (d) invasiveness by Matrigel™ assay, and (e) sensitivity to chemotherapy by measuring the number of apoptotic cells after doxorubicin or etoposide treatment (for example).

All phenotypic assays are in place (House C D et al., *Cancer Res.* 2010; Wang B-D et al., *Molecular Cancer.* 2010. 9:98; Teramoto H et al., *Oncogene.* 2005; 24(3):489-501; Teramoto H et al. *Oncogene.* 2003; 22(17):2689-2697; Riz I et al., *Molecular Cancer.* 2010, 9:181).

An aliquot of transfected cells undergoing screening will be set aside for western blotting and qRT-PCR to verify the extent of splice variant knockdown. All protein expressions will be quantified using densitometry and normalized to an internal control protein such as GAPDH or beta-actin. All measurements will be performed at least 4 times in triplicate. Analysis of variance (ANOVA) with post-hoc test (e.g. Tukey) or Student's t-test will be used to compare all parameters.

Example 10—FGFR3 Functional Consequence and In-Vitro Functional Validation

Full length, epitope-tagged (6×His) versions of each of the FGFR3 splice variant pairs will be generated by RT-PCR for ectopic over-expression studies. The full-length over-expression studies are anticipated to compliment the knock-down studies. Epitope-tagged variant clones will be sub-cloned into pcDNA3 (G418 selectable marker) and stably transfected into PCa cell lines using standard molecular biology approaches in the lab (Malek R L et al., *J Biol Chem.* 2001; 276(8):5692-5699; Joe B et al., *Human molecular genetics.* 2009; 18(15):2825-2838; Glickman M et al., *Molecular and cellular neurosciences.* 1999; 14(2):141-152).

When appropriate, we will also generate stable lines in CHO and HEK293 cells or the immortalized CA prostate epithelial cell line PZ-HPV-7 117 (e.g. allow comparison of enzyme activity of AA-specific variant vs. CA-counterpart variant; or perform pull-downs with dual mass spec to identify binding partners). Western analysis will be performed on the epitope tag of each variant (e.g. AA-specific variant vs. CA-counterpart variant) to ensure equal expression in stable cell lines. In addition, we will isolate clonal lines expressing various levels of the variant protein for phenotypic analysis (i.e. low, intermediate, high expression). All measurements will be performed at least 4 times in triplicate.

Stable lines containing population-specific variants (e.g. AA-specific variant vs. CA-counterpart variant) will be screened for loss- or gain-of-function phenotypes as described in Example 9. In addition to the above-mentioned phenotypic screens, we will apply the appropriate biochemical assay to measure enzymatic activity of splice variants stably expressed in CA-HPV-10, CHO or HEK cells. For example, a PI3 kinase activity assay (Millipore) and small molecule inhibitor screening on the S and L variants of FGFR3 will be performed.

Example 11—FGFR3 and PIK3CD In Vivo Assays for Angiogenesis

For splice variants having a role in angiogenesis, we will employ the Directed In Vivo Angiogenesis Assay (DIVAA: Trevigen Inc) 134. Angio-reactors containing basement membrane extract and PCa cells stably over-expressing AA- or CA-specific splice variant will be inserted subcutaneously into athymic mice. After 1-2 weeks, the angio-reactors will be removed and vascular endothelial cells that have grown into the reactors will be quantitated.

Example 12—FGFR3 In Vivo Assays for Proliferation

If a splice variant of interest is suspected of having a role in tumor formation/proliferation, we can again take advantage of an orthotopic mice model whereby xenografts of EGFP-expressing PCa cell line (expressing AA-specific variant or CA-counterpart variant; for example see variants of PIK3CD) infected with the pTRIPZ doxycyclin-inducible lentiviral vector containing a variant-specific shRNAmir for knockdown will be imaged for tumor collapse upon feeding of doxycyclin food pellets. Lentiviral-containing shRNAmir's will be constructed as previously described by the Lee lab 115.

INCORPORATION BY REFERENCE

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, patent publications, and nucleic acid and amino acid sequences cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

SEQUENCE LISTING

<160> NUMBER OF SEQ ID NOS: 87

<210> SEQ ID NO 1
<211> LENGTH: 3135
<212> TYPE: DNA

<213> ORGANISM: Homo sapiens

<400> SEQUENCE: 1

| | | | | | |
|---|---|---|---|---|---|
| atgcccctg | gggtggactg | ccccatggaa | ttctggacca | aggaggagaa | tcagagcgtt | 60 |
| gtggttgact | tcctgctgcc | cacaggggtc | tacctgaact | tccctgtgtc | ccgcaatgcc | 120 |
| aacctcagca | ccatcaagca | gctgctgtgg | caccgcgccc | agtatgagcc | gctcttccac | 180 |
| atgctcagtg | cccccgaggc | ctatgtgttc | acctgcatca | accagacagc | ggagcagcaa | 240 |
| gagctggagg | acgagcaacg | cgtctgtgt | gacgtgcagc | ccttcctgcc | cgtcctgcgc | 300 |
| ctggtggccc | gtgagggcga | ccgcgtgaag | aagctcatca | actcacagat | cagcctcctc | 360 |
| atcggcaaag | gcctccacga | gtttgactcc | ttgtgcgacc | cagaagtgaa | cgactttcgc | 420 |
| gccaagatgt | gccaattctg | cgaggaggcg | gccgcccgcc | ggcagcagct | gggctgggag | 480 |
| gcctggctgc | agtacagttt | cccctgcag | ctggagccct | cggctcaaac | ctgggggcct | 540 |
| ggtaccctgc | ggctcccgaa | ccgggcccctt | ctggtcaacg | ttaagtttga | gggcagcgag | 600 |
| gagagcttca | ccttccaggt | gtccaccaag | gacgtgccgc | tggcgctgat | ggcctgtgcc | 660 |
| ctgcggaaga | aggccacagt | gttccggcag | ccgctggtgg | agcagccgga | agactacacg | 720 |
| ctgcaggtga | acgcaggca | tgagtacctg | tatggcagct | acccgctctg | ccagttccag | 780 |
| tacatctgca | gctgcctgca | cagtgggttg | acccctcacc | tgaccatggt | ccattcctcc | 840 |
| tccatcctcg | ccatgcggga | tgagcagagc | aaccctgccc | ccaggtcca | gaaaccgcgt | 900 |
| gccaaaccac | ctcccattcc | tgcgaagaag | ccttcctctg | tgtccctgtg | gtccctggag | 960 |
| cagccgttcc | gcatcgagct | catccagggc | agcaaagtga | acgccgacga | gcggatgaag | 1020 |
| ctggtggtgc | aggccgggct | ttccacggc | aacgagatgc | tgtgcaagac | ggtgtccagc | 1080 |
| tcggaggtga | gcgtgtgctc | ggagcccgtg | tggaagcagc | ggctggagtt | cgacatcaac | 1140 |
| atctgcgacc | tgccccgcat | ggcccgtctc | tgctttgcgc | tgtacgccgt | gatcgagaaa | 1200 |
| gccaagaagg | ctcgctccac | caagaagaag | tccaagaagg | cggactgccc | cattgcctgg | 1260 |
| gccaacctca | tgctgtttga | ctacaaggac | cagcttaaga | ccggggaacg | ctgcctctac | 1320 |
| atgtggccct | ccgtcccaga | tgagaagggc | gagctgctga | accccacggg | cactgtgcgc | 1380 |
| agtaaccccca | acacggatag | cgccgctgcc | ctgctcatct | gcctgcccga | ggtggccccg | 1440 |
| cacccgtgt | actaccccgc | cctggagaag | atcttggagc | tggggcgaca | cagcgagtgt | 1500 |
| gtgcatgtca | ccgaggagga | gcagctgcag | ctgcgggaaa | tcctggagcg | gcggggtct | 1560 |
| ggggagctgt | atgagcacga | aaggacctg | tgtggaagc | tgcggcatga | agtccaggag | 1620 |
| cacttcccgg | aggcgctagc | ccggctgctg | ctggtcacca | agtggaacaa | gcatgaggat | 1680 |
| gtggcccaga | tgctctacct | gctgtgctcc | tggccggagc | tgcccgtcct | gagcgccctg | 1740 |
| gagctgctag | acttcagctt | ccccgattgc | acgtaggct | ccttcgccat | caagtcgctg | 1800 |
| cggaaactga | cggacgatga | gctgttccag | tacctgctgc | agctggtgca | ggtgctcaag | 1860 |
| tacgagtcct | acctggactg | cgagctgacc | aaattcctgc | tggaccgggc | cctggccaac | 1920 |
| cgcaagatcg | ccacttcct | tttctggcac | ctccgctccg | agatgcacgt | gccgtcggtg | 1980 |
| gccctgcgct | tcggcctcat | cctggaggcc | tactgcaggg | gcagcaccca | ccacatgaag | 2040 |
| gtgctgatga | agcaggggga | agcactgagc | aaactgaagg | ccctgaatga | cttcgtcaag | 2100 |
| ctgagctctc | agaagacccc | caagcccag | accaaggagc | tgatgcactt | gtgcatgcgg | 2160 |
| caggaggcct | acctagaggc | cctctcccac | ctgcagtccc | cactcgaccc | cagcaccctg | 2220 |
| ctggctgaag | tctgcgtgga | gcagtgcacc | ttcatggact | ccaagatgaa | gccctgtgg | 2280 |

```
atcatgtaca gcaacgagga ggcaggcagc ggcggcagcg tgggcatcat ctttaagaac    2340
ggggatgacc tccggcagga catgctgacc ctgcagatga tccagctcat ggacgtcctg    2400
tggaagcagg aggggctgga cctgaggatg acccccctatg gctgcctccc caccggggac   2460
cgcacaggcc tcattgaggt ggtactccgt tcagacacca tcgccaacat ccaactcaac    2520
aagagcaaca tggcagccac agccgccttc aacaaggatg ccctgctcaa ctggctgaag    2580
tccaagaacc cggggggaggc cctggatcga gccattgagg agttcaccct ctcctgtgct   2640
ggctattgtg tggccacata tgtgctgggc attggcgatc ggcacagcga caacatcatg    2700
atccgagaga gtgggcagct gttccacatt gattttggcc actttctggg gaatttcaag    2760
accaagtttg gaatcaaccg cgagcgtgtc ccattcatcc tcacctacga ctttgtccat    2820
gtgattcagc aggggaagac taataatagt gagaaatttg aacggttccg gggctactgt    2880
gaaagggcct acaccatcct gcggcgccac gggcttctct tcctccacct ctttgccctg    2940
atgcgggcgg caggcctgcc tgagctcagc tgctccaaag acatccagta tctcaaggac    3000
tccctggcac tggggaaaac agaggaggag gcactgaagc acttccgagt gaagtttaac    3060
gaagccctcc gtgagagctg gaaaaccaaa gtgaactggc tggcccacaa cgtgtccaaa    3120
gacaacaggc agtag                                                    3135
```

```
<210> SEQ ID NO 2
<211> LENGTH: 21
<212> TYPE: DNA
<213> ORGANISM: Artificial Sequence
<220> FEATURE:
<223> OTHER INFORMATION: Primers for qRT-PCR validations of PI3KCD
      splice variants

<400> SEQUENCE: 2
caaactgaag gccctgaatg a                                              21

<210> SEQ ID NO 3
<211> LENGTH: 21
<212> TYPE: DNA
<213> ORGANISM: Artificial Sequence
<220> FEATURE:
<223> OTHER INFORMATION: Primers for qRT-PCR validations of PIK3CD
      splice variants

<400> SEQUENCE: 3
tctcggatca tgatgttgtc g                                              21

<210> SEQ ID NO 4
<211> LENGTH: 19
<212> TYPE: RNA
<213> ORGANISM: Artificial Sequence
<220> FEATURE:
<223> OTHER INFORMATION: siRNA targeting PI3KCD exon 23

<400> SEQUENCE: 4
ccaacaucca acucaacaa                                                 19

<210> SEQ ID NO 5
<211> LENGTH: 19
<212> TYPE: RNA
<213> ORGANISM: Artificial Sequence
<220> FEATURE:
<223> OTHER INFORMATION: siRNA targeting exon 23

<400> SEQUENCE: 5
```

-continued

| uuguugaguu ggauguugg | | | | | 19 |

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6

| tgcgaagaag ctggtggtgc | | | | | 20 |

<210> SEQ ID NO 7
<211> LENGTH: 3045
<212> TYPE: DNA
<213> ORGANISM: Homo sapiens

<400> SEQUENCE: 7

| atgccccctg gggtggactg ccccatggaa ttctggacca aggaggagaa tcagagcgtt | 60 |
| gtggttgact tcctgctgcc cacagggggtc tacctgaact ccctgtgtc ccgcaatgcc | 120 |
| aacctcagca ccatcaagca gctgctgtgg caccgcgccc agtatgagcc gctcttccac | 180 |
| atgctcagtg gccccgaggc ctatgtgttc acctgcatca accagacagc ggagcagcaa | 240 |
| gagctggagg acgagcaacg gcgtctgtgt gacgtgcagc ccttcctgcc cgtcctgcgc | 300 |
| ctggtggccc gtgagggcga ccgcgtgaag aagctcatca actcacagat cagcctcctc | 360 |
| atcggcaaag gcctccacga gtttgactcc ttgtgcgacc agaagtgaa cgactttcgc | 420 |
| gccaagatgt gccaattctg cgaggaggcg ccgcccgcc ggcagcagct gggctgggag | 480 |
| gcctggctgc agtacagttt ccccctgcag ctggagccct cggctcaaac ctgggggcct | 540 |
| ggtaccctgc ggctcccgaa ccgggccctt ctggtcaacg ttaagtttga gggcagcgag | 600 |
| gagagcttca ccttccaggt gtccaccaag gacgtgccgc tggcgctgat ggcctgtgcc | 660 |
| ctgcggaaga aggccacagt gttccggcag ccgctggtgg agcagccgga agactacacg | 720 |
| ctgcaggtga acggcaggca tgagtacctg tatggcagct acccgctctg ccagttccag | 780 |
| tacatctgca gctgcctgca cagtgggttg accctcacc tgaccatggt ccattcctcc | 840 |
| tccatcctcg ccatgcggga tgagcagagc aaccctgccc ccaggtcca gaaaccgcgt | 900 |
| gccaaaccac ctcccattcc tgcgaagaag ctggtggtgc aggccgggct tttccacggc | 960 |
| aacgagatgc tgtgcaagac ggtgtccagc tcggaggtga gcgtgtgctc ggagcccgtg | 1020 |
| tggaagcagc ggctggagtt cgacatcaac atctgcgacc tgccccgcat ggcccgtctc | 1080 |
| tgctttgcgc tgtacgccgt gatcgagaaa gccaagaagg ctcgctccac caagaagaag | 1140 |
| tccaagaagg cggactgccc cattgcctgg gccaacctca tgctgtttga ctacaaggac | 1200 |
| cagcttaaga ccggggaacg ctgcctctac atgtggccct ccgtcccaga tgagaagggc | 1260 |
| gagctgctga ccccacgggg cactgtgcgc agtaacccca acacggatag cgccgctgcc | 1320 |
| ctgctcatct gcctgcccga ggtggcccccg caccccgtgt actaccccgc cctggagaag | 1380 |
| atcttggagc tggggcgaca cagcgagtgt gtgcatgtca ccgaggagga gcagctgcag | 1440 |
| ctgcgggaaa tcctggagcg gcgggggtct ggggagctgt atgagcacga gaaggacctg | 1500 |
| gtgtggaagc tgcggcatga agtccaggag cacttcccgg aggcgctagc ccggctgctg | 1560 |
| ctggtcacca gtggaacaa gcatgaggat gtgcccaga tgctctacct gctgtgctcc | 1620 |
| tggccggagc tgcccgtcct gagcgccctg gagctgctag acttcagctt ccccgattgc | 1680 |
| cacgtaggct ccttcgccat caagtcgctg cggaaactga cggacgatga gctgttccag | 1740 |

```
tacctgctgc agctggtgca ggtgctcaag tacgagtcct acctggactg cgagctgacc    1800
aaattcctgc tggaccgggc cctggccaac cgcaagatcg gccacttcct tttctggcac    1860
ctccgctccg agatgcacgt gccgtcggtg gccctgcgct tcggcctcat cctggaggcc    1920
tactgcaggg gcagcaccca ccacatgaag gtgctgatga agcaggggga agcactgagc    1980
aaactgaagg ccctgaatga cttcgtcaag ctgagctctc agaagacccc caagccccag    2040
accaaggagc tgatgcactt gtgcatgcgg caggaggcct acctagaggc cctctcccac    2100
ctgcagtccc cactcgaccc cagcaccctg ctggctgaag tctgcgtgga gcagtgcacc    2160
ttcatggact ccaagatgaa gcccctgtgg atcatgtaca gcaacgagga ggcaggcagc    2220
ggcggcagcg tgggcatcat ctttaagaac ggggatgacc tccggcagga catgctgacc    2280
ctgcagatga tccagctcat ggacgtcctg tggaagcagg aggggctgga cctgaggatg    2340
accccctatg gctgcctccc caccggggac cgcacaggcc tcattgaggt ggtactccgt    2400
tcagacacca tcgccaacat ccaactcaac aagagcaaca tggcagccac agccgccttc    2460
aacaaggatg ccctgctcaa ctggctgaag tccaagaacc gggggaggc cctggatcga     2520 gccattgagg agttcaccct ctcctgtgct ggctattgtg tggccacata tgtgctgggc    2580
attggcgatc ggcacagcga caacatcatg atccgagaga gtgggcagct gttccacatt    2640
gattttggcc acttctctggg gaatttcaag accaagtttg gaatcaaccg cgagcgtgtc    2700
ccattcatcc tcacctacga ctttgtccat gtgattcagc aggggaagac taataatagt    2760
gagaaatttg aacggttccg gggctactgt gaaagggcct acaccatcct gcggcgccac    2820
gggcttctct tcctccacct ctttgccctg atgcgggcgg caggcctgcc tgagctcagc    2880
tgctccaaag acatccagta tctcaaggac tccctggcac tggggaaaac agaggaggag    2940
gcactgaagc acttccgagt gaagtttaac gaagccctcc gtgagagctg gaaaaccaaa    3000
gtgaactggc tggcccacaa cgtgtccaaa gacaacaggc agtag                     3045
```

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
cugcgaagaa gcugguggu                                                   19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
accaccagcu ucuucgcag                                                   19

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
tggacctgag ggaggccct                                                  19

<210> SEQ ID NO 11
<211> LENGTH: 2967
<212> TYPE: DNA
<213> ORGANISM: Homo sapiens

<400> SEQUENCE: 11

| | | | | | |
|---|---|---|---|---|---|
| atgccccctg | gggtggactg | ccccatggaa | ttctggacca | aggaggagaa | tcagagcgtt | 60 |
| gtggttgact | tcctgctgcc | cacagggggtc | tacctgaact | tccctgtgtc | ccgcaatgcc | 120 |
| aacctcagca | ccatcaagca | gctgctgtgg | caccgcgccc | agtatgagcc | gctcttccac | 180 |
| atgctcagtg | ccccgaggc | ctatgtgttc | acctgcatca | accagacagc | ggagcagcaa | 240 |
| gagctggagg | acgagcaacg | cgtctgtgt | gacgtgcagc | ccttcctgcc | cgtcctgcgc | 300 |
| ctggtggccc | gtgagggcga | ccgcgtgaag | aagctcatca | actcacagat | cagcctcctc | 360 |
| atcggcaaag | gcctccacga | gtttgactcc | ttgtgcgacc | cagaagtgaa | cgactttcgc | 420 |
| gccaagatgt | gccaattctg | cgaggaggcg | ccgcccgcc | ggcagcagct | gggctgggag | 480 |
| gcctggctgc | agtacagttt | ccccctgcag | ctggagccct | cggctcaaac | ctgggggcct | 540 |
| ggtaccctgc | ggctcccgaa | ccgggccctt | ctggtcaacg | ttaagtttga | gggcagcgag | 600 |
| gagagcttca | ccttccaggt | gtccaccaag | gacgtgccgc | tggcgctgat | ggcctgtgcc | 660 |
| ctgcggaaga | aggccacagt | gttccggcag | ccgctggtgg | agcagccgga | agactacacg | 720 |
| ctgcaggtga | acggcaggca | tgagtacctg | tatggcagct | acccgctctg | ccagttccag | 780 |
| tacatctgca | gctgcctgca | cagtgggttg | accctcacc | tgaccatggt | ccattcctcc | 840 |
| tccatcctcg | ccatgcggga | tgagcagagc | aaccctgccc | ccaggtcca | gaaaccgcgt | 900 |
| gccaaaccac | ctcccattcc | tgcgaagaag | ccttcctctg | tgtccctgtg | gtccctggag | 960 |
| cagccgttcc | gcatcgagct | catccagggc | agcaaagtga | acgccgacga | gcggatgaag | 1020 |
| ctggtggtgc | aggccgggct | tttccacggc | aacgagatgc | tgtgcaagac | ggtgtccagc | 1080 |
| tcggaggtga | gcgtgtgctc | ggagcccgtg | tggaagcagc | ggctggagtt | cgacatcaac | 1140 |
| atctgcgacc | tgccccgcat | ggccgtctc | tgctttgcgc | tgtacgccgt | gatcgagaaa | 1200 |
| gccaagaagg | ctcgctccac | caagaagaag | tccaagaagg | cggactgccc | cattgcctgg | 1260 |
| gccaacctca | tgctgtttga | ctacaaggac | cagcttaaga | ccggggaacg | ctgcctctac | 1320 |
| atgtggccct | ccgtcccaga | tgagaagggc | gagctgctga | ccccacgggg | cactgtgcgc | 1380 |
| agtaacccca | cacggatag | cgccgctgcc | ctgctcatct | gcctgcccga | ggtggccccg | 1440 |
| caccccgtgt | actaccccgc | cctggagaag | atcttggagc | tggggcgaca | cagcgagtgt | 1500 |
| gtgcatgtca | ccgaggagga | gcagctgcag | ctgcgggaaa | tcctggagcg | cgggggtct | 1560 |
| ggggagctgt | atgagcacga | gaaggacctg | gtgtggaagc | tgcggcatga | agtccaggag | 1620 |
| cacttcccgg | aggcgctagc | ccggctgctg | ctggtcacca | gtggaacaa | gcatgaggat | 1680 |
| gtggcccaga | tgctctacct | gctgtgctcc | tggccggagc | tgcccgtcct | gagcgccctg | 1740 |
| gagctgctag | acttcagctt | ccccgattgc | cacgtaggct | ccttcgccat | caagtcgctg | 1800 |
| cggaaactga | cggacgatga | gctgttccag | tacctgctgc | agctggtgca | ggtgctcaag | 1860 |
| tacgagtcct | acctggactg | cgagctgacc | aaattcctgc | tggaccgggc | cctggccaac | 1920 |
| cgcaagatcg | ccacttcct | tttctggcac | ctccgctccg | agatgcacgt | gccgtcggtg | 1980 |
| gccctgcgct | tcggctcat | cctggaggcc | tactgcaggg | gcagcaccca | ccacatgaag | 2040 |
| gtgctgatga | agcagggga | agcactgagc | aaactgaagg | ccctgaatga | cttcgtcaag | 2100 |

```
ctgagctctc agaagacccc caagcccag accaaggagc tgatgcactt gtgcatgcgg      2160
caggaggcct acctagaggc cctctcccac ctgcagtccc cactcgaccc cagcaccctg     2220
ctggctgaag tctgcgtgga gcagtgcacc ttcatggact ccaagatgaa gcccctgtgg     2280
atcatgtaca gcaacgagga ggcaggcagc ggcggcagcg tgggcatcat ctttaagaac     2340
ggggatgacc tccggcagga catgctgacc ctgcagatga tccagctcat ggacgtcctg     2400
tggaagcagg aggggctgga cctgagggag gccctggatc gagccattga ggagttcacc     2460
ctctcctgtg ctggctattg tgtggccaca tatgtgctgg cattggcga tcggcacagc      2520 gacaacatca tgatccgaga gagtgggcag ctgttccaca ttgattttgg ccactttctg     2580
gggaatttca agaccaagtt tggaatcaac cgcgagcgtg tcccattcat cctcacctac     2640
gactttgtcc atgtgattca gcaggggaag actaataata gtgagaaatt tgaacggttc     2700
cggggctact gtgaaagggc ctacaccatc ctgcggcgcc acgggcttct cttcctccac     2760
ctctttgccc tgatgcgggc ggcaggcctg cctgagctca gctgctccaa agacatccag     2820
tatctcaagg actccctggc actggggaaa acagaggagg aggcactgaa gcacttccga     2880 gtgaagtta acgaagccct ccgtgagagc tggaaaacca agtgaactg gctggcccac      2940 aacgtgtcca agacaacag gcagtag                                          2967
```

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12
ugagggaggc ccuggaucga                                                   20

<210> SEQ ID NO 13
<211> LENGTH: 20
<212> TYPE: RNA
<213> ORGANISM: Artificial Sequence
<220> FEATURE:
<223> OTHER INFORMATION: Synthetic

<400> SEQUENCE: 13
ucgauccagg gccucccuca                                                   20

<210> SEQ ID NO 14
<211> LENGTH: 2877
<212> TYPE: DNA
<213> ORGANISM: Homo sapiens

<400> SEQUENCE: 14
atgccccctg gggtggactg ccccatggaa ttctggacca aggaggagaa tcagagcgtt       60
gtggttgact tcctgctgcc cacagggggtc tacctgaact tccctgtgtc ccgcaatgcc     120
aacctcagca ccatcaagca gctgctgtgg caccgcgccc agtatgagcc gctcttccac     180
atgctcagtg gccccgaggc ctatgtgttc acctgcatca accagacagc ggagcagcaa     240
gagctggagg acgagcaacg gcgtctgtgt gacgtgcagc ccttcctgcc cgtcctgcgc     300
ctggtggccc gtgagggcga ccgcgtgaag aagctcatca actcacagat cagcctcctc     360
atcggcaaag gcctccacga gtttgactcc ttgtgcgacc cagaagtgaa cgactttcgc     420
gccaagatgt gccaattctg cgaggaggcg gccgcccgcc ggcagcagct gggctgggag     480
```

```
gcctggctgc agtacagttt cccctgcag ctggagccct cggctcaaac ctgggggcct      540
ggtaccctgc ggctcccgaa ccgggcctt ctggtcaacg ttaagtttga gggcagcgag       600
gagagcttca ccttccaggt gtccaccaag gacgtgccgc tggcgctgat ggcctgtgcc      660
ctgcggaaga aggccacagt gttccggcag ccgctggtgg agcagccgga agactacacg      720
ctgcaggtga acggcaggca tgagtacctg tatggcagct acccgctctg ccagttccag      780
tacatctgca gctgcctgca cagtgggttg acccctcacc tgaccatggt ccattcctcc      840
tccatcctcg ccatgcggga tgagcagagc aaccctgccc ccaggtcca gaaaccgcgt       900 gccaaaccac ctcccattcc tgcgaagaag ctggtggtgc aggccgggct tttccacggc      960
aacgagatgc tgtgcaagac ggtgtccagc tcggaggtga gcgtgtgctc ggagcccgtg     1020
tggaagcagc ggctggagtt cgacatcaac atctgcgacc tgccccgcat ggcccgtctc     1080
tgctttgcgc tgtacgccgt gatcgagaaa gccaagaagg ctcgctccac caagaagaag     1140
tccaagaagg cggactgccc cattgcctgg gccaacctca tgctgtttga ctacaaggac     1200
cagcttaaga ccggggaacg ctgcctctac atgtggccct ccgtcccaga tgagaagggc     1260
gagctgctga accccacggg cactgtgcgc agtaacccca acacggatag cgccgctgcc     1320
ctgctcatct gcctgcccga ggtggccccg caccccgtgt actacccgc cctggagaag      1380 atcttggagc tggggcgaca cagcgagtgt gtgcatgtca ccgaggagga gcagctgcag     1440
ctgcgggaaa tcctggagcg gcgggggtct ggggagctgt atgagcacga aaggacctg      1500 gtgtggaagc tgcggcatga agtccaggag cacttcccgg aggcgctagc ccggctgctg     1560
ctggtcacca gtggaacaa gcatgaggat gtggcccaga tgctctacct gctgtgctcc      1620
tggccggagc tgcccgtcct gagcgccctg gagctgctag acttcagctt cccgattgc      1680 cacgtaggct ccttcgccat caagtcgctg cggaaactga cggacgatga gctgttccag     1740
tacctgctgc agctggtgca ggtgctcaag tacgagtcct acctggactg cgagctgacc     1800
aaattcctgc tggaccgggc cctggccaac cgcaagatcg ccacttcct tttctggcac      1860 ctccgctccg agatgcacgt gccgtcggtg gccctgcgct tcggcctcat cctggaggcc     1920
tactgcaggg gcagcacccca ccacatgaag gtgctgatga agcagggga agcactgagc     1980 aaactgaagg ccctgaatga cttcgtcaag ctgagctctc agaagacccc caagcccag      2040 accaaggagc tgatgcactt gtgcatgcgg caggaggcct acctagaggc cctctcccac     2100
ctgcagtccc cactcgaccc cagcaccctg ctggctgaag tctgcgtgga gcagtgcacc     2160
ttcatggact ccaagatgaa gccctgtgg atcatgtaca gcaacgagga ggcaggcagc      2220
ggcggcagcg tgggcatcat ctttaagaac ggggatgacc tccggcagga catgctgacc     2280
ctgcagatga tccagctcat ggacgtcctg tggaagcagg aggggctgga cctgagggag     2340
gccctggatc gagccattga ggagttcacc ctctcctgtg ctggctattg tgtggccaca     2400
tatgtgctgg gcattggcga tcggcacagc gacaacatca tgatccgaga gagtgggcag     2460
ctgttccaca ttgatttgg ccactttctg gggaatttca gaccaagtt tggaatcaac      2520 cgcgagcgtg tcccattcat cctcacctac gactttgtcc atgtgattca gcaggggaag     2580
actaataata gtgagaaatt tgaacggttc cggggctact gtgaaagggc ctacaccatc     2640
ctgcggcgcc acgggcttct cttcctccac ctctttgccc tgatgcgggc ggcaggcctg     2700
cctgagctca gctgctccaa agacatccag tatctcaagg actccctggc actggggaaa     2760
acagaggagg aggcactgaa gcacttccga gtgaagttta cgaagccct ccgtgagagc      2820 tggaaaaacca aagtgaactg gctggcccac aacgtgtcca agacaacag gcagtag       2877
```

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
acatgtggcc cctctcctg                                                      19

<210> SEQ ID NO 16
<211> LENGTH: 1836
<212> TYPE: DNA
<213> ORGANISM: Homo sapiens

<400> SEQUENCE: 16

| | | |
|---|---|---|
| atgcccctg gggtggactg cccatggaa ttctggacca aggaggagaa tcagagcgtt | 60 |
| gtggttgact tcctgctgcc cacaggggtc tacctgaact tccctgtgtc ccgcaatgcc | 120 |
| aacctcagca ccatcaagca gctgctgtgg caccgcgccc agtatgagcc gctcttccac | 180 |
| atgctcagtg gccccgaggc ctatgtgttc acctgcatca accagacagc ggagcagcaa | 240 |
| gagctggagg acgagcaacg cgtctgtgt gacgtgcagc ccttcctgcc cgtcctgcgc | 300 |
| ctggtggccc gtgagggcga ccgcgtgaag aagctcatca actcacagat cagcctcctc | 360 |
| atcggcaaag gcctccacga gtttgactcc ttgtgcgacc cagaagtgaa cgactttcgc | 420 |
| gccaagatgt gccaattctg cgaggaggcg ccgcccgcc ggcagcagct gggctgggag | 480 |
| gcctggctgc agtacagttt cccctgcag ctggagccct cggctcaaac ctgggggcct | 540 |
| ggtaccctgc ggctcccgaa ccgggcccctt ctggtcaacg ttaagtttga gggcagcgag | 600 |
| gagagcttca ccttccaggt gtccaccaag gacgtgccgc tggcgctgat ggcctgtgcc | 660 |
| ctgcggaaga aggccacagt gttccggcag ccgctggtgg agcagccgga agactacacg | 720 |
| ctgcaggtga acggcaggca tgagtacctg tatggcagct cccgctctg ccagttccag | 780 |
| tacatctgca gctgcctgca cagtgggttg acccctcacc tgaccatggt ccattcctcc | 840 |
| tccatcctcg ccatgcggga tgagcagagc aaccctgccc ccaggtcca gaaaccgcgt | 900 |
| gccaaaccac ctcccattcc tgcgaagaag ccttcctctg tgtccctgtg gtccctggag | 960 |
| cagccgttcc gcatcgagct catccagggc agcaaagtga acgccgacga gcggatgaag | 1020 |
| ctggtggtgc aggccgggct ttccacggc aacgagatgc tgtgcaagac ggtgtccagc | 1080 |
| tcggaggtga gcgtgtgctc ggagcccgtg tggaagcagc ggctggagtt cgacatcaac | 1140 |
| atctgcgacc tgccccgcat ggcccgtctc tgctttgcgc tgtacgccgt gatcgagaaa | 1200 |
| gccaagaagg ctcgctccac caagaagaag tccaagaagg cggactgccc cattgcctgg | 1260 |
| gccaacctca tgctgtttga ctacaaggac cagcttaaga ccggggaacg ctgcctctac | 1320 |
| atgtggcccc tctcctgtgc tggctattgt gtggccacat atgtgctggg cattggcgat | 1380 |
| cggcacagcg acaacatcat gatccgagag agtgggcagc tgttccacat tgattttggc | 1440 |
| cactttctgg ggaatttcaa gaccaagttt ggaatcaacc gcgagcgtgt cccattcatc | 1500 |
| ctcacctacg actttgtcca tgtgattcag cagggagaac taataatag tgagaaattt | 1560 |
| gaacggttcc ggggctactg tgaaagggcc tacaccatcc tgcggcgcca cgggcttctc | 1620 |
| ttcctccacc tctttgcccct gatgcgggcg caggcctgc tgagctcag ctgctccaaa | 1680 |
| gacatccagt atctcaagga ctccctggca ctggggaaaa cagaggagga ggcactgaag | 1740 |

```
cacttccgag tgaagtttaa cgaagccctc cgtgagagct ggaaaaccaa agtgaactgg    1800
ctggcccaca acgtgtccaa agacaacagg cagtag                              1836

<210> SEQ ID NO 17
<211> LENGTH: 19
<212> TYPE: RNA
<213> ORGANISM: Artificial Sequence
<220> FEATURE:
<223> OTHER INFORMATION: Synthetic

<400> SEQUENCE: 17
ccucuccugu gcuggcuau                                                 19

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
auagccagca caggagagg                                                 19

<210> SEQ ID NO 19
<211> LENGTH: 2421
<212> TYPE: DNA
<213> ORGANISM: Homo sapiens

<400> SEQUENCE: 19
atgggcgccc ctgcctgcgc cctcgcgctc tgcgtggccg tggccatcgt ggccggcgcc    60
tcctcggagt ccttggggac ggagcagcgc gtcgtggggc gagcggcaga agtcccgggc    120
ccagagcccg gccagcagga gcagttggtc ttcggcagcg gggatgctgt ggagctgagc    180 tgtccccgc cgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag acggcgggcg ctaacaccac cgacaaggag    960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200 cccccaaga aaggcctggg ctcccccacc gtgcacaaga tctcccgctt cccgctcaag    1260
cgacaggtgt ccctggagtc caacgcgtcc atgagctcca acacaccact ggtgcgcatc    1320
```

```
gcaaggctgt cctcagggga gggccccacg ctggccaatg tctccgagct cgagctgcct    1380
gccgacccca aatgggagct gtctcgggcc cggctgaccc tgggcaagcc ccttggggag    1440
ggctgcttcg gccaggtggt catggcggag ccatcggca ttgacaagga ccgggccgcc     1500
aagcctgtca ccgtagccgt gaagatgctg aaagacgatg ccactgacaa ggacctgtcg    1560
gacctggtgt ctgagatgga gatgatgaag atgatcggga aacacaaaaa catcatcaac    1620
ctgctgggcg cctgcacgca gggcgggccc ctgtacgtgc tggtggagta cgcggccaag    1680
ggtaacctgc gggagtttct gcgggcgcgg cggcccccgg gcctggacta ctccttcgac    1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggccgg    1920 gacgtgcaca acctcgacta ctacaagaag acgaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg gggggctccc cgtaccccgg catccctgtg    2100
gaggagctct tcaagctgct gaaggagggc accgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgcccccggc cccacccagc    2400
agtgggggct cgcggacgtg a                                              2421

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
acaacgtgat gaagatcgca                                                 20

<210> SEQ ID NO 21
<211> LENGTH: 19
<212> TYPE: DNA
<213> ORGANISM: Artificial Sequence
<220> FEATURE:
<223> OTHER INFORMATION: Synthetic

<400> SEQUENCE: 21
aggtcgtgtg tgcagttgg                                                  19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
cucgacuacu acaagaaga                                                  19

<210> SEQ ID NO 23
<211> LENGTH: 19
<212> TYPE: RNA
```

<213> ORGANISM: Artificial Sequence
<220> FEATURE:
<223> OTHER INFORMATION: Synthetic

<400> SEQUENCE: 23
ucuucuugua guagucgag        19

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
ttggcctccc agaagggccg gct        23

<210> SEQ ID NO 25
<211> LENGTH: 2298
<212> TYPE: DNA
<213> ORGANISM: Homo sapiens

<400> SEQUENCE: 25

```
atgggcgccc ctgcctgcgc cctcgcgctc tgcgtggccg tggccatcgt ggccggcgcc        60
tcctcggagt ccttggggac ggagcagcgc gtcgtggggc gagcggcaga agtcccgggc       120
ccagagcccg gccagcagga gcagttggtc ttcggcagcg gggatgctgt ggagctgagc       180
tgtccccgc cggggggtgg tcccatgggg cccactgtct gggtcaagga tggcacaggg       240
ctggtgccct cggagcgtgt cctggtgggg ccccagcggc tgcaggtgct gaatgcctcc       300
cacgaggact ccggggccta cagctgccgg cagcggctca cgcagcgcgt actgtgccac       360
ttcagtgtgc gggtgacaga cgctccatcc tcgggagatg acgaagacgg ggaggacgag       420
gctgaggaca caggtgtgga cacaggggcc ccttactgga cacggcccga gcggatggac       480
aagaagctgc tggccgtgcc ggccgccaac accgtccgct tccgctgccc agccgctggc       540
aaccccactc cctccatctc ctggctgaag aacggcaggg agttccgcgg cgagcaccgc       600
attggaggca tcaagctgcg gcatcagcag tggagcctgg tcatggaaag cgtggtgccc       660
tcggaccgcg gcaactacac ctgcgtcgtg gagaacaagt ttggcagcat ccggcagacg       720
tacacgctgg acgtgctgga cgctcccccg caccggccca tcctgcaggc ggggctgccg       780
gccaaccaga cggcggtgct gggcagcgac gtggagttcc actgcaaggt gtacagtgac       840
gcacagcccc acatccagtg gctcaagcac gtggaggtga atggcagcaa ggtgggcccg       900
gacggcacac cctacgttac cgtgctcaag acggcgggcg ctaacaccac cgacaaggag       960
ctagaggttc tctccttgca aacgtcacc tttgaggacg ccggggagta cacctgcctg      1020
gcgggcaatt ctattgggtt ttctcatcac tctgcgtggc tggtggtgct gccagccgag      1080
gaggagctgg tggaggctga cgaggcgggc agtgtgtatg caggcatcct cagctacggg      1140
gtgggcttct tcctgttcat cctggtggtg gcggctgtga cgctctgccg cctgcgcagc      1200
cccccaagaa aaggcctggg ctcccccacc gtgcacaaga tctcccgctt cccgctcaag      1260
cgacaggtgt ccctggagtc caacgcgtcc atgagctcca acacaccact ggtgcgcatc      1320
gcaaggctgt cctcagggga gggcccacg ctggccaatg tctccgagct cgagctgcct      1380
gccgacccca aatgggagct gtctcgggcc cggctgaccc tgggcaagcc ccttggggag      1440
ggctgcttcg gccaggtggt catggcggag gccatcggca ttgacaagga ccgggccgcc      1500
aagcctgtca ccgtagccgt gaagatgctg aaagacgatg ccactgacaa ggacctgtcg      1560
```

-continued

| | | | |
|---|---|---|---|
| gacctggtgt ctgagatgga gatgatgaag atgatcggga aacacaaaaa catcatcaac | | | 1620 |
| ctgctgggcg cctgcacgca gggcgggccc ctgtacgtgc tggtggagta cgcggccaag | | | 1680 |
| ggtaacctgc gggagtttct gcgggcgcgg cggcccccgg gcctggacta ctccttcgac | | | 1740 |
| acctgcaagc cgcccgagga gcagctcacc ttcaaggacc tggtgtcctg tgcctaccag | | | 1800 |
| gtggcccggg gcatggagta cttggcctcc cagaagggcc ggctgcccgt gaagtggatg | | | 1860 |
| gcgcctgagg ccttgtttga ccgagtctac actcaccaga gtgacgtctg gtcctttggg | | | 1920 |
| gtcctgctct gggagatctt cacgctgggg ggctccccgt accccggcat ccctgtggag | | | 1980 |
| gagctcttca gctgctgaa ggagggccac cgcatggaca gcccgccaa ctgcacacac | | | 2040 |
| gacctgtaca tgatcatgcg ggagtgctgg catgccgcgc cctcccagag gcccaccttc | | | 2100 |
| aagcagctgg tggaggacct ggaccgtgtc cttaccgtga cgtccaccga cgagtacctg | | | 2160 |
| gacctgtcgg cgcctttcga gcagtactcc ccgggtggcc aggacacccc cagctccagc | | | 2220 |
| tcctcagggg acgactccgt gtttgcccac gacctgctgc cccggccc acccagcagt | | | 2280 |
| gggggctcgc ggacgtga | | | 2298 |

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26

| | |
|---|---|
| ccucccagaa gggccggcu | 19 |

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27

| | |
|---|---|
| agccggcccu ucugggagg | 19 |

<210> SEQ ID NO 28
<211> LENGTH: 5424
<212> TYPE: DNA
<213> ORGANISM: Homo sapiens

<400> SEQUENCE: 28

| | | | |
|---|---|---|---|
| atggccaaac caacaagcaa agattcaggc ttgaaggaga agtttaagat tctgttggga | | | 60 |
| ctgggaacac cgaggccaaa tcccaggtct gcagagggta acagacgga gtttatcatc | | | 120 |
| accgcggaaa tactgagaga actgagcatg gaatgtggcc tcaacaatcg catccggatg | | | 180 |
| ataggggcaga tttgtgaagt cgcaaaaacc aagaaatttg aagagcacgc agtggaagca | | | 240 |
| ctctggaagg cggtcgcgga tctgttgcag ccggagcggc cgctggaggc ccggcacgcg | | | 300 |
| gtgctggctc tgctgaaggc catcgtgcag gggcagggcg agcgtttggg ggtcctcaga | | | 360 |
| gccctcttct ttaaggtcat caaggattac ccttccaacg aagaccttca cgaaaggctg | | | 420 |
| gaggttttca aggccctcac agacaatggg agacacatca cctacttgga ggaagagctg | | | 480 |
| gctgactttg tcctgcagtg gatggatgtt ggcttgtcct cggaattcct tctggtgctg | | | 540 |
| gtgaacttgg tcaaattcaa tagctgttac ctcgacgagt acatcgcaag gatggttcag | | | 600 |

-continued

```
atgatctgtc tgctgtgcgt ccggaccgcg tcctctgtgg acatagaggt ctccctgcag    660
gtgctggacg ccgtggtctg ctacaactgc ctgccggctg agagcctccc gctgttcatc    720
gttaccctct gtcgcaccat caacgtcaag gagctctgcg agccttgctg gaagctgatg    780
cggaacctcc ttggcaccca cctgggccac agcgccatct acaacatgtg ccacctcatg    840
gaggacagag cctacatgga ggacgcgccc ctgctgagag agccgtgtt ttttgtgggc     900
atggctctct ggggagccca ccggctctat tctctcagga actcgccgac atctgtgttg    960
ccatcatttt accaggccat ggcatgtccg aacgaggtgg tgtcctatga gatcgtcctg   1020
tccatcacca ggctcatcaa gaagtatagg aaggagctcc aggtggtggc gtgggacatt   1080
ctgctgaaca tcatcgaacg gctccttcag cagctccaga ccttggacag cccggagctc   1140
aggaccatcg tccatgacct gttgaccacg gtggaggagc tgtgtgacca gaacgagttc   1200
cacgggtctc aggagagata cttttgaactg gtggagagat gtgcggacca gaggcctgag  1260
tcctccctcc tgaacctgat tcctataga gcgcagtcca tccacccggc caaggacggc    1320
tggattcaga acctgcaggc gctgatggag agattcttca ggagcgagtc ccgaggcgcc   1380
gtgcgcatca aggtgctgga cgtgctgtcc tttgtgctgc tcatcaacag gcagttctat   1440
gaggaggagc tgattaactc agtggtcatc tcgcagctct cccacatccc cgaggataaa   1500
gaccaccagg tccgaaagct ggccacccag ttgctggtgg acctggcaga gggctgccac   1560
acacaccact tcaacagcct gctggacatc atcgagaagg tgatggcccg ctccctctcc   1620
ccaccccggg agctggaaga aagggatgtg ccgcatact cggcctcctt ggaggatgtg    1680
aagacagccg tcctggggct tctggtcatc cttcagacca gctgtacac cctgcctgca    1740
agccacgcca cgcgtgtgta tgagatgctg gtcagccaca ttcagctcca ctacaagcac   1800
agctacaccc tgccaatcgc gagcagcatc cggctgcagg cctttgactt cctgttgctg   1860
ctgcgggccg actcactgca ccgcctgggc ctgcccaaca aggatggagt cgtgcggttc   1920
agcccctact gcgtctgcga ctacatggag ccagagagag gctctgagaa aagaccagc    1980
ggccccttt ctcctcccac agggcctcct ggccggcgc ctgcaggccc gccgtgcgg      2040
ctggggtccg tgccctactc cctgctcttc cgcgtcctgc tgcagtgctt gaagcaggag   2100
tctgactgga aggtgctgaa gctggttctg ggcaggctgc ctgagtccct gcgctataaa   2160
gtgctcatct ttacttcccc ttgcagtgtg accagctgt gctctgctct ctgctccatg    2220
ctttcaggcc caaagacact ggagcggctc cgaggcgccc cagaaggctt ctccagaact   2280
gacttgcacc tggccgtggt tccagtgctg acagcattaa tctcttacca taactacctg   2340
gacaaaacca acagcgcga tggtctac tgcctggagc agggcctcat ccaccgctgt      2400
gccagccagt gcgtcgtggc cttgtccatc tgcagcgtgg agatgcctga catcatcatc   2460
aaggcgctgc ctgttctggt ggtgaagctc acgcacatct cagccacagc cagcatggcc   2520
gtcccactgc tggagttcct gtccactctg gccaggctgc cgcacctcta caggaacttt   2580
gccgcggagc agtatgccag tgtgttcgcc atctccctgc cgtacaccaa cccctccaag   2640
tttaatcagt acatcgtgtg tctggcccat cacgtcatag ccatgtggtt catcaggtgc   2700
cgcctgcccc tccggaagga ttttgtccct ttcatcacta agggcctgcg gtccaatgtc   2760
ctcttgtctt ttgatgacac ccccgagaag gacagcttca gggcccggag tactagtctc   2820
aacgagagac ccaagagtct gaggatagca gaccccccca acaaggctt gaataactct    2880
ccacccgtga agaattcaa ggagagctct gcagccgagg ccttccggtg ccgcagcatc    2940
agtgtgtctg aacatgtggt ccgcagcagg atacagacgt ccctcaccag tgccagcttg   3000
```

```
gggtctgcag atgagaactc cgtggcccag gctgacgata gcctgaaaaa cctccacctg    3060
gagctcacgg aaacctgtct ggacatgatg gctcgatacg tcttctccaa cttcacggct    3120
gtcccgaaga ggtctcctgt gggcgagttc ctcctagcgg gtggcaggac caaaacctgg    3180
ctggttggga acaagcttgt cactgtgacg acaagcgtgg gaaccgggac ccggtcgtta    3240
ctaggcctgg actcggggga gctgcagtcc ggcccggagt cgagctccag ccccggggtg    3300
catgtgagac agaccaagga ggcgccggcc aagctggagt cccaggctgg gcagcaggtg    3360
tcccgtgggg cccgggatcg ggtccgttcc atgtcggggg ccatggtct tcgagttggc     3420 gccctggacg tgccggcctc ccagttcctg ggcagtgcca cttctccagg accacggact    3480
gcaccagccg cgaaacctga gaaggcctca gctggcaccc gggttcctgt gcaggagaag    3540
acgaacctgg cggcctatgt gcccctgctg acccagggct gggcggagat cctggtccgg    3600
aggcccacag gaacaccag ctggctgatg agcctggaga acccgctcag cccttttctcc     3660 tcggacatca acaacatgcc cctgcaggag ctgtctaacg ccctcatggc ggctgagcgc    3720
ttcaaggagc accgggacac agccctgtac aagtcactgt cggtgccggc agccagcacg    3780
gccaaacccc ctcctctgcc tcgctccaac acagtggcct ctttctcctc cctgtaccag    3840
tccagctgcc aaggacagct gcacaggagc gtttcctggg cagactccgc cgtggtcatg    3900
gaggagggaa gtccgggcga ggttcctgtg ctggtggagc ccccagggtt ggaggacgtt    3960
gaggcagcgc taggcatgga caggcgcacg gatgcctaca gcaggtcgtc ctcagtctcc    4020
agccaggagg agaagtcgct ccacgcggag gagctggttg gcaggggcat ccccatcgag    4080
cgagtcgtct cctcggaggg tggccggccc tctgtggacc tctccttcca gccctcgcag    4140
cccctgagca gtccagctc ctctcccgag ctgcagactc tgcaggacat cctcggggac      4200
cctggggaca aggccgacgt gggccggctg agccctgagg ttaaggcccg gtcacagtca    4260
gggaccctgg acggggaaag tgctgcctgg tcggcctcgg gcgaagacag tcggggccag    4320
cccgagggtc ccttgccttc cagctccccc cgctcgccca gtggcctccg gccccgaggt    4380
tacaccatct ccgactcggc cccatcacgc aggggcaaga gagtagagag ggacgccttta   4440 aagagcagag ccacagcctc caatgcagag aaagtgccag gcatcaaccc cagtttcgtg    4500
ttcctgcagc tctaccattc ccccttcttt ggcgacgagt caaacaagcc aatcctgctg    4560
cccaatgagt cacagtcctt tgagcggtcg gtgcagctcc tcgaccagat ccatcatac      4620 gacacccaca agatcgccgt cctgtatgtt ggagaaggcc agagcaacag cgagctcgcc    4680
atcctgtcca atgagcatgg ctcctacagg tacacggagt tcctgacggg cctgggccgg    4740
ctcatcgagc tgaaggactg ccagccggac aaggtgtacc tgggaggcct ggacgtgtgt    4800
ggtgaggacg gccagttcac ctactgctgg cacgatgaca tcatgcaagc cgtcttccac    4860
atcgccaccc tgatgcccac caaggacgtg gacaagcacc gctgcgacaa gaagcgccac    4920
ctgggcaacg actttgtgtc cattgtctac aatgactccg gtgaggactt caagcttggc    4980
accatcaagg gccagttcaa ctttgtccac gtgatcgtca cccgctggga ctacgagtgc    5040
aacctggtgt ccctgcagtg caggaaagac atggagggcc ttgtggacac cagcgtggcc    5100
aagatcgtgt ctgaccgcaa cctgcccttc gtggcccgcc agatgccct gcacgcaaat     5160 atggcctcac aggtgcatca tagccgctcc aaccccaccg atatctaccc ctccaagtgg    5220
attgcccggc tccgccacat caagcggctc cgccagcgga tctgcgagga agccgcctac    5280 tccaaccccca gcctacctct ggtgcaccct ccgtcccata gcaaagcccc tgcacagact   5340
```

```
ccagccgagc ccacacctgg ctatgaggtg ggccagcgga agcgcctcat ctcctcggtg    5400
gaggacttca ccgagtttgt gtga                                           5424
```

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29

```
tttgacttcc tgttgctgct                                                  20
```

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30

```
tgagcacttt atagcgcag                                                   19
```

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31

```
cugcgcuaua aagugcuca                                                   19
```

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32

```
ugagcacuuu auagcgcag                                                   19
```

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33

```
cttgaagcag ctttcaggcc                                                  20
```

<210> SEQ ID NO 34
<211> LENGTH: 5301
<212> TYPE: DNA
<213> ORGANISM: Homo sapiens

<400> SEQUENCE: 34

```
atggccaaac caacaagcaa agattcaggc ttgaaggaga agtttaagat tctgttggga      60
ctgggaacac cgaggccaaa tcccaggtct gcagagggta aacagacgga gtttatcatc     120 accgcgaaa tactgagaga actgagcatg gaatgtggcc tcaacaatcg catccggata     180
atagggcaga tttgtgaagt cgcaaaaacc aagaaatttg aagagcacgc agtggaagca     240
```

```
ctctggaagg cggtcgcgga tctgttgcag ccggagcggc cgctggaggc ccggcacgcg   300
gtgctggctc tgctgaaggc catcgtgcag gggcagggcg agcgtttggg ggtcctcaga   360
gccctcttct ttaaggtcat caaggattac ccttccaacg aagaccttca cgaaaggctg   420
gaggttttca aggccctcac agacaatggg agacacatca cctacttgga ggaagagctg   480
gctgactttg tcctgcagtg gatggatgtt ggcttgtcct cggaattcct tctggtgctg   540
gtgaacttgg tcaaattcaa tagctgttac ctcgacgagt acatcgcaag gatggttcag   600
atgatctgtc tgctgtgcgt ccggaccgcg tcctctgtgg acatagaggt ctccctgcag   660
gtgctggacg ccgtggtctg ctacaactgc ctgccggctg agagcctccc gctgttcatc   720
gttaccctct gtcgcaccat caacgtcaag gagctctgcg agccttgctg gaagctgatg   780
cggaacctcc ttggcaccca cctgggccac agcgccatct acaacatgtg ccacctcatg   840
gaggacagag cctacatgga ggacgcgccc ctgctgagag gagccgtgtt ttttgtgggc   900
atggctctct ggggagccca ccggctctat tctctcagga actcgccgac atctgtgttg   960
ccatcatttt accaggccat ggcatgtccg aacgaggtgg tgtcctatga gatcgtcctg  1020
tccatcacca ggctcatcaa gaagtatagg aaggagctcc aggtggtggc gtgggacatt  1080
ctgctgaaca tcatcgaacg gctccttcag cagctccaga ccttggacag cccggagctc  1140
aggaccatcg tccatgacct gttgaccacg gtggaggagc tgtgtgacca gaacgagttc  1200
cacgggtctc aggagagata ctttgaactg gtggagagat gtgcggacca gaggcctgag  1260
tcctccctcc tgaacctgat ctcctataga gcgcagtcca tccacccggc caaggacggc  1320
tggattcaga acctgcaggc gctgatggag agattcttca ggagcgagtc ccgaggcgcc  1380
gtgcgcatca aggtgctgga cgtgctgtcc tttgtgctgc tcatcaacag gcagttctat  1440
gaggaggagc tgattaactc agtggtcatc tcgcagctct cccacatccc cgaggataaa  1500
gaccaccagg tccgaaagct ggccacccag ttgctggtgg acctggcaga gggctgccac  1560
acacaccact tcaacagcct gctggacatc atcgagaagg tgatggcccg ctccctctcc  1620 ccaccccgg agctgaaaga aagggatgtg ccgcatatact cggcctcctt ggaggatgtg  1680
aagacagccg tcctggggct tctggtcatc ctttcagacca agctgtacac cctgcctgca  1740
agccacgcca cgcgtgtgta tgagatgctg tcagccaca ttcagctcca ctacaagcac  1800
agctacaccc tgccaatcgc gagcagcatc cggctgcagg cctttgactt cctgttgctg  1860
ctgcgggccg actcactgca ccgcctgggc ctgcccaaca aggatggagt cgtgcggttc  1920
agcccctact gcgtctgcga ctacatggag ccagagagag gctctgagaa aagaccagc  1980 ggccccttt ctcctcccac agggcctcct ggccggcgc ctgcaggccc gccgtgcgg  2040 ctggggtccg tgccctactc cctgctcttc cgcgtcctgc tgcagtgctt gaagcagctt  2100
tcaggcccaa agacactgga gcggctccga ggcgcccag aaggcttctc cagaactgac  2160
ttgcacctgg ccgtggttcc agtgctgaca gcattaatct cttaccataa ctacctggac  2220
aaaaccaaac agcgcgagat ggtctactgc ctggagcagg gcctcatcca ccgctgtgcc  2280
agccagtgcg tctggccctt gtccatctgc agcgtggaga tgcctgacat catcatcaag  2340
gcgctgcctg ttctggtggt gaagctcacg cacatctcag ccacagccag catggccgtc  2400
ccactgctgg agttcctgtc cactctggcc aggctgccgc acctctacag gaactttgcc  2460
gcggagcagt atgccagtgt gttcgccatc tccctgccgt acaccaaccc ctccaagttt  2520
aatcagtaca tcgtgtgtct ggcccatcac gtcatagcca tgtggttcat caggtgccgc  2580
```

```
ctgcccttcc ggaaggattt tgtcccttc atcactaagg gcctgcggtc caatgtcctc    2640
ttgtcttttg atgacacccc cgagaaggac agcttcaggg cccggagtac tagtctcaac    2700
gagagaccca agagtctgag gatagccaga cccccaaac aaggcttgaa taactctcca     2760
cccgtgaaag aattcaagga gagctctgca gccgaggcct tccggtgccg cagcatcagt    2820
gtgtctgaac atgtggtccg cagcaggata cagacgtccc tcaccagtgc cagcttgggg    2880
tctgcagatg agaactccgt ggcccaggct gacgatagcc tgaaaaacct ccacctggag    2940
ctcacggaaa cctgtctgga catgatggct cgatacgtct tctccaactt cacggctgtc    3000
ccgaagaggt ctcctgtggg cgagttcctc ctagcgggtg gcaggaccaa aacctggctg    3060
gttgggaaca agcttgtcac tgtgacgaca agcgtgggaa ccgggacccg gtcgttacta    3120
ggcctggact cggggagct gcagtccggc ccggagtcga gctccagccc cggggtgcat     3180
gtgagacaga ccaaggaggc gccggccaag ctggagtccc aggctgggca gcaggtgtcc    3240
cgtggggccc gggatcggt ccgttccatg tcggggggcc atggtcttcg agttggcgcc     3300
ctggacgtgc cggcctccca gttcctgggc agtgccactt ctccaggacc acggactgca    3360
ccagccgcga aacctgagaa ggcctcagct ggcacccggg ttcctgtgca ggagaagacg    3420
aacctggcgg cctatgtgcc cctgctgacc cagggctggg cggagatcct ggtccggagg    3480
cccacaggga acaccagctg gctgatgagc ctggagaacc cgctcagccc tttctcctcg    3540
gacatcaaca acatgcccct gcaggagctg tctaacgccc tcatggcggc tgagcgcttc    3600
aaggagcacc gggacacagc cctgtacaag tcactgtcgg tgccggcagc cagcacggcc    3660
aaaccccctc ctctgcctcg ctccaacaca gtggcctctt tctcctccct gtaccagtcc    3720
agctgccaag acagctgca caggagcgtt tcctgggcag actccgccgt ggtcatggag    3780
gagggaagtc cgggcgaggt tcctgtgctg gtggagcccc cagggttgga ggacgttgag    3840
gcagcgctag gcatggacag gcgcacggat gcctacagca ggtcgtcctc agtctccagc    3900
caggaggaga agtcgctcca cgcggaggag ctggttggca ggggcatccc catcgagcga    3960
gtcgtctcct cggagggtgg ccggccctct gtggacctct ccttccagcc ctcgcagccc    4020
ctgagcaagt ccagctcctc tcccgagctg cagactctgc aggacatcct cggggaccct    4080
ggggacaagg ccgacgtggg ccggctgagc cctgaggtta aggcccggtc acagtcaggg    4140
accctggacg gggaaagtgc tgcctggtcg gcctcgggcg aagacagtcg gggccagccc    4200
gagggtccct tgccttccag ctcccccgc tcgcccagtg gctccggcc ccgaggttac     4260
accatctccg actcggcccc atcacgcagg ggcaagagag tagagaggga cgccttaaag    4320
agcagagcca cagcctccaa tgcagagaaa gtgccaggca tcaaccccag tttcgtgttc    4380
ctgcagctct accattcccc cttctttggc gacgagtcaa acaagccaat cctgctgccc    4440
aatgagtcac agtcctttga gcggtcggtg cagctcctcg accagatccc atcatacgac    4500
acccacaaga tcgccgtcct gtatgttgga gaaggccaga gcaacagcga gctcgccatc    4560
ctgtccaatg agcatggctc ctacaggtac acggagttcc tgacgggcct gggccggctc    4620
atcgagctga aggactgcca gccggacaag gtgtacctgg aggcctgga cgtgtgtggt     4680
gaggacggcc agttcaccta ctgctggcac gatgacatca tgcaagccgt cttccacatc    4740
gccaccctga tgcccaccaa ggacgtggac aagcaccgct gcgacaagaa gcgccacctg    4800
ggcaacgact ttgtgtccat tgtctacaat gactccggtg aggacttcaa gcttggcacc    4860
atcaagggca agttcaactt tgtccacgtg atcgtcaccc cgctggacta cgagtgcaac    4920
ctggtgtccc tgcagtgcag gaaagacatg gagggccttg tggacaccag cgtggccaag    4980
```

```
atcgtgtctg accgcaacct gcccttcgtg gcccgccaga tggccctgca cgcaaatatg    5040
gcctcacagg tgcatcatag ccgctccaac cccaccgata tctacccctc caagtggatt    5100
gcccggctcc gccacatcaa gcggctccgc cagcggatct gcgaggaagc cgcctactcc    5160
aaccccagcc tacctctggt gcaccctccg tcccatagca aagcccctgc acagactcca    5220
gccgagccca cacctggcta tgaggtgggc cagcggaagc gcctcatctc ctcggtggag    5280
gacttcaccg agtttgtgtg a                                              5301

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
gaagcagcuu ucaggccca                                                 19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
ugggccugaa agcugcuuc                                                 19

<210> SEQ ID NO 37
<211> LENGTH: 1830
<212> TYPE: DNA
<213> ORGANISM: Homo sapiens

<400> SEQUENCE: 37
atggcaggca ccctggacct ggacaagggc tgcacggtgg aggagctgct ccgcgggtgc      60
atcgaagcct tcgatgactc cgggaaggtg cgggacccgc agctggtgcg catgttcctc     120
atgatgcacc cctggtacat cccctcctct cagctgcgg ccaagctgct ccacatctac     180
caacaatccc ggaaggacaa ctccaattcc ctgcaggtga aaacgtgcca cctggtcagg     240
tactggatct ccgccttccc agcggagttt gacttgaacc cggagttggc tgagcagatc     300
aaggagctga aggctctgct agaccaagaa gggaaccgac ggcacagcag cctaatcgac     360
atagacagcg tccctaccta caagtggaag cggcaggtga ctcagcggaa ccctgtggga     420
cagaaaaagc gcaagatgtc cctgttgttt gaccacctgg agcccatgga gctggcggag     480
catctcaccc acttggagta tcgctccttc tgcaagatcc tgtttcagga ctatacagt     540 ttcgtgactc atggctgcac tgtggacaac cccgtcctgg agcggttcat ctccctcttc     600
aacagcgtct cacagtgggt gcagctcatg atcctcagca aacccacagc cccgcagcgg     660
gccctggtca tcacacactt tgtccacgtg gcggagaagc tgctacagct gcagaacttc     720
aacacgctga tggcagtggt cggggggcctg agccacagct ccatctcccg cctcaaggag     780
acccacagcc acgttagccc tgagaccatc aagctctggg agggtctcac ggaactagtg     840
acggcgacag gcaactatgg caactaccgg cgtcggctgg cagcctgtgt gggcttccgc     900
ttcccgatcc tgggtgtgca cctcaaggac ctggtggccc tgcagctggc actgcctgac     960
tggctggacc cagcccggac ccggctcaac ggggccaaga tgaagcagct ctttagcatc    1020
```

```
ctggaggagc tggccatggt gaccagcctg cggccaccag tacaggccaa ccccgacctg    1080
ctgagcctgc tcacggtgtc tctggatcag tatcagacgg aggatgagct gtaccagctg    1140
tccctgcagc gggagccgcg ctccaagtcc tcgccaacca gccccacgag ttgcacccca    1200 ccacccggc ccccggtact ggaggagtgg acctcggctg ccaaacccaa gctggatcag    1260
gccctcgtgg tggagcacat cgagaagatg gtggagtctg tgttccggaa cttttgacgtc    1320 gatggggatg ccacatctc acaggaagaa ttccagatca tccgtgggaa cttcccttac    1380
ctcagcgcct ttggggacct cgaccagaac caggatggct gcatcagcag ggaggagatg    1440
gtttcctatt tcctgcgctc cagctctgtg ttgggggggc gcatgggctt cgtacacaac    1500
ttccaggaga gcaactcctt cgccccgtc gcctgccgcc actgcaaagc cctgatcctg    1560
ggcatctaca gcagggcct caaatgccga gcctgtggag tgaactgcca caagcagtgc    1620
aaggatcgcc tgtcagttga gtgtcggcgc agggcccaga gtgtgagcct ggagggtct    1680 gcaccctcac cctcacccat gcacagccac catcaccgcg ccttcagctt ctctctgccc    1740
cgccctggca ggcgaggctc caggcctcca gagatccgtg aggaggaggt acagacggtg    1800
gaggatgggg tgtttgacat ccacttgtaa                                     1830

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
tcacggtgtc tctggatcag t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
ccaccatctt ctcgatgtgc t                                              21

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
guggagcaca ucgagaaga                                                 19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
ucuucucgau gugcuccac                                                 19

<210> SEQ ID NO 42
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 42
ccacaucuca caggaagaa                                                  19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
uucuuccugu gagaugugg                                                  19

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
caagtcctcg tctgtgttcc                                                 20

<210> SEQ ID NO 45
<211> LENGTH: 1707
<212> TYPE: DNA
<213> ORGANISM: Homo sapiens

<400> SEQUENCE: 45
atggcaggca ccctggacct ggacaagggc tgcacggtgg aggagctgct ccgcgggtgc     60
atcgaagcct tcgatgactc cgggaaggtg cgggacccgc agctggtgcg catgttcctc    120
atgatgcacc cctggtacat ccctcctct cagctggcgg ccaagctgct ccacatctac    180
caacaatccc ggaaggacaa ctccaattcc ctgcaggtga aaacgtgcca cctggtcagg    240
tactggatct ccgccttccc agcggagttt gacttgaacc cggagttggc tgagcagatc    300
aaggagctga aggctctgct agaccaagaa gggaaccgac ggcacagcag cctaatcgac    360
atagacagcg tccctaccta caagtggaag cggcaggtga ctcagcggaa ccctgtggga    420
cagaaaaagc gcaagatgtc cctgttgttt gaccacctgg agcccatgga gctggcggag    480
catctcaccc acttggagta tcgctccttc tgcaagatcc tgtttcagga ctatcacagt    540
ttcgtgactc atggctgcac tgtggacaac cccgtcctgg agcggttcat ctccctcttc    600
aacagcgtct cacagtgggt gcagctcatg atcctcagca aacccacagc cccgcagcgg    660
gccctggtca tcacacactt tgtccacgtg gcggagaagc tgctacagct gcagaacttc    720
aacacgctga tggcagtggt cggggggcctg agccacagct ccatctcccg cctcaaggag    780
acccacagcc acgttagccc tgagaccatc aagctctggg agggtctcac ggaactagtg    840
acggcgacag gcaactatgg caactaccgg cgtcggctgg cagcctgtgt gggcttccgc    900
ttcccgatcc tgggtgtgca cctcaaggac ctggtgcccc tgcagctggc actgcctgac    960
tggctggacc cagcccggac ccggctcaac ggggccaaga tgaagcagct ctttagcatc   1020
ctggaggagc tggccatggt gaccagcctg cggccaccag tacaggccaa ccccgacctg   1080
ctgagcctgc tcacggtgtc tctggatcag tatcagacgg aggatgagct gtaccagctg   1140
```

| | |
|---|---|
| tccctgcagc gggagccgcg ctccaagtcc tcgtctgtgt tccggaactt tgacgtcgat | 1200 |
| ggggatggcc acatctcaca ggaagaattc cagatcatcc gtgggaactt cccttacctc | 1260 |
| agcgcctttg gggacctcga ccagaaccag gatggctgca tcagcaggga ggagatggtt | 1320 |
| tcctatttcc tgcgctccag ctctgtgttg gggggcgca tgggcttcgt acacaacttc | 1380 |
| caggagagca actccttgcg ccccgtcgcc tgccgccact gcaaagccct gatcctgggc | 1440 |
| atctacaagc agggcctcaa atgccgagcc tgtggagtga actgccacaa gcagtgcaag | 1500 |
| gatcgcctgt cagttgagtg tcggcgcagg gcccagagtg tgagcctgga ggggtctgca | 1560 |
| ccctcaccct cacccatgca cagccaccat caccgcgcct tcagcttctc tctgccccgc | 1620 |
| cctggcaggc gaggctccag gcctccagag atccgtgagg aggaggtaca gacggtggag | 1680 |
| gatggggtgt ttgacatcca cttgtaa | 1707 |

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
ccucgucugu guuccggaa                                              19

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
uuccggaaca cagacgagg                                              19

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
gatggtggag ggatggctgc                                             20

<210> SEQ ID NO 49
<211> LENGTH: 1714
<212> TYPE: DNA
<213> ORGANISM: Homo sapiens

<400> SEQUENCE: 49

| | |
|---|---|
| atggcaggca ccctggacct ggacaagggc tgcacggtgg aggagctgct ccgcgggtgc | 60 |
| atcgaagcct tcgatgactc cgggaaggtg cgggacccgc agctggtgcg catgttcctc | 120 |
| atgatgcacc cctggtacat cccctcctct cagctggcgg ccaagctgct ccacatctac | 180 |
| caacaatccc ggaaggacaa ctccaattcc ctgcaggtga aaacgtgcca cctggtcagg | 240 |
| tactggatct ccgccttccc agcggagttt gacttgaacc cggagttggc tgagcagatc | 300 |
| aaggagctga aggctctgct agaccaagaa gggaaccgac ggcacagcag cctaatcgac | 360 |
| atagacagcg tccctaccta caagtggaag cggcaggtga ctcagcggaa ccctgtggga | 420 |
| cagaaaaagc gcaagatgtc cctgttgttt gaccaccctg agcccatgga gctggcggag | 480 |

```
catctcacct acttggagta tcgctccttc tgcaagatcc tgtttcagga ctatcacagt    540
ttcgtgactc atggctgcac tgtggacaac cccgtcctgg agcggttcat ctccctcttc    600
aacagcgtct cacagtgggt gcagctcatg atcctcagca aacccacagc ccgcagcgg    660 gccctggtca tcacacactt tgtccacgtg cggagaagc tgctacagct gcagaacttc    720
aacacgctga tggcagtggt cgggggcctg agccacagct ccatctcccg cctcaaggag    780
acccacagcc acgttagccc tgagaccatc aagctctggg agggtctcac ggaactagtg    840
acggcgacag gcaactatgg caactaccgg cgtcggctgg cagcctgtgt gggcttccgc    900
ttcccgatcc tgggtgtgca cctcaaggac ctggtggccc tgcagctggc actgcctgac    960
tggctggacc cagcccggac ccggctcaac ggggccaaga tgaagcagct ctttagcatc   1020
ctggaggagc tggccatggt gaccagcctg cggccaccag tacaggccaa ccccgacctg   1080
ctgagcctgc tcacggtgtc tctggatcag tatcagacgg aggatgagct gtaccagctg   1140
tccctgcagc gggagccgcg ctccaagtcc tcgccaacca gccccacgag ttgcacccca   1200
ccaccccggc ccccggtact ggaggagtgg acctcggctg ccaaacccaa gctggatcag   1260
gccctcgtgg tggagcacat cgagaagatg gtggagggat ggctgcatca gcagggagga   1320
gatggtttcc tatttcctgc gctccagctc tgtgttgggg gggcgcatgg gcttcgtaca   1380
caacttccag gagagcaact ccttgcgccc gtcgcctgc cgccactgca aagccctgat   1440
cctgggcatc tacaagcagg gcctcaaatg ccgagcctgt ggagtgaact gccacaagca   1500
gtgcaaggat cgcctgtcag ttgagtgtcg gcgcagggcc cagagtgtga gcctggaggg   1560
gtctgcaccc tcaccctcac ccatgcacag ccaccatcac cgcgccttca gcttctctct   1620
gccccgccct ggcaggcgag gctccaggcc tccagagatc cgtgaggagg aggtacagac   1680
ggtggaggat ggggtgtttg acatccactt gtaa                                1714

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
gguggaggga uggcugcau                                                   19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
augcagccau cccuccacc                                                   19

<210> SEQ ID NO 52
<211> LENGTH: 3099
<212> TYPE: DNA
<213> ORGANISM: Homo sapiens

<400> SEQUENCE: 52
atggcttggg aagcgaggcg cgaacccggc ccccgaaggg ccgccgtccg ggagacggtg     60
atgctgttgc tgtgcctggg ggtcccgacc ggccgcccct acaacgtgga cactgagagc    120
```

```
gcgctgctttt accagggccc ccacaacacg ctgttcggct actcggtcgt gctgcacagc    180
cacggggcga accgatggct cctagtgggt gcgcccactg ccaactggct cgccaacgct    240
tcagtgatca atcccggggc gatttacaga tgcaggatcg gaaagaatcc cggccagacg    300
tgcgaacagc tccagctggg tagccctaat ggagaacctt gtggaaagac ttgtttggaa    360
gagagagaca atcagtggtt gggggtcaca ctttccagac agccaggaga aaatggatcc    420
atcgtgactt gtgggcatag atggaaaaat atattttaca taagaatga aaataagctc    480 cccactggtg gttgctatgg agtgcccccct gatttacgaa cagaactgag taaaagaata    540
gctccgtgtt atcaagatta tgtgaaaaaa tttggagaaa attttgcatc atgtcaagct    600
ggaatatcca gttttacac aaaggattta attgtgatgg ggccccagg atcatcttac    660 tggactggct ctctttttgt ctacaatata actacaaata aatacaaggc ttttttagac    720
aaacaaaatc aagtaaaatt tggaagttat ttaggatatt cagtcggagc tggtcatttt    780
cggagccagc atactaccga agtagtcgga ggagctcctc aacatgagca gattggtaag    840
gcatatatat tcagcattga tgaaaaagaa ctaaatatct tacatgaaat gaaggtaaa    900 aagcttggat cgtactttgg agcttctgtc tgtgctgtgg acctcaatgc agatggcttc    960
tcagatctgc tcgtgggagc acccatgcag agcaccatca gagaggaagg aagagtgttt   1020
gtgtacatca actctggctc gggagcagta atgaatgcaa tggaaacaaa cctcgttgga   1080
agtgacaaat atgctgcaag atttggggaa tctatagtta atcttggcga cattgacaat   1140
gatggctttg aagatgttgc tatcggagct ccacaagaag atgacttgca aggtgctatt   1200
tatatttaca atggccgtgc agatgggatc tcgtcaacct tctcacagag aattgaagga   1260
cttcagatca gcaaatcgtt aagtatgttt ggacagtcta tatcaggaca aattgatgca   1320
gataataatg ctatgtaga gtagcagttt ggtgcttttc ggtctgattc tgctgtcttg   1380
ctaaggacaa gacctgtagt aattgttgac gcttctttaa gccaccctga gtcagtaaat   1440
agaacgaaat ttgactgtgt tgaaaatgga tggccttctg tgtgcataga tctaacactt   1500
tgtttctcat ataagggcaa ggaagttcca ggttacattg ttttgtttta acatgagt   1560 ttggatgtga acagaaaggc agagtctcca ccaagattct atttctcttc taatggaact   1620
tctgacgtga ttacaggaag catacaggtg tccagcagag aagctaactg tagaacacat   1680
caagcattta tgcggaaaga tgtgcgggac atcctcaccc caattcagat tgaagctgct   1740
taccaccttg gtcctcatgt catcagtaaa cgaagtacag aggaattccc accacttcag   1800
ccaattcttc agcagaagaa agaaaaagac ataatgaaaa aaacaataaa ctttgcaagg   1860
ttttgtgccc atgaaaattg ttctgctgat ttacaggttt ctgcaaagat tgggtttttg   1920
aagccccatg aaaataaaac atatcttgct gttgggagta tgaagacatt gatgttgaat   1980
gtgtccttgt ttaatgctgg agatgatgca tatgaaacga ctctacatgt caaactaccc   2040
gtgggtcttt atttcattaa gatttttagag ctggaagaga agcaaataaa ctgtgaagtc   2100
acagataact ctggcgtggt acaacttgac tgcagtattg ctatatata tgtagatcat   2160 ctctcaagga tagatattag cttttctcctg gatgtgagct cactcagcag agcggaagag   2220
gacctcagta tcacagtgca tgctacctgt gaaaatgaag aggaaatgga caatctaaag   2280
cacagcagag tgactgtagc aataccttta aaatatgagg ttaagctgac tgttcatggg   2340
tttgtaaacc caacttcatt tgtgtatgga tcaaatgatg aaaatgagcc tgaaacgtgc   2400
atggtggaga aaatgaactt aactttccat gttatcaaca ctggcaatag tatggctccc   2460
aatgttagtg tggaaataat ggtaccaaat tctttagcc cccaaactga taagctgttc   2520
```

```
aacattttgg atgtccagac tactactgga gaatgccact ttgaaaatta tcaaagagtg    2580
tgtgcattag agcagcaaaa gagtgcaatg cagaccttga aaggcatagt ccggttcttg    2640
tccaagactg ataagaggct attgtactgc ataaaagctg atccacattg tttaaatttc    2700
ttgtgtaatt ttgggaaaat ggaaagtgga aagaagcca gtgttcatat ccaactggaa     2760
ggccggccat ccattttaga aatggatgag acttcagcac tcaagtttga aataagagca    2820
acaggttttc cagagccaaa tccaagagta attgaactaa acaaggatga gaatgttgcg    2880
catgttctac tggaaggact acatcatcaa agacccaaac gttatttcac catagtgatt    2940
atttcaagta gcttgctact tggacttatt gtacttctat tgatctcata tgttatgtgg    3000
aaggctggct tctttaaaag acaatacaaa tctatcctac aagaagaaaa cagaagagac    3060
agttggagtt atatcaacag taaaagcaat gatgattaa                          3099
```

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
tcttgctgtt gggagtatga a                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
tgatactgag gtcctcttcc g                                              21

<210> SEQ ID NO 55
<211> LENGTH: 19
<212> TYPE: RNA
<213> ORGANISM: Artificial Sequence
<220> FEATURE:
<223> OTHER INFORMATION: Synthetic

<400> SEQUENCE: 55
gggaguauga agacauuga                                                 19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
ucaaugucuu cauacuccc                                                 19

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57 gggttttga agaagagaag c                                                 21

<210> SEQ ID NO 58
<211> LENGTH: 2948
<212> TYPE: DNA
<213> ORGANISM: Homo sapiens

<400> SEQUENCE: 58

| | | | | | |
|---|---|---|---|---|---|
| atggcttggg | aagcgaggcg | cgaacccggc | ccccgaaggg | ccgccgtccg | ggagacggtg | 60 |
| atgctgttgc | tgtgcctggg | ggtcccgacc | ggccgcccct | acaacgtgga | cactgagagc | 120 |
| gcgctgcttt | accagggccc | ccacaacacg | ctgttcggct | actcggtcgt | gctgcacagc | 180 |
| cacggggcga | accgatggct | cctagtgggt | gcgcccactg | ccaactggct | cgccaacgct | 240 |
| tcagtgatca | atcccggggc | gatttacaga | tgcaggatcg | gaaagaatcc | cggccagacg | 300 |
| tgcgaacagc | tccagctggg | tagccctaat | ggagaacctt | gtggaaagac | ttgtttggaa | 360 |
| gagagagaca | atcagtggtt | gggggtcaca | ctttccagac | agccaggaga | aaatggatcc | 420 |
| atcgtgactt | gtgggcatag | atggaaaaat | atatttttaca | taaagaatga | aaataagctc | 480 |
| cccactggtg | gttgctatgg | agtgccccct | gatttacgaa | cagaactgag | taaaagaata | 540 |
| gctccgtgtt | atcaagatta | tgtgaaaaaa | tttggagaaa | attttgcatc | atgtcaagct | 600 |
| ggaatatcca | gttttttacac | aaaggattta | attgtgatgg | gggccccagg | atcatcttac | 660 |
| tggactggct | ctcttttttgt | ctacaatata | actacaaata | aatacaaggc | ttttttagac | 720 |
| aaacaaaatc | aagtaaaatt | tggaagttat | ttaggatatt | cagtcggagc | tggtcatttt | 780 |
| cggagccagc | atactaccga | agtagtcgga | ggagctcctc | aacatgagca | gattggtaag | 840 |
| gcatatatat | tcagcattga | tgaaaaagaa | ctaaatatct | tacatgaaat | gaaaggtaaa | 900 |
| aagcttggat | cgtactttgg | agcttctgtc | tgtgctgtgg | acctcaatgc | agatggcttc | 960 |
| tcagatctgc | tcgtgggagc | acccatgcag | agcaccatca | gagaggaagg | aagagtgttt | 1020 |
| gtgtacatca | actctggctc | gggagcagta | atgaatgcaa | tggaaacaaa | cctcgttgga | 1080 |
| agtgacaaat | atgctgcaag | atttggggaa | tctatagtta | atcttggcga | cattgacaat | 1140 |
| gatggctttg | aagatgttgc | tatcggagct | ccacaagaag | atgacttgca | aggtgctatt | 1200 |
| tatatttaca | atggccgtgc | agatgggatc | tcgtcaacct | tctcacagag | aattgaagga | 1260 |
| cttcagatca | gcaaatcgtt | aagtatgttt | ggacagtcta | tatcaggaca | aattgatgca | 1320 |
| gataataatg | ctatgtaga | tgtagcagtt | ggtgcttttc | ggtctgattc | tgctgtcttg | 1380 |
| ctaaggacaa | gacctgtagt | aattgttgac | gcttctttaa | gccaccctga | gtcagtaaat | 1440 |
| agaacgaaat | ttgactgtgt | tgaaaatgga | tggccttctg | tgtgcataga | tctaacactt | 1500 |
| tgtttctcat | ataagggcaa | ggaagttcca | ggttacattg | ttttgttta | taacatgagt | 1560 |
| ttggatgtga | acagaaaggc | agagtctcca | ccaagattct | atttctcttc | taatggaact | 1620 |
| tctgacgtga | ttacaggaag | catacaggtg | tccagcagag | aagctaactg | tagaacacat | 1680 |
| caagcattta | tgcggaaaga | tgtgcgggac | atcctcaccc | caattcagat | tgaagctgct | 1740 |
| taccaccttg | gtcctcatgt | catcagtaaa | cgaagtacag | aggaattccc | accacttcag | 1800 |
| ccaattcttc | agcagaagaa | agaaaaagac | ataatgaaaa | aaacaataaa | ctttgcaagg | 1860 |
| ttttgtgccc | atgaaaattg | ttctgctgat | ttacaggttt | ctgcaaagat | tgggtttttg | 1920 |
| aagaagagaa | gcaaataaac | tgtgaagtca | cagataactc | tggcgtggta | caacttgact | 1980 |
| gcagtattgg | ctatatatat | gtagatcatc | tctcaaggat | agatattagc | tttctcctgg | 2040 |
| atgtgagctc | actcagcaga | gcggaagagg | acctcagtat | cacagtgcat | gctacctgtg | 2100 |

```
aaaatgaaga ggaaatggac aatctaaagc acagcagagt gactgtagca ataccttaa    2160 aatatgaggt taagctgact gttcatgggt ttgtaaaccc aacttcattt gtgtatggat   2220
caaatgatga aaatgagcct gaaacgtgca tggtggagaa aatgaactta actttccatg   2280
ttatcaacac tggcaatagt atggctccca atgttagtgt ggaaataatg gtaccaaatt   2340
cttttagccc ccaaactgat aagctgttca acattttgga tgtccagact actactggag   2400
aatgccactt tgaaaattat caagagtgt gtgcattaga gcagcaaaag agtgcaatgc    2460
agaccttgaa aggcatagtc cggttcttgt ccaagactga taagaggcta ttgtactgca   2520
taaaagctga tccacattgt ttaaatttct tgtgtaattt tgggaaaatg gaaagtggaa   2580
aagaagccag tgttcatatc caactggaag gccggccatc cattttagaa atggatgaga   2640
cttcagcact caagtttgaa ataagagcaa caggttttcc agagccaaat ccaagagtaa   2700
ttgaactaaa caaggatgag aatgttgcgc atgttctact ggaaggacta catcatcaaa   2760
gacccaaacg ttatttcacc atagtgatta tttcaagtag cttgctactt ggacttattg   2820
tacttctatt gatctcatat gttatgtgga aggctggctt cttaaaaga caatacaaat    2880 ctatcctaca agaagaaaac agaagagaca gttggagtta tatcaacagt aaaagcaatg   2940
atgattaa                                                            2948

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
gaagaagaga agcaaauaa                                                  19

<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
uuauuugcuu cucuucuuc                                                  19

<210> SEQ ID NO 61
<211> LENGTH: 19
<212> TYPE: DNA
<213> ORGANISM: Artificial Sequence
<220> FEATURE:
<223> OTHER INFORMATION: Synthetic

<400> SEQUENCE: 61
ctggaaatta agggaaatg                                                  19

<210> SEQ ID NO 62
<211> LENGTH: 4226
<212> TYPE: DNA
<213> ORGANISM: Homo sapiens

<400> SEQUENCE: 62
atgaaggccc ccgctgtgct tgcacctggc atcctcgtgc tcctgtttac cttggtgcag   60
aggagcaatg ggagtgtaaa gaggcactag caaagtccga gatgaatgtg aatatgaagt   120
```

```
atcagcttcc caacttcacc gcggaaacac ccatccagaa tgtcattcta catgagcatc    180
acattttcct tggtgccact aactacattt atgttttaaa tgaggaagac cttcagaagg    240
ttgctgagta caagactggg cctgtgctgg aacacccaga ttgtttccca tgtcaggact    300
gcagcagcaa agccaattta tcaggaggtg tttggaaaga taacatcaac atggctctag    360
ttgtcgacac ctactatgat gatcaactca ttagctgtgg cagcgtcaac agagggacct    420
gccagcgaca tgtctttccc cacaatcata ctgctgacat acagtcggag gttcactgca    480
tattctcccc acagatagaa gagcccagcc agtgtcctga ctgtgtggtg agcgccctgg    540
gagccaaagt cctttcatct gtaaaggacc ggttcatcaa cttctttgta ggcaatacca    600
taaattcttc ttatttccca gatcatccat tgcattcgat atcagtgaga aggctaaagg    660
aaacgaaaga tggttttatg tttttgacgg accagtccta cattgatgtt ttacctgagt    720
tcagagattc ttaccccatt aagtatgtcc atgcctttga agcaacaat tttatttact     780 tcttgacggt ccaaagggaa actctagatg ctcagacttt tcacacaaga ataatcaggt    840
tctgttccat aaactctgga ttgcattcct acatggaaat gcctctggag tgtattctca    900
cagaaaagag aaaaaagaga tccacaaaga aggaagtgtt taatatactt caggctgcgt    960
atgtcagcaa gcctggggcc cagcttgcta gacaaatagg agccagcctg aatgatgaca   1020
ttcttttcgg ggtgttcgca caaagcaagc cagattctgc cgaaccaatg gatcgatctg   1080
ccatgtgtgc attccctatc aaatatgtca acgacttctt caacaagatc gtcaacaaaa   1140
acaatgtgag atgtctccag cattttacg acccaatca tgagcactgc tttaatagga    1200
cacttctgag aaaattcatca ggctgtgaag cgcgccgtga tgaatatcga acagagttta   1260
ccacagcttt gcagcgcgtt gacttattca tgggtcaatt cagcgaagtc ctcttaacat   1320
ctatatccac cttcattaaa ggagacctca ccatagctaa tcttgggaca tcagagggtc   1380
gcttcatgca ggttgtggtt tctcgatcag gaccatcaac ccctcatgtg aatttttctcc  1440 tggactccca tccagtgtct ccagaagtga ttgtggagca tacattaaac caaaatggct   1500
acacactggt tatcactggg aagaagatca cgaagatccc attgaatggc ttgggctgca   1560
gacatttcca gtcctgcagt caatgcctct ctgccccacc cttttgttcag tgtggctggt  1620 gccacgacaa atgtgtgcga tcggaggaat gcctgagcgg acatggact caacagatct    1680 gtctgcctgc aatctacaag gttttcccaa atagtgcacc ccttgaagga gggacaaggc   1740
tgaccatatg tggctgggac tttggatttc ggaggaataa taaatttgat ttaaagaaaa   1800
ctagagttct ccttggaaat gagagctgca ccttgacttt aagtgagagc acgatgaata   1860
cattgaaatg cacagttggt cctgccatga ataagcattt caatatgtcc ataattattt   1920
caaatggcca cggacaaca caatacagta cattctccta tgtggatcct gtaataacaa    1980
gtatttcgcc gaaatacggt cctatggctg gtggcacttt acttactta actgaaaatt    2040 acctaaacag tgggaattct agacacattt caattggtgg aaaaacatgt actttaaaaa    2100
gtgtgtcaaa cagtattctt gaatgttata ccccagccca aaccatttca actgagtttg   2160
ctgttaaatt gaaaattgac ttagccaacc gagagacaag catcttcagt taccgtgaag   2220
atcccattgt ctatgaaatt catccaacca atctttttat tagtacttgg tggaaagaac    2280
ctctcaacat tgtcagtttt ctattttgct ttgccagtgg tgggagcaca ataacaggtg    2340
ttgggaaaaa cctgaattca gttagtgtcc cgagaatggt cataaatgtg catgaagcag    2400
gaaggaactt tacagtggca tgtcaacatc gctctaattc agagataatc tgttgtacca    2460
ctccttccct gcaacagctg aatctgcaac tccccctgaa aaccaaagcc ttttcatgt     2520
```

| | |
|---|---|
| tagatgggat cctttccaaa tactttgatc tcatttatgt acataatcct gtgtttaagc | 2580 |
| cttttgaaaa gccagtgatg atctcaatgg gcaatgaaaa tgtactggaa attaagggaa | 2640 |
| atgatattga ccctgaagca gttaaaggtg aagtgttaaa agttggaaat aagagctgtg | 2700 |
| agaatataca cttacattct gaagccgttt tatgcacggt ccccaatgac ctgctgaaat | 2760 |
| tgaacagcga gctaaatata gagtggaagc aagcaatttc ttcaaccgtc cttggaaaag | 2820 |
| taatagttca accagatcag aatttcacag gattgattgc tggtgttgtc tcaatatcaa | 2880 |
| cagcactgtt attactactt gggttttttcc tgtggctgaa aaagagaaag caaattaaag | 2940 |
| atctgggcag tgaattagtt cgctacgatg caagagtaca cactcctcat ttggataggc | 3000 |
| ttgtaagtgc ccgaagtgta agcccaacta cagaaatggt ttcaaatgaa tctgtagact | 3060 |
| accgagctac ttttccagaa gatcagtttc ctaattcatc tcagaacggt tcatgccgac | 3120 |
| aagtgcagta tcctctgaca gacatgtccc ccatcctaac tagtggggac tctgatatat | 3180 |
| ccagtccatt actgcaaaat actgtccaca ttgacctcag tgctctaaat ccagagctgg | 3240 |
| tccaggcagt gcagcatgta gtgattgggc ccagtagcct gattgtgcat ttcaatgaag | 3300 |
| tcataggaag agggcatttt ggttgtgtat atcatgggac tttgttggac aatgatggca | 3360 |
| agaaaattca ctgtgctgtg aaatccttga acagaatcac tgacatagga gaagtttccc | 3420 |
| aatttctgac cgagggaatc atcatgaaag atttttagtca tcccaatgtc ctctcgctcc | 3480 |
| tgggaatctg cctgcgaagt gaagggtctc cgctggtggt cctaccatac atgaaacatg | 3540 |
| gagatcttcg aaatttcatt cgaaatgaga ctcataatcc aactgtaaaa gatcttattg | 3600 |
| gctttggtct tcaagtagcc aaaggcatga atatcttgc aagcaaaaag tttgtccaca | 3660 |
| gagacttggc tgcaagaaac tgtatgctgg atgaaaaatt cacagtcaag gttgctgatt | 3720 |
| ttggtcttgc cagagacatg tatgataaag aatactatag tgtacacaac aaaacaggtg | 3780 |
| caaagctgcc agtgaagtgg atggctttgg aaagtctgca aactcaaaag tttaccacca | 3840 |
| agtcagatgt gtggtccttt ggcgtgctcc tctgggagct gatgacaaga ggagccccac | 3900 |
| cttatcctga cgtaaacacc tttgatataa ctgtttactt gttgcaaggg agaagactcc | 3960 |
| tacaacccga atactgccca gaccccttat atgaagtaat gctaaaatgc tggcacccta | 4020 |
| aagccgaaat gcgcccatcc ttttctgaac tggtgtcccg gatatcagcg atcttctcta | 4080 |
| cttttcattgg ggagcactat gtccatgtga acgctactta tgtgaacgta aaatgtgtcg | 4140 |
| ctccgtatcc ttctctgttg tcatcagaag ataacgctga tgatgaggtg gacacacgac | 4200 |
| cagcctcctt ctgggagaca tcatag | 4226 |

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
guacuggaaa uuaagggaa        19

<210> SEQ ID NO 64
<211> LENGTH: 19
<212> TYPE: RNA
<213> ORGANISM: Artificial Sequence
<220> FEATURE:
<223> OTHER INFORMATION: Synthetic

```
<400> SEQUENCE: 64
uucccuuaau uuccaguac                                                    19

<210> SEQ ID NO 65
<211> LENGTH: 4651
<212> TYPE: DNA
<213> ORGANISM: Homo sapiens

<400> SEQUENCE: 65
atgaaggccc ccgctgtgct tgcacctggc atcctcgtgc tcctgtttac cttggtgcag      60
aggagcaatg ggagtgtaaa gaggcactag caaagtccga gatgaatgtg aatatgaagt     120
atcagcttcc caacttcacc gcggaaacac ccatccagaa tgtcattcta catgagcatc     180
acattttcct tggtgccact aactacattt atgttttaaa tgaggaagac cttcagaagg     240
ttgctgagta caagactggg cctgtgctgg aacacccaga ttgtttccca tgtcaggact     300
gcagcagcaa agccaattta tcaggaggtg tttggaaaga taacatcaac atggctctag     360
ttgtcgacac tactatgat gatcaactca ttagctgtgg cagcgtcaac agagggacct      420
gccagcgaca tgtctttccc cacaatcata ctgctgacat acagtcggag gttcactgca     480
tattctcccc acagatagaa gagcccagcc agtgtcctga ctgtgtggtg agcgccctgg     540
gagccaaagt cctttcatct gtaaaggacc ggttcatcaa cttctttgta ggcaatacca     600
taaattcttc ttatttccca gatcatccat tgcattcgat atcagtgaga aggctaaagg     660
aaacgaaaga tggttttatg tttttgacgg accagtccta cattgatgtt ttacctgagt     720
tcagagattc ttaccccatt aagtatgtcc atgcctttga aagcaacaat tttatttact     780
tcttgacggt ccaaagggaa actctagatg ctcagacttt tcacacaaga ataatcaggt     840
tctgttccat aaactctgga ttgcattcct acatggaaat gcctctggag tgtattctca     900
cagaaaagag aaaaaagaga tccacaaaga aggaagtgtt taatatactt caggctgcgt     960
atgtcagcaa gcctggggcc cagcttgcta gacaaatagg agccagcctg aatgatgaca    1020
ttcttttcgg ggtgttcgca caaagcaagc cagattctgc cgaaccaatg gatcgatctg    1080
ccatgtgtgc attccctatc aaatatgtca acgacttctt caacaagatc gtcaacaaaa    1140
acaatgtgag atgtctccag cattttacg gacccaatca tgagcactgc tttaatagga    1200
cacttctgag aaattcatca ggctgtgaag cgcgccgtga tgaatatcga acagagttta    1260
ccacagcttt gcagcgcgtt gacttattca tgggtcaatt cagcgaagtc ctcttaacat    1320
ctatatccac cttcattaaa ggagacctca ccatagctaa tcttgggaca tcagagggtc    1380
gcttcatgca ggttgtggtt tctcgatcag gaccatcaac ccctcatgtg aattttctcc    1440
tggactccca tccagtgtct ccagaagtga ttgtggagca tacattaaac caaaatggct    1500
acacactggt tatcactggg aagaagatca cgaagatccc attgaatggc ttgggctgca    1560
gacatttcca gtcctgcagt caatgcctct ctgccccacc ctttgttcag tgtggctggt    1620
gccacgacaa atgtgtgcga tcggaggaat gcctgagcgg acatggact caacagatct     1680 gtctgcctgc aatctacaag gttttcccaa atagtgcacc ccttgaagga gggacaaggc    1740
tgaccatatg tggctgggac tttgatttc ggaggaataa taaatttgat ttaaagaaaa      1800
ctagagttct ccttggaaat gagagctgca ccttgactt aagtgagagc acgatgaata     1860
cattgaaatg cacagttggt cctgccatga taagcatt caatatgtcc ataattattt      1920
caaatggcca cggacaaca caatacagta cattctccta tgtggatcct gtaataacaa      1980
gtatttcgcc gaaatacggt cctatggctg gtggcacttt acttactta actggaaatt     2040
```

```
acctaaacag tgggaattct agacacattt caattggtgg aaaaacatgt actttaaaaa    2100
gtgtgtcaaa cagtattctt gaatgttata ccccagccca aaccatttca actgagtttg    2160
ctgttaaatt gaaaattgac ttagccaacc gagagacaag catcttcagt taccgtgaag    2220
atcccattgt ctatgaaatt catccaacca aatcttttat tagtacttgg tggaaagaac    2280
ctctcaacat tgtcagtttt ctattttgct ttgccagtgg tgggagcaca ataacaggtg    2340
ttgggaaaaa cctgaattca gttagtgtcc cgagaatggt cataaatgtg catgaagcag    2400
gaaggaactt tacagtggca tgtcaacatc gctctaattc agagataatc tgttgtacca    2460
ctccttccct gcaacagctg aatctgcaac tcccccctgaa aaccaaagcc tttttcatgt    2520
tagatgggat cctttccaaa tactttgatc tcatttatgt acataatcct gtgtttaagc    2580
cttttgaaaa gccagtgatg atctcaatgg gcaatgaaaa tgtactggaa attaaggtgg    2640
gagcagtggc aattcaggga gattatttta gtatcatggt tcaatatttt ttcatacttc    2700 attttttctta tgtatgagag gaaagcaaag gcataagaga atatttgttg tgtcagcaat    2760
ctaactcttt atcaatacgt taagttgatc acattaaaac ttctacctct cagccaggca    2820
cggtagctca tacctgtaat cccagcactt tgggaggcca aggcgggtga atcacttgag    2880
atcaggagtt caagaccagc ctggccaaaa tggtgaaacc ccatctccac taaaaataca    2940
aaaattagct gggcatggtg gtgggtgcct gtaatcccag ctactcagga ggctgaggga    3000
cggaggtgac ctgagtcctg aaggcggagg ttgcagtgag ccaagatggc accactgcac    3060
tggaaatgat attgaccctg aagcagttaa aggtgaagtg ttaaaagttg gaaataagag    3120
ctgtgagaat atacacttac attctgaagc cgttttatgc acggtcccca atgacctgct    3180
gaaattgaac agcagagctaa atatagagtg gaagcaagca atttcttcaa ccgtccttgg    3240
aaaagtaata gttcaaccag atcagaattt cacaggatta attgctggtg ttgtctcaat    3300
atcaacagca ctgttattac tacttgggtt tttcctgtgg ctgaaaaaga gaaagcaaat    3360
taaagatctg ggcagtgaat tagttcgcta cgatgcaaga gtacacactc ctcatttgga    3420
taggcttgta agtgcccgaa gtgtaagccc aactacagaa atggtttcaa atgaatctgt    3480
agactaccga gctactttc cagaagatca gtttcctaat tcatctcaga acggttcatg    3540
ccgacaagtg cagtatcctc tgacagacat gtcccccatc ctaactagtg gggactctga    3600
tatatccagt ccattactgc aaaatactgt ccacattgac ctcagtgctc taaatccaga    3660
gctggtccag gcagtgcagc atgtagtgat tgggcccagt agcctgattg tgcatttcaa    3720
tgaagtcata ggaagagggc attttggttg tgtatatcat gggactttgt tggacaatga    3780
tggcaagaaa attcactgtg ctgtgaaatc cttgaacaga atcactgaca taggagaagt    3840
ttcccaattt ctgaccgagg gaatcatcat gaaagatttt agtcatccca atgtcctctc    3900
gctcctggga atctgcctgc gaagtgaagg gtctccgctg gtggtcctac catacatgaa    3960
acatggagat cttcgaaatt tcattcgaaa tgagactcat aatccaactg taaaagatct    4020 tattggctt ggtcttcaag tagccaaagg catgaaatat cttgcaagca aaagtttgt    4080 ccacagagac ttggctgcaa gaaactgtat gctggatgaa aaattcacag tcaaggttgc    4140
tgattttggt cttgccagag acatgtatga taaagaatac tatagtgtac acaacaaaac    4200
aggtgcaaag ctgccagtga agtggatggc tttggaaagt ctgcaaactc aaaagtttac    4260
caccaagtca gatgtgtggt cctttggcgt gctcctctgg gagctgatga caagaggagc    4320
cccaccttat cctgacgtaa acacctttga tataactgtt tacttgttgc aagggagaag    4380
```

```
actcctacaa cccgaatact gcccagaccc cttatatgaa gtaatgctaa aatgctggca    4440
ccctaaagcc gaaatgcgcc catccttttc tgaactggtg tcccggatat cagcgatctt    4500
ctctactttc attggggagc actatgtcca tgtgaacgct acttatgtga acgtaaaatg    4560
tgtcgctccg tatccttctc tgttgtcatc agaagataac gctgatgatg aggtggacac    4620
acgaccagcc tccttctggg agacatcata g                                   4651
```

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66

```
tggtggaaag aacctctcaa                                                  20
```

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67

```
atcttggctc actgcaacct                                                  20
```

<210> SEQ ID NO 68
<211> LENGTH: 19
<212> TYPE: RNA
<213> ORGANISM: Artificial Sequence
<220> FEATURE:
<223> OTHER INFORMATION: Synthetic

<400> SEQUENCE: 68

```
cagcaaucua acucuuuau                                                   19
```

<210> SEQ ID NO 69
<211> LENGTH: 19
<212> TYPE: RNA
<213> ORGANISM: Artificial Sequence
<220> FEATURE:
<223> OTHER INFORMATION: Synthetic

<400> SEQUENCE: 69

```
auaaagaguu agauugcug                                                   19
```

<210> SEQ ID NO 70
<211> LENGTH: 8520
<212> TYPE: DNA
<213> ORGANISM: Homo sapiens

<400> SEQUENCE: 70

```
atggccgcgc acaggccggt ggaatgggtc caggccgtgg tcagccgctt cgacgagcag      60
cttccaataa aaacaggaca gcagaacaca cataccaaag tcagtactga gcacaacaag     120
gaatgtctaa tcaatatttc caaatacaag ttttctttgg ttataagcgg cctcactact     180
attttaaaga atgttaacaa tatgagaata tttggagaag ctgctgaaaa aaatttatat     240
ctctctcagt tgattatatt ggatacactg gaaaaatgtc ttgctgggca accaaaggac     300
acaatgagat tagatgaaac gatgctggtc aaacagttgc tgccagaaat ctgccatttt     360
cttcacacct gtcgtgaagg aaaccagcat gcagctgaac ttcggaattc tgcctctggg     420
```

```
gttttatttt ctctcagctg caacaacttc aatgcagtct ttagtcgcat ttctaccagg        480
ttacaggaat taactgtttg ttcagaagac aatgttgatg ttcatgatat agaattgtta        540
cagtatatca atgtggattg tgcaaaatta aaacgactcc tgaaggaaac agcatttaaa        600
tttaaagccc taaagaaggt tgcgcagtta gcagttataa atagcctgga aaaggcattt        660
tggaactggg tagaaaatta tccagatgaa tttacaaaac tgtaccagat cccacagact        720
gatatggctg aatgtgcaga aaagctattt gacttggtgg atggttttgc tgaaagcacc        780
aaacgtaaag cagcagtttg gccactacaa atcattctcc ttatcttgtg tccagaaata        840
atccaggata tatccaaaga cgtggttgat gaaaacaaca tgaataagaa gttatttctg        900
gacagtctac gaaaagctct tgctggccat ggaggaagta ggcagctgac agaaagtgct        960
gcaattgcct gtgtcaaact gtgtaaagca agtacttaca tcaattggga agataactct       1020
gtcattttcc tacttgttca gtccatggtg gttgatctta agaacctgct ttttaatcca       1080
agtaagccat tctcaagagg cagtcagcct gcagatgtgg atctaatgat tgactgcctt       1140
gtttcttgct ttcgtataag ccctcacaac aaccaacact ttaagatctg cctggctcag       1200
aattcacctt ctacatttca ctatgtgctg gtaaattcac tccatcgaat catcaccaat       1260
tccgcattgg attggtggcc taagattgat gctgtgtatt gtcactcggt tgaacttcga       1320
aatatgtttg gtgaaacact tcataaagca gtgcaaggtt gtggagcaca cccagcaata       1380
cgaatggcac cgagtcttac atttaaagaa aaagtaacaa gccttaaatt taaagaaaaa       1440
cctacagacc tggagacaag aagctataag tatcttctct tgtccatggt gaaactaatt       1500
catgcagatc caaagctctt gctttgtaat ccaagaaaac agggggcccga aacccaaggc       1560 agtacagcag aattaattac agggctcgtc caactggtcc ctcagtcaca catgccagag       1620
attgctcagg aagcaatgga ggctctgctg gttcttcatc agttagatag cattgatttg       1680
tggaatcctg atgctcctgt agaaacattt tgggagatta gctcacaaat gctttttttac       1740 atctgcaaga aattaactag tcatcaaatg cttagtagca cagaaattct caagtggttg       1800
cgggaaatat tgatctgcag gaataaattt cttcttaaaa ataagcaggc agatagaagt       1860
tcctgtcact ttctcctttt ttacgggta ggatgtgata ttccttctag tggaaatacc       1920
agtcaaatgt ccatggatca tgaagaatta ctacgtactc ctggagcctc tctccggaag       1980
ggaaaaggga actcctctat ggatagtgca gcaggatgca gcggaacccc ccgatttgc        2040 cgacaagccc agaccaaact agaagtggcc ctgtacatgt ttctgtggaa ccctgacact       2100
gaagctgttc tggttgccat gtcctgtttc cgccacctct gtgaggaagc agatatccgg       2160
tgtggggtgg atgaagtgtc agtgcataac ctcttgccca actataacac attcatggag       2220
tttgcctctg tcagcaatat gatgtcaaca ggaagagcag cacttcagaa aagagtgatg       2280
gcactgctga ggcgcattga gcatcccact gcaggaaaca ctgaggcttg gaagatacaa       2340
catgcaaaat gggaacaagc aacaaagcta atccttaact atccaaaagc caaaatggaa       2400
gatggccagg ctgctgaaag ccttcacaag accattgtta agaggcgaat gtcccatgtg       2460 agtgaggag atccatgaga tttgtctgac acagactccc tacaggaatg atcaacatg        2520 actggcttcc tttgtgccct tggggagtg tgcctccagc agagaagcaa ttctggcctg       2580
gcaacctata gcccacccat gggtccagtc agtgaacgta agggttctat gatttcagtg       2640
atgtcttcag agggaaacgc agatacacct gtcagcaaat ttatggatcg gctgttgtcc       2700
ttaatggtgt gtaaccatga gaaagtggga cttcaaatac ggaccaatgt taaggatctg       2760
```

```
gtgggtctag aattgagtcc tgctctgtat ccaatgctat ttaacaaatt gaagaatacc    2820
atcagcaagt tttttgactc ccaaggacag gttttattga ctgataccaa tactcaattt    2880
gtagaacaaa ccatagctat aatgaagaac ttgctagata tcatactga aggcagctct     2940 gaacatctag ggcaagctag cattgaaaca atgatgttaa atctggtcag gtatgttcgt    3000
gtgcttggga atatggtcca tgcaattcaa ataaaaacga aactgtgtca attagttgaa    3060
gtaatgatgg caaggagaga tgacctctca ttttgccaag agatgaaatt taggaataag    3120
atggtagaat acctgacaga ctgggttatg gaacatcaa accaagcagc agatgatgat     3180
gtaaaatgtc ttacaagaga tttggaccag gcaagcatgg aagcagtagt ttcacttcta    3240
gctggtctcc ctctgcagcc tgaagaagga gatggtgtgg aattgatgga agccaaatca    3300
cagttatttc ttaaatactt cacattattt atgaaccttt tgaatgactg cagtgaagtt    3360
gaagatgaaa gtgcgcaaac aggtggcagg aaacgtggca tgtctcggag gctggcatca    3420
ctgaggcact gtacggtcct tgcaatgtca aacttactca atgccaacgt agacagtggt    3480
ctcatgcact ccataggctt aggttaccac aaggatctcc agacaagagc tacatttatg    3540
gaagttctga caaaaatcct tcaacaaggc acagaatttg acacacttgc agaaacagta    3600
ttggctgatc ggtttgagag attggtggaa ctggtcacaa tgatgggtga tcaaggagaa    3660
ctccctatag cgatggctct ggccaatgtg gttccttgtt ctcagtggga tgaactagct    3720
cgagttctgg ttactctgtt tgattctcgg catttactct accaactgct ctggaacatg    3780
ttttctaaag aagtagaatt ggcagactcc atgcagactc tcttccgagg caacagcttg    3840
gccagtaaaa taatgacatt ctgtttcaag gtatatggtg ctacctatct acaaaaactc    3900
ctggatcctt tattacgaat tgtgatcaca tcctctgatt ggcaacatgt tagctttgaa    3960
gtggatccta ccaggttaga accatcagag agccttgagg aaaaccagcg gaacctcctt    4020
cagatgactg aaaagttctt ccatgccatc atcagttcct cctcagaatt cccccctcaa    4080
cttcgaagtg tgtgccactg tttataccag gcaacttgcc actccctact gaataaagct    4140
acagtaaaag aaaaaaagga aaacaaaaaa tcagtggtta gccagcgttt ccctcagaac    4200
agcatcggtg cagtaggaag tgccatgttc ctcagattta tcaatcctgc cattgtctca    4260
ccgtatgaag cagggatttt agataaaaag ccaccaccta gaatcgaaag gggcttgaag    4320
ttaatgtcaa agatacttca gagtattgcc aatcatgttc tcttcacaaa agaagaacat    4380
atgcggcctt tcaatgattt tgtgaaaagc aactttgatg cagcacgcag gttttttcctt    4440 gatatagcat ctgattgtcc tacaagtgat gcagtaaatc atagtctttc cttcataagt    4500
gacggcaatg tgcttgcttt acatcgtcta ctctggaaca tcaggagaa aattgggcag    4560 tatctttcca gcaacaggga tcataaagct gttggaagac gacctttga taagatggca    4620 acacttcttg catacctggg tcctccagag cacaaacctg tggcagatac acactggtcc    4680
agccttaacc ttaccagttc aaagtttgag gaatttatga ctaggcatca ggtacatgaa    4740
aaagaagaat tcaaggcttt gaaaacgtta agtattttct accaagctgg gacttccaaa    4800
gctgggaatc ctatttttta ttatgttgca cggaggttca aaactggtca atcaatggt     4860 gatttgctga tataccatgt cttactgact ttaaagccat attatgcaaa gccatatgaa    4920
attgtagtgg accttaccca taccgggcct agcaatcgct ttaaaacaga ctttctctct    4980
aagtggtttg ttgtttttcc tggctttgct tacgacaacg tctccgcagt ctatatctat    5040
aactgtaact cctgggtcag ggagtacacc aagtatcatg agcggctgct gactggcctc    5100
aaaggtagca aaaggcttgt tttcatagac tgtcctggga aactggctga gcacatagag    5160
```

```
catgaacaac agaaactacc tgctgccacc ttggctttag aagaggacct gaaggtattc    5220
cacaatgctc tcaagctagc tcacaaagac accaaagttt ctattaaagt tggttctact    5280
gctgtccaag taacttcagc agagcgaaca aaagtcctag ggcaatcagt ctttctaaat    5340
gacatttatt atgcttcgga aattgaagaa atctgcctag tagatgagaa ccagttcacc    5400
ttaaccattg caaaccaggg cacgccgctc accttcatgc accaggagtg tgaagccatt    5460
gtccagtcta tcattcatat ccggacccgc tgggaactgt cacagcccga ctctatcccc    5520
caacacacca agattcggcc aaaagatgtc cctgggacac tgctcaatat cgcattactt    5580
aatttaggca gttctgaccc gagtttacgg tcagctgcct ataatcttct gtgtgcctta    5640
acttgtacct ttaatttaaa atcgagggc cagttactag agacatcagg tttatgtatc    5700
cctgccaaca cacctctt tattgtctct attagtaaga cactggcagc caatgagcca    5760
cacctcacgt tagaattttt ggaagagtgt atttctggat ttagcaaatc tagtattgaa    5820
ttgaaacacc tttgtttgga atacatgact ccatggctgt caaatctagt tcgttttgc     5880 aagcataatg atgatgccaa acgacaaaga gttactgcta ttcttgacaa gctgataaca    5940
atgaccatca atgaaaaaca gatgtaccca tctattcaag caaaaatatg gggaagcctt    6000
gggcagatta cagatctgct tgatgttgta ctagacagtt tcatcaaaac cagtgcaaca    6060
ggtggcttgg gatcaataaa agctgaggtg atggcagata ctgctgtagc tttggcttct    6120
ggaaatgtga aattggtttc aagcaaggtt attggaagga tgtgcaaaat aattgacaag    6180
acatgcttat ctccaactcc tactttagaa caacatctta tgtgggatga tattgctatt    6240
ttagcacgct acatgctgat gctgtccttc aacaattccc ttgatgtggc agctcatctt    6300
ccctacctct tccacgttgt tacttttctta gtagccacag gtccgctctc ccttagagct    6360
tccacacatg gactggtcat taatatcatt cactctctgt gtacttgttc acagcttcat    6420
tttagtgaag agaccaagca agttttgaga ctcagtctga cagagttctc attacccaaa    6480
ttttacttgc tgtttggcat tagcaaagtc aagtcagctg ctgtcattgc cttccgttcc    6540
agttaccggg acaggtcatt ctctcctggc tcctatgaga gagagacttt tgctttgaca    6600
tccttggaaa cagtcacaga agctttgttg gagatcatgg aggcatgcat gagagatatt    6660
ccaacgtgca gtggctgga ccagtggaca gaactagctc aaagatttgc attccaatat    6720
aatccatccc tgcaaccaag agctcttgtt gtctttgggt gtattagcaa acgagtgtct    6780
catgggcaga taaagcagat aatccgtatt cttagcaagg cacttgagag ttgcttaaaa    6840
ggacctgaca cttacaacag tcaagttctg atagaagcta cagtaatagc actaaccaaa    6900
ttacagccac ttcttaataa ggactcgcct ctgcacaaag ccctctttttg ggtagctgtg    6960 gctgtgctgc agcttgatga ggtcaacttg tattcagcag gtaccgcact tcttgaacaa    7020
aacctgcata ctttagatag tctccgtata ttcaatgaca agagtccaga ggaagtattt    7080
atggcaatcc ggaatcctct ggagtggcac tgcaagcaaa tggatcattt tgttggactc    7140
aatttcaact ctaactttaa ctttgcattg gttggacacc ttttaaaagg gtacaggcat    7200
ccttcacctg ctattgttgc aagaacagtc agaattttac atacactact aactctggtt    7260
aacaaacaca gaaattgtga caatttgaa gtgaatacac agagcgtggc ctacttagca    7320
gctttactta cagtgtctga agaagttcga agtcgctgca gcctaaaaca tagaaagtca    7380
cttcttctta ctgatatttc aatggaaaat gttcctatgg atacatatcc cattcatcat    7440 ggtgacccctt cctataggac actaaaggag actcagccat ggtcctctcc caaaggttct    7500
```

| | | | |
|---|---|---|---|
| gaaggatacc | ttgcagccac | ctatccaact | gtcggccaga | ccagtccccg | agccaggaaa | 7560 |
| tccatgagcc | tggacatggg | gcaaccttct | caggccaaca | ctaagaagtt | gcttggaaca | 7620 |
| aggaaaagtt | ttgatcactt | gatatcagac | acaaaggctc | ctaaaaggca | agaaatggaa | 7680 |
| tcagggatca | caacaccccc | caaaatgagg | agagtagcag | aaactgatta | tgaaatggaa | 7740 |
| actcagagga | tttcctcatc | acaacagcac | ccacatttac | gtaaagtttc | agtgtctgaa | 7800 |
| tcaaatgttc | tcttggatga | agaagtactt | actgatccga | agatccaggc | gctgcttctt | 7860 |
| actgttctag | ctacactggt | aaaatatacc | acagatgagt | ttgatcaacg | aattctttat | 7920 |
| gaatacttag | cagaggccag | tgttgtgttt | cccaaagtct | ttcctgttgt | gcataatttg | 7980 |
| ttggactcta | agatcaacac | cctgttatca | ttgtgccaag | atccaaattt | gttaaatcca | 8040 |
| atccatggaa | ttgtgcagag | tgtggtgtac | catgaagaat | ccccaccaca | ataccaaaca | 8100 |
| tcttacctgc | aaagttttgg | ttttaatggc | ttgtggcggt | ttgcaggacc | gttttcaaag | 8160 |
| caaacacaaa | ttccagacta | tgctgagctt | attgttaagt | ttcttgatgc | cttgattgac | 8220 |
| acgtacctgc | ctggaattga | tgaagaaacc | agtgaagaat | ccctcctgac | tcccacatct | 8280 |
| ccttaccctc | ctgcactgca | gagccagctt | agtatcactg | ccaaccttaa | cctttctaat | 8340 |
| tccatgacct | cacttgcaac | ttcccagcat | tccccaggaa | tcgacaagga | gaacgttgaa | 8400 |
| ctctccccta | ccactggcca | ctgtaacagt | ggacgaactc | gccacggatc | cgcaagccaa | 8460 |
| gtgcagaagc | aaagaagcgc | tggcagtttc | aaacgtaata | gcattaagaa | gatcgtgtga | 8520 |

<210> SEQ ID NO 71
<211> LENGTH: 21
<212> TYPE: DNA
<213> ORGANISM: Artificial Sequence
<220> FEATURE:
<223> OTHER INFORMATION: Synthetic

<400> SEQUENCE: 71
gcattttgga actgggtaga a                                        21

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
aaccaccatg gactgaacaa                                           20

<210> SEQ ID NO 73
<211> LENGTH: 19
<212> TYPE: RNA
<213> ORGANISM: Artificial Sequence
<220> FEATURE:
<223> OTHER INFORMATION: Synthetic

<400> SEQUENCE: 73
ccagauccca cagacugau                                            19

<210> SEQ ID NO 74
<211> LENGTH: 19
<212> TYPE: RNA
<213> ORGANISM: Artificial Sequence
<220> FEATURE:
<223> OTHER INFORMATION: Synthetic

<400> SEQUENCE: 74

```
aucagucugu gggaucugg                                         19
```

```
<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
gcctggaaaa gaatgtgcag a                                      21

<210> SEQ ID NO 76
<211> LENGTH: 8444
<212> TYPE: DNA
<213> ORGANISM: Homo sapiens

<400> SEQUENCE: 76
atggccgcgc acaggccggt ggaatgggtc caggccgtgg tcagccgctt cgacgagcag   60
cttccaataa aaacaggaca gcagaacaca cataccaaag tcagtactga gcacaacaag  120
gaatgtctaa tcaatatttc caaatacaag ttttctttgg ttataagcgg cctcactact  180
attttaaaga atgttaacaa tatgagaata tttggagaag ctgctgaaaa aaatttatat  240
ctctctcagt tgattatatt ggatacactg gaaaaatgtc ttgctgggca accaaaggac  300
acaatgagat tagatgaaac gatgctggtc aaacagttgc tgccagaaat ctgccatttt  360
cttcacacct gtcgtgaagg aaaccagcat gcagctgaac ttcggaattc tgcctctggg  420
gttttatttt ctctcagctg caacaacttc aatgcagtct tagtcgcat  ttctaccagg  480 ttacaggaat taactgtttg ttcagaagac aatgttgatg ttcatgatat agaattgtta  540
cagtatatca atgtggattg tgcaaaatta aaacgactcc tgaaggaaac agcatttaaa  600
tttaaagccc taagaaggt tgcgcagtta gcagttataa atagcctgga aaagaatgtg  660
cagaaaagct atttgacttg gtggatggtt ttgctgaaag caccaaacgt aaagcagcag  720
tttggccact acaaatcatt ctccttatct tgtgtccaga ataatccag  gatatatcca  780 aagacgtggt tgatgaaaac aacatgaata agaagttatt tctggacagt ctacgaaaag  840
ctcttgctgg ccatggagga agtaggcagc tgacagaaag tgctgcaatt gcctgtgtca  900
aactgtgtaa agcaagtact tacatcaatt gggaagataa ctctgtcatt ttcctacttg  960
ttcagtccat ggtggttgat cttaagaacc tgcttttaa  tccaagtaag ccattctcaa 1020
gaggcagtca gcctgcagat gtggatctaa tgattgactg ccttgtttct tgctttcgta 1080
taagccctca caacaaccaa cactttaaga tctgcctggc tcagaattca ccttctacat 1140 tcactatgt  gctggtaaat tcactccatc gaatcatcac caattccgca ttggattggt 1200
ggcctaagat tgatgctgtg tattgtcact cggttgaact tcgaaatatg tttggtgaaa 1260
cacttcataa agcagtgcaa ggttgtggag cacacccagc aatacgaatg caccgagtc  1320 ttacatttaa agaaaaagta acaagcctta aatttaaaga aaaacctaca gacctggaga 1380
caagaagcta taagtatctt ctcttgtcca tggtgaaact aattcatgca gatccaaagc 1440
tcttgctttg taatccaaga aaacaggggc ccgaaaccca aggcagtaca gcagaattaa 1500
ttacagggct cgtccaactg gtccctcagt cacacatgcc agagattgct caggaagcaa 1560
tggaggctct gctggttctt catcagttag atagcattga tttgtggaat cctgatgctc 1620
ctgtagaaac attttgggag attagctcac aaatgctttt ttacatctgc aagaaattaa 1680
```

```
ctagtcatca aatgcttagt agcacagaaa ttctcaagtg gttgcgggaa atattgatct    1740
gcaggaataa atttcttctt aaaaataagc aggcagatag aagttcctgt cactttctcc    1800
ttttttacgg ggtaggatgt gatattcctt ctagtggaaa taccagtcaa atgtccatgg    1860
atcatgaaga attactacgt actcctggag cctctctccg aagggaaaa gggaactcct     1920 ctatggatag tgcagcagga tgcagcggaa ccccccgat ttgccgacaa gcccagacca     1980
aactagaagt ggccctgtac atgtttctgt ggaaccctga cactgaagct gttctggttg    2040
ccatgtcctg tttccgccac ctctgtgagg aagcagatat ccggtgtggg gtggatgaag    2100
tgtcagtgca taacctcttg cccaactata acacattcat ggagtttgcc tctgtcagca    2160
atatgatgtc aacaggaaga gcagcacttc agaaaagagt gatggcactg ctgaggcgca    2220
ttgagcatcc cactgcagga aacactgagg cttgggaaga tacacatgca aaatgggaac    2280
aagcaacaaa gctaatcctt aactatccaa aagccaaaat ggaagatggc caggctgctg    2340
aaagccttca caagaccatt gttaagaggc gaatgtccca tgtgagtgga ggaggatcca    2400
tagatttgtc tgacacagac tccctacagg aatggatcaa catgactggc ttcctttgtg    2460
cccttggggg agtgtgcctc cagcagagaa gcaattctgg cctggcaacc tatagcccac    2520
ccatgggtcc agtcagtgaa cgtaagggtt ctatgatttc agtgatgtct tcagaggga    2580 acgcagatac acctgtcagc aaatttatgg atcggctgtt gtccttaatg gtgtgtaacc    2640
atgagaaagt gggacttcaa atacggacca atgttaagga tctggtgggt ctagaattga    2700
gtcctgctct gtatccaatg ctatttaaca aattgaagaa taccatcagc aagttttttg    2760
actcccaagg acaggtttta ttgactgata ccaatactca atttgtagaa caaaccatag    2820
ctataatgaa gaacttgcta gataatcata ctgaaggcag ctctgaacat ctagggcaag    2880
ctagcattga aacaatgatg ttaaatctgg tcaggtatgt tcgtgtgctt gggaatatgg    2940
tccatgcaat tcaaataaaa acgaaactgt gtcaattagt tgaagtaatg atggcaagga    3000
gagatgacct ctcattttgc caagagatga aatttaggaa taagatggta gaatacctga    3060
cagactgggt tatgggaaca tcaaaccaag cagcagatga tgatgtaaaa tgtcttacaa    3120
gagatttgga ccaggcaagc atggaagcag tagtttcact tctagctggt ctccctctgc    3180
agcctgaaga aggagatggt gtggaattga tggaagccaa atcacagtta tttcttaaat    3240
acttcacatt atttttgaatg actgcagtga agttgaagat gaaagtgcgc    3300
aaacaggtgg caggaaacgt ggcatgtctc ggaggctggc atcactgagg cactgtacgg    3360
tccttgcaat gtcaaactta ctcaatgcca acgtagacag tggtctcatg cactccatag    3420
gcttaggtta ccacaaggat ctccagacaa gagctacatt tatggaagtt ctgacaaaaa    3480
tccttcaaca aggcacagaa tttgacacac ttgcagaaac agtattggct gatcggtttg    3540
agagattggt ggaactggtc acaatgatgg gtgatcaagg agaactccct atagcgatgg    3600
ctctggccaa tgtggttcct tgttctcagt gggatgaact agctcgagtt ctggttactc    3660
tgtttgattc tcggcattta ctctaccaac tgctctggaa catgttttct aaagaagtag    3720
aattggcaga ctccatgcag actctcttcc gaggcaacag cttggccagt aaaataatga    3780
cattctgttt caaggtatat ggtgctacct atctacaaaa actcctggat cctttattac    3840
gaattgtgat cacatcctct gattggcaac atgttagctt tgaagtggat cctaccaggt    3900
tagaaccatc agagagcctt gaggaaaacc agcggaacct ccttcagatg actgaaaagt    3960
tcttccatgc catcatcagt tcctcctcag aattcccccc tcaacttcga agtgtgtgcc    4020 actgttttata ccaggcaact tgccactccc tactgaataa agctacagta aaagaaaaaa    4080
```

```
aggaaaacaa aaaatcagtg gttagccagc gttccctca gaacagcatc ggtgcagtag    4140
gaagtgccat gttcctcaga tttatcaatc ctgccattgt ctcaccgtat gaagcaggga    4200
ttttagataa aaagccacca cctagaatcg aaagggctt gaagttaatg tcaaagatac    4260
ttcagagtat tgccaatcat gttctcttca caaaagaaga acatatgcgg cctttcaatg    4320
attttgtgaa aagcaacttt gatgcagcac gcaggttttt ccttgatata gcatctgatt    4380
gtcctacaag tgatgcagta aatcatagtc tttccttcat aagtgacggc aatgtgcttg    4440
ctttacatcg tctactctgg aacaatcagg agaaaattgg gcagtatctt ccagcaaca    4500 gggatcataa agctgttgga agacgacctt tgataagat ggcaacactt cttgcatacc    4560
tgggtcctcc agagcacaaa cctgtggcag atacacactg gtccagcctt aaccttacca    4620
gttcaaagtt tgaggaattt atgactaggc atcaggtaca tgaaaaagaa gaattcaagg    4680
ctttgaaaac gttaagtatt ttctaccaag ctgggacttc caaagctggg aatcctatt   4740 tttattatgt tgcacggagg ttcaaaactg gtcaaatcaa tggtgatttg ctgatatacc    4800
atgtcttact gactttaaag ccatattatg caaagccata tgaaattgta gtggacctta    4860
cccataccgg gcctagcaat cgctttaaaa cagactttct ctctaagtgg tttgttgttt    4920
ttcctggctt tgcttacgac aacgtctccg cagtctatat ctataactgt aactcctggg    4980
tcagggagta caccaagtat catgagcggc tgctgactgg cctcaaaggt agcaaaaggc    5040
ttgttttcat agactgtcct gggaaactgg ctgagcacat agagcatgaa caacagaaac    5100
tacctgctgc caccttggct ttagaagagg acctgaaggt attccacaat gctctcaagc    5160
tagctcacaa agacaccaaa gtttctatta agttggttc tactgctgtc caagtaactt    5220
cagcagagcg aacaaaagtc ctagggcaat cagtctttct aaatgacatt tattatgctt    5280
cggaaattga agaaatctgc ctagtagatg agaaccagtt caccttaacc attgcaaacc    5340
agggcacgcc gctcaccttc atgcaccagg agtgtgaagc cattgtccag tctatcattc    5400
atatccggac ccgctgggaa ctgtcacagc ccgactctat cccccaacac accaagattc    5460
ggccaaaaga tgtccctggg acactgctca atatcgcatt acttaattta ggcagttctg    5520
acccgagttt acggtcagct gcctataatc ttctgtgtgc cttaacttgt acctttaatt    5580
taaaaatcga gggccagtta ctagagacat caggtttatg tatccctgcc aacaacaccc    5640
tctttattgt ctctattagt aagacactgg cagccaatga gccacacctc acgttagaat    5700
ttttggaaga gtgtatttct ggatttagca aatctagtat tgaattgaaa cacctttgtt    5760
tggaatacat gactccatgg ctgtcaaatc tagttcgttt tgcaagcat aatgatgatg    5820 ccaaacgaca aagagttact gctattcttg acaagctgat aacaatgacc atcaatgaaa    5880
aacagatgta cccatctatt caagcaaaaa tatggggaag ccttgggcag attacagatc    5940
tgcttgatgt tgtactagac agtttcatca aaaccagtgc aacaggtggc ttgggatcaa    6000
taaaagctga ggtgatggca gatactgctg tagctttggc ttctggaaat gtgaaattgg    6060
tttcaagcaa ggttattgga aggatgtgca aaataattga caagacatgc ttatctccaa    6120
ctcctacttt agaacaacat cttatgtggg atgatattgc tattttagca cgctacatgc    6180
tgatgctgtc cttcaacaat tcccttgatg tggcagctca tcttccctac ctcttccacg    6240
ttgttacttt cttagtagcc acaggtccgc tctcccttag agcttccaca catggactgg    6300
tcattaatat cattcactct ctgtgtactt gttcacagct tcattttagt gaagagacca    6360
agcaagtttt gagactcagt ctgacagagt tctcattacc caaatttac ttgctgtttg    6420
```

| | |
|---|---|
| gcattagcaa agtcaagtca gctgctgtca ttgccttccg ttccagttac cgggacaggt | 6480 |
| cattctctcc tggctcctat gagagagaga cttttgcttt gacatccttg gaaacagtca | 6540 |
| cagaagcttt gttggagatc atggaggcat gcatgagaga tattccaacg tgcaagtggc | 6600 |
| tggaccagtg gacagaacta gctcaaagat ttgcattcca atataatcca tccctgcaac | 6660 |
| caagagctct tgttgtcttt gggtgtatta gcaaacgagt gtctcatggg cagataaagc | 6720 |
| agataatccg tattcttagc aaggcacttg agagttgctt aaaaggacct gacacttaca | 6780 |
| acagtcaagt tctgatagaa gctacagtaa tagcactaac caaattacag ccacttctta | 6840 |
| ataaggactc gcctctgcac aaagccctct tttgggtagc tgtggctgtg ctgcagcttg | 6900 |
| atgaggtcaa cttgtattca gcaggtaccg cacttcttga acaaacctg catactttag | 6960 |
| atagtctccg tatattcaat gacaagagtc cagaggaagt atttatggca atccggaatc | 7020 |
| ctctggagtg gcactgcaag caaatggatc attttgttgg actcaatttc aactctaact | 7080 |
| ttaactttgc attggttgga caccttttaa aagggtacag gcatccttca cctgctattg | 7140 |
| ttgcaagaac agtcagaatt ttacatacac tactaactct ggttaacaaa cacagaaatt | 7200 |
| gtgacaaatt tgaagtgaat acacagagcg tggcctactt agcagcttta cttacagtgt | 7260 |
| ctgaagaagt tcgaagtcgc tgcagcctaa acatagaaaa gtcacttctt cttactgata | 7320 |
| tttcaatgga aaatgttcct atggatacat atcccattca tcatggtgac ccttcctata | 7380 |
| ggacactaaa ggagactcag ccatggtcct ctcccaaagg ttctgaagga taccttgcag | 7440 |
| ccacctatcc aactgtcggc cagaccagtc cccgagccag gaaatccatg agcctggaca | 7500 |
| tggggcaacc ttctcaggcc aacactaaga agttgcttgg aacaaggaaa agttttgatc | 7560 |
| acttgatatc agacacaaag gctcctaaaa ggcaagaaat ggaatcaggg atcacaacac | 7620 |
| cccccaaaat gaggagagta gcagaaactg attatgaaat ggaaactcag aggatttcct | 7680 |
| catcacaaca gcacccacat ttacgtaaag tttcagtgtc tgaatcaaat gttctcttgg | 7740 |
| atgaagaagt acttactgat ccgaagatcc aggcgctgct tcttactgtt ctagctacac | 7800 |
| tggtaaaata taccacagat gagtttgatc aacgaattct ttatgaatac ttagcagagg | 7860 |
| ccagtgttgt gtttcccaaa gtcttttcctg ttgtgcataa tttgttggac tctaagatca | 7920 |
| acaccctgtt atcattgtgc caagatccaa atttgttaaa tccaatccat ggaattgtgc | 7980 |
| agagtgtggg gtaccatgaa gaatccccac cacaatacca aacatcttac ctgcaaagtt | 8040 |
| ttggttttaa tggcttgtgg cggtttgcag gaccgttttc aaagcaaaca caaattccag | 8100 |
| actatgctga gcttattgtt aagtttcttg atgccttgat tgcacgtac ctgcctggaa | 8160 |
| ttgatgaaga aaccagtgaa gaatccctcc tgactcccac atctccttac cctcctgcac | 8220 |
| tgcagagcca gcttagtatc actgccaacc ttaacctttc taattccatg acctcacttg | 8280 |
| caacttccca gcattcccca ggaatcgaca aggagaacgt tgaactctcc cctaccactg | 8340 |
| gccactgtaa cagtggacga actcgccacg gatccgcaag ccaagtgcag aagcaaagaa | 8400 |
| gcgctggcag tttcaaacgt aatagcatta agaagatcgt gtga | 8444 |

<210> SEQ ID NO 77
<211> LENGTH: 19
<212> TYPE: RNA
<213> ORGANISM: Artificial Sequence
<220> FEATURE:
<223> OTHER INFORMATION: Synthetic

<400> SEQUENCE: 77
ggaaaagaau gugcagaaa                                                    19

<210> SEQ ID NO 78
<211> LENGTH: 19
<212> TYPE: RNA
<213> ORGANISM: Artificial Sequence
<220> FEATURE:
<223> OTHER INFORMATION: Synthetic

<400> SEQUENCE: 78
uuucugcaca uucuuuucc                                                    19

<210> SEQ ID NO 79
<211> LENGTH: 636
<212> TYPE: DNA
<213> ORGANISM: Artificial Sequence
<220> FEATURE:
<223> OTHER INFORMATION: Synthetic

<400> SEQUENCE: 79
atggcttcgg ggcaaggccc aggtcctccc aggcaggagt gcggagagcc tgccctgccc        60
tctgcttctg aggagcaggt agcccaggac acagaggagg ttttccgcag ctacgttttt      120
taccgccatc agcaggaaca ggaggctgaa ggggtggctg ccctgccga cccagagatg       180 gtcaccttac ctctgcaacc tagcagcacc atggggcagg tgggacggca gctcgccatc      240
atcggggacg acatcaaccg acgctatgac tcagagttcc agaccatgtt gcagcacctg      300
cagcccacgg cagagaatgc ctatgagtac ttcaccaaga ttgccaccag cctgtttgag      360
agtggcatca attggggccg tgtggtggct cttctgggct tcggctaccg tctggcccta      420
cacgtctacc agcatggcct gactggcttc ctaggccagg tgacccgctt cgtggtcgac      480
ttcatgctgc atcactgcat tgcccggtgg attgcacaga ggggtggctg ggtggcagcc      540
ctgaacttgg gcaatggtcc catcctgaac gtgctggtgg ttctgggtgt ggttctgttg      600
ggccagtttg tggtacgaag attcttcaaa tcatga                                636

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
cctgtttgag agtggcatca a                                                 21

<210> SEQ ID NO 81
<211> LENGTH: 21
<212> TYPE: DNA
<213> ORGANISM: Artificial Sequence
<220> FEATURE:
<223> OTHER INFORMATION: Synthetic

<400> SEQUENCE: 81
ttgatgccac tctcaaacag g                                                 21

<210> SEQ ID NO 82
<211> LENGTH: 19
<212> TYPE: RNA
<213> ORGANISM: Artificial Sequence
<220> FEATURE:
<223> OTHER INFORMATION: Synthetic

<400> SEQUENCE: 82
ggucaccuua ccucugcaa                                                  19

<210> SEQ ID NO 83
<211> LENGTH: 19
<212> TYPE: RNA
<213> ORGANISM: Artificial Sequence
<220> FEATURE:
<223> OTHER INFORMATION: Synthetic

<400> SEQUENCE: 83
uugcagaggu aaggugacc                                                  19

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
tctgcttctg gcaccatggg                                                 20

<210> SEQ ID NO 85
<211> LENGTH: 501
<212> TYPE: DNA
<213> ORGANISM: Homo sapiens

<400> SEQUENCE: 85
atggcttcgg ggcaaggccc aggtcctccc aggcaggagt gcggagagcc tgccctgccc      60
tctgcttctg gcaccatggg gcaggtggga cggcagctcg ccatcatcgg ggacgacatc     120
aaccgacgct atgactcaga gttccagacc atgttgcagc acctgcagcc cacggcagag     180
aatgcctatg agtacttcac caagattgcc accagcctgt tgagagtgg catcaattgg      240 ggccgtgtgg tggctcttct gggcttcggc taccgtctgg ccctacacgt ctaccagcat     300
ggcctgactg gcttcctagg ccaggtgacc cgcttcgtgg tcgacttcat gctgcatcac     360
tgcattgccc ggtggattgc acagaggggt ggctgggtgg cagccctgaa cttgggcaat     420
ggtcccatcc tgaacgtgct ggtggttctg ggtgtggttc tgttgggcca gtttgtggta     480
cgaagattct tcaaatcatg a                                              501

<210> SEQ ID NO 86
<211> LENGTH: 19
<212> TYPE: RNA
<213> ORGANISM: Artificial Sequence
<220> FEATURE:
<223> OTHER INFORMATION: Synthetic

<400> SEQUENCE: 86
cccucugcuu cuggcacca                                                  19

<210> SEQ ID NO 87
<211> LENGTH: 19
<212> TYPE: RNA
<213> ORGANISM: Artificial Sequence
<220> FEATURE:
<223> OTHER INFORMATION: Synthetic

<400> SEQUENCE: 87
uggugccaga agcagaggg                                                  19

What is claimed is:

1. A method of detecting a Phosphoinositide 3-kinase catalytic delta (PIK3CD) splice variant comprising:
   a) obtaining a tissue sample from a patient; and
   b) detecting the presence of a PIK3CD transcript without exon 20 in the sample's total mRNA.

2. The method of claim 1, further comprising extracting the total mRNA prior to detecting the presence of the PIK3CD transcript without exon 20.

3. The method of claim 2, further comprising reverse transcribing the total mRNA to cDNA.

4. The method of claim 3, wherein detecting the presence of PIK3CD transcript without exon 20 is by polymerase chain reaction using the cDNA as a template.

5. The method of claim 3, wherein detecting the presence of PIK3CD transcript without exon 20 is by cDNA sequencing.

6. The method of claim 3, wherein detecting the presence of PIK3CD transcript without exon 20 is by polymerase chain reaction using the cDNA as a template with primers specific to exon 20 of PIK3CD transcript and/or a junction of PIK3CD transcript without exon 20.

7. The method of claim 1, wherein detecting the presence of PIK3CD transcript without exon 20 is by hybridization to probes specific to exon 20 of PIK3 CD transcript and/or a junction of PIK3CD transcript without exon 20.

8. The method of claim 1, wherein detecting the presence of PIK3CD transcript without exon 20 is by detecting the presence of any part of the PIK3CD mRNA and determining the size of the mRNA such that exon 20 can be said to be absent based on the length of the PIK3CD mRNA.

9. A method of detecting a Phosphoinositide 3-kinase catalytic delta (PIK3CD) splice variant comprising:
   a) obtaining a tissue sample from a patient; and
   b) detecting the presence of a PIK3CD transcript comprising a nucleic acid sequence of SEQ ID No. 11 in the sample's total mRNA.

10. The method of claim 9, further comprising extracting the total mRNA prior to detecting the presence of the PIK3CD transcript comprising a nucleic acid sequence of SEQ ID No. 11.

11. The method of claim 10, further comprising reverse transcribing the total mRNA to cDNA.

12. The method of claim 11, wherein detecting the presence of PIK3CD transcript comprising a nucleic acid sequence of SEQ ID No. 11 is by polymerase chain reaction using the cDNA as a template.

13. The method of claim 11, wherein detecting the presence of PIK3CD transcript comprising a nucleic acid sequence of SEQ ID No. 11 is by cDNA sequencing.

14. The method of claim 11, wherein detecting the presence of PIK3CD transcript comprising a nucleic acid sequence of SEQ ID No. 11 is by polymerase chain reaction using the cDNA as a template with primers specific to exon 20 of PIK3CD transcript and/or a junction of PIK3CD transcript without exon 20.

15. The method of claim 9, wherein detecting the presence of PIK3CD transcript comprising a nucleic acid sequence of SEQ ID No. 11 is by hybridization to probes specific to exon 20 of PIK3CD transcript and/or a junction of PIK3CD transcript without exon 20.

16. The method of claim 9, wherein detecting the presence of PIK3CD transcript comprising a nucleic acid sequence of SEQ ID No. 11 is by detecting the presence of any part of the PIK3CD mRNA and determining the size of the mRNA such that exon 20 can be said to be absent based on the length of the PIK3CD mRNA.

* * * * *